(12) United States Patent
Maletinska et al.

(10) Patent No.: US 9,937,235 B2
(45) Date of Patent: *Apr. 10, 2018

(54) LIPIDATED PEPTIDES AS ANTI-OBESITY AGENTS

(71) Applicant: USTAV ORGANICKE CHEMIE A BIOCHEMIE AKADEMIE VED CR, V.V.I, Prague (CZ)

(72) Inventors: Lenka Maletinska, Prague (CZ); Blanka Zelezna, Prague (CZ); Miroslava Blechova, Usti nad Labem (CZ); Andrea Popelova, Prague (CZ)

(73) Assignee: USTAV ORGANICKE CHEMIE A BIOCHEMIE AKADEMIE VED CR, V.V.I., Prague (CZ)

( * ) Notice: Subject to any disclaimer, the term of this patent is extended or adjusted under 35 U.S.C. 154(b) by 0 days.

This patent is subject to a terminal disclaimer.

(21) Appl. No.: 14/414,034

(22) PCT Filed: Jul. 11, 2013

(86) PCT No.: PCT/IB2013/001837
§ 371 (c)(1),
(2) Date: Jan. 9, 2015

(87) PCT Pub. No.: WO2014/009808
PCT Pub. Date: Jan. 16, 2014

(65) Prior Publication Data
US 2015/0175674 A1   Jun. 25, 2015

(30) Foreign Application Priority Data
Jul. 12, 2012 (CZ) .................................. 2012-476

(51) Int. Cl.
A61K 38/00    (2006.01)
A61K 38/22    (2006.01)
C07K 14/575   (2006.01)
A61K 47/54    (2017.01)

(52) U.S. Cl.
CPC ........ *A61K 38/2257* (2013.01); *A61K 47/543* (2017.08); *C07K 14/575* (2013.01)

(58) Field of Classification Search
None
See application file for complete search history.

(56) References Cited

U.S. PATENT DOCUMENTS

2003/0171270 A1* 9/2003 Civelli .................. G01N 33/74 435/7.8

FOREIGN PATENT DOCUMENTS

| WO | WO2006/066258 | 6/2006 |
| WO | WO2009/033668 | 3/2009 |
| WO | WO2009/126132 | 10/2009 |
| WO | 2012/176172 A2 | 12/2012 |
| WO | WO 2012/176172 | * 12/2012 |
| WO | WO2014/009808 | 1/2014 |

OTHER PUBLICATIONS

Pinto et al, Modification with Organometallic Compounds Improves Crossing of the Blood-Brain Barrier of [Leu5]-Enkephalin Derivatives in an In Vitro Model System, (ChemBioChem 2009, 10, 1852-1860).*
Roland et al. (Endocrinology. Dec. 1999;140(12):5736-45).*
Bechtold et al. Prolactin—releasing peptide mediates cholecystokinin-induced satiety in mice. Endocrinology 147:4723-4729 (2006).
Ben-Jonathan et al. What Can We Learn from Rodents about Prolactin in Humans? Endocrine Reviews 29(1):1-41 (2008).
Bjursell et al. GPR10 deficiency in mice results in altered energy expenditure and obesity. Biochem Biophys Res Commun 363:633-638 (2007).
Boyle et al. Structure-activity studies on prolactin-releasing peptide (PrRP). Analogues of PrRP-(19-31)-peptide. Journal of Peptide Science 11(3):161-165 (2005).
Ellacott et al. Repeated administration of the anorectic factor prolactin-releasing peptide leads to tolerance to its effects on energy homeostasis. Am .1 Physiol Regul Integr Comp Physiol 285:R1005-1010 (2003).
Gu et al. The prolactin-releasing peptide receptor (GPR10) regulates body weight homeostasis in mice. J Mot Neurosci. 22:93-103 (2004).
Heal et al. What is the prognosis for new centrally-acting anti-obesity drugs? Neuropharmacology 63:132-146 (2012).
Hinuma et al. A prolactin-releasing peptide in the brain. Nature 393:272-276 (1998).
Jarry et al. Prolactin-releasing peptides do not stimulate prolactin release in vivo. Neuroendocrinology 71:262-267 (2000).
Langmead et al. Characterization of the binding of [(125)1]-human prolactin releasing peptide (PrRP) to GPR10, a novel G protein coupled receptor. Br J Pharmacol. 131:683-688 (2000).
Lawrence at al. Alternative role for prolactin-releasing peptide in the regulation of food intake. Nat. Neurosci 3:645-646 (2000).
Lawrence et al. Anorectic actions of prolactin-releasing peptide are mediated by corticotrophin-releasing hormone receptors. Am J Physiol Regul Integr Comp Physiol 286:R101-107 (2004).
Maixnerova et al. Characterization of prolactin-releasing peptide: Binding, signaling and hormone secretion in rodent pituitary cell lines endogenously pressing its receptor. Peptides 32(4):811-817 (2010).

(Continued)

*Primary Examiner* — Jennifer Pitrak McDonald
*Assistant Examiner* — Sergio Coffa
(74) *Attorney, Agent, or Firm* — Notaro, Michalos & Zaccaria P.C.

(57) ABSTRACT

Lipidated peptides, analogs of both forms of the prolactin-releasing peptide, PrRP31 and PrRP20, represent anorexigenic compounds that lower food intake and function in the brain after peripheral administration. The analogs PrRP31 and PrRP20 lipidated at the N-terminus by myristic or palmitic acids bind with high affinity to the endogenous receptor GPR10 in the rat pituitary cell line RC-4B/C and CHO cell line with transfected human receptor. These lipidated peptides also significantly decrease, in a dose-dependent manner, the food intake in fasted mice and have similar effects in comparable doses as centrally administered natural PrRP31, these effects are, however, stronger and longer lasting. Lipidation of an effective anorexigenic neuropeptide PrRP induces a central effect after peripheral administration and thus makes the lipidated analogs of PrRP a promising anti-obesity drug.

10 Claims, 6 Drawing Sheets

(56) References Cited

OTHER PUBLICATIONS

Maixnerova et al. Structure-activity relationship of CART (cocaine- and amphetamine-regulated transcript) peptide fragments. Peptides 28:1945-1953 (2007).

Maletinska et al. Biological properties of prolactin-releasing peptide analogs with a modified aromatic ring of a C-terminal phenylalanine amide. Peptides 32(9):1887-1892(2011).

Maletinska et al. Characterization of new stable ghrelin analogs with prolonged orexigenic potency. J Pharmacol Exp Ther. 340:781-786 (2012).

Mochiduki et al. Stress response of prolactin-releasing peptide knockout mice as to glucocorticoid secretion. J Neuroendocrinol. 22:576-584 (2010).

PCT/IB/2013/001837 International Preliminary Report on Patentability dated Jan. 13, 2015.

PCT/IB/2013/001837 International Search Report and Written Opinion dated Jan. 2, 2014.

Roland et al. Anatomical distribution of prolactin-releasing peptide and its receptor suggests additional functions in the central nervous system and periphery. Endocrinology 140:5736-5745 (1999).

Satoh et al. Characterization and distribution of prolactin releasing peptide (PrRP) binding sites in the rat-evidence for a novel binding site subtype in cardiac and skeletal muscle. Br J Pharmacol. 129:1787-1793 (2000).

Strader et al. Gastrointestinal hormones and food intake. Gastroenterology 128:175-191 (2005).

Sun et al. Physiological roles of prolactin-releasing peptide. Regulatory Peptides 126(1-2):27-33 (2005).

Takayanagi et al. Endogenous prolactin-releasing peptide regulates food intake in rodents. Journal of Clinical Investigation 118(12):4014-4024 (2008).

Witt et al. Peptide drug modifications to enhance bioavailability and blood-brain barrier permeability. Peptides 22(12):2329-2343 (2001).

Wettstein, J.G., et al. Central Nervous System Pharmacology of Neuropeptide, Pharmac, Ther. vol. 65, pp. 397-414, 1995.

Murase, Takashi, et al. Neuropeptide FF Reduce Food Intake in Rats, Peptides, vol. 17, No. 2. pp. 353-354, 1996.

Engstrom, Mia, et al. Prolactin Releasing Peptide Has High Affinity and Efficacy at Neuropeptide FF2 Receptors, Pharmac, Ther. vol. 306, No. 3, 2003.

Lagersrom, Marlin, et al. Origin of the Prolactin-Releasing Hormone Receptors: Evidence of Coevolution between PRLH and a Redundant Neuropeptide Y Receptor during Vertebrate Evolution, Science Direct, Genomics 85, 2005.

Ishihara, Akane, et al. A Neuropeptide Y Y5 Antagonist Selectively Ameliorates Body Weight Gain and Associated Parameters in Diet-Induced Obese Mice, PNAS,vol. 103, No. 18, pp. 7154-7158, May 2006.

Daspgupt, P. et al. Lipophilization of Somatostatin Analog RC-160 with Long Chain Fatty Acid Improves its Antiproliferative and Antiangiogenic Activity in vitro, British Jrnl Pharmac 2000 129, p. 101-109.

* cited by examiner

LIPIDATED PEPTIDES AS ANTI-OBESITY AGENTS

CROSS-REFERENCE

This application is a U.S. National Stage entry under 35 U.S.C. 371 of International Application No. PCT/IB2013/001837, filed Jul. 11, 2013, which claims the benefit of Czech Republic Application No. PV 2012 476, filed Jul. 12, 2012, which is incorporated herein by reference.

SEQUENCE LISTING

The instant application contains a Sequence Listing which has been submitted in ASCII format via EFS-Web and is hereby incorporated by reference in its entirety. Said ASCII copy, created on May 15, 2015, is named 45071-702-831-seq-listing.txt and is 94,690 bytes in size.

FIELD OF THE INVENTION

The embodiments described herein relate to lipidated analogs of prolactin-releasing peptides and the use of these analogs as anorexigenic compounds that lower food intake. The synthesis of these lipidated peptides is described herein, as well as their pharmacological effects in vitro and in vivo.

BACKGROUND OF THE INVENTION

In both the developing and developed countries, obesity is an increasingly growing problem, for which no effective therapies are available. Current medications are typically associated with adverse side effects. For example, the only medication available in the Czech Republic is Orlistat, an inhibitor of intestinal lipase which lowers the absorption of lipids from the small intestine. It is, however, associated with adverse effects, such as diarrhea. Sibutramine, a serotonin-norepinephrine reuptake inhibitor that induces satiety sensation was withdrawn from the market for increased risk of heart disease found during its use (Strader, A., et al., "Gastrointestinal hormones and food intake," *Gastroenterology*, 128:175-191, 2005; Heal, D. J. et al., "What is the prognosis for new centrally-acting anti-obesity drugs?" *Neuropharmacology*, 63:132-146, 2012).

SUMMARY OF THE INVENTION

Embodiments disclosed herein relate to lipidated analog of prolactin-releasing peptide having a general formula:

$J^1$-$J^2$-rRPsGRt-NH$_2$ (SEQ ID NO: 1)     (I), wherein $J^1$ represents a fatty acid C6 to C18 bound by an amide bond to an amino group of a N-terminal amino acid;

$J^2$ represents a chain of 13 or 24 amino acids;

r is isoleucine, alanine, or phenylglycine;

s is valine or phenylglycine; and t is phenylalanine or an amino acid with a side chain containing CH$_2$—Ar or CH$_2$—S—CH$_2$—Ar, wherein Ar represents phenyl or naphtyl, optionally substituted by a halogen or nitro group.

Additional embodiments disclosed herein relate to lipidated analogs of prolactin-releasing peptide having a general formula:

$J^1$-k-$J^3$-rRPsGRt-NH$_2$ (SEQ ID NO: 2)     (II), wherein $J^1$ represents a fatty acid C6 to C18 bound by an amide bond to an amino group of a N-terminal amino acid;

k is chosen from serine, threonine or diaminopropionic acid;

$J^3$ represents a chain of 23 or 12 amino acids;

r is isoleucine, alanine, or phenylglycine;

s is valine or phenylglycine; and t is phenylalanine or an amino acid with a side chain containing CH$_2$—Ar or CH$_2$—S—CH$_2$—Ar, where Ar represents phenyl or naphtyl, optionally substituted by halogen or nitro group.

Further embodiments disclosed herein relate to lipidated analogs of prolactin-releasing peptide having a general formula:

$J^1$-kRmHnHSqEuRTPDINPAWYmoRprRPsGRt-NH$_2$
(SEQ ID NO: 3)     (III), wherein k is serine, threonine or diaminopropionic acid;

m is chosen from threonine, alanine or methylalanine;

n is glutamine or arginine;

q is methionine or norleucine;

u is threonine or isoleucine;

o is glycine or serine;

p is glycine, alanine, proline or N-methylglycine;

r is isoleucine, alanine or phenylglycine;

s is valine or phenylglycine;

t is phenylalanine or an amino acid with a side chain containing CH$_2$—Ar or CH$_2$—S—CH$_2$—Ar, where Ar represents phenyl or naphtyl, optionally substituted by halogen or nitro group; and $J^1$ represents a fatty acid C6 to C18 bound by the amide bond to the amino group of the N-terminal amino acid, wherein the chain of amino acids kRmHnHSqEuRTPDINPAWYmoRp (SEQ ID NO: 4) is optionally shortened by eliminating from 1 to 10 amino acids.

Yet further embodiments herein relate to lipidated analogs of prolactin-releasing peptide, having a general formula $J^1$-kRmHnHSqEuRTPDINPAWYmoRprRPsGRt-NH$_2$
(SEQ ID NO: 3)     (III), wherein k is serine, threonine or diaminopropionic acid;

m is threonine, alanine or methylalanine;

n is glutamine or arginine;

q is methionine or norleucine;

u is threonine or isoleucine;

o is glycine or serine;

p is glycine, alanine, proline or N-methylglycine;

r is isoleucine, alanine or phenylglycine;

s is valine or phenylglycine;

t is phenylalanine or an amino acid with side chain containing CH$_2$—Ar or CH$_2$—S—CH$_2$—Ar, where Ar represents phenyl or naphtyl, optionally substituted by halogen or nitro group; and $J^1$ represents a fatty acid C6 to C18 bound by the amide bond to the amino group of the N-terminal amino acid, where the chain of amino acids kRmHnHSqEuRTPDINPAWYmoRp (SEQ ID NO: 4) is optionally shortened from its N-terminus by eliminating from 1 to 10 amino acids.

Additional embodiments disclosed herein relate to lipidated analogs of prolactin-releasing peptide chosen from the group containing peptides of formula $J^1$-kRmHnHSqEuRTPDINPAWYmoRprRPsGRt-NH$_2$ (SEQ ID NO: 3)     (III), or $J^1$-TPDINPAWYmoRprRPsGRt-NH$_2$ (SEQ ID NO: 5)     (IV), wherein
k is serine, threonine or diaminopropionic acid;
m is threonine, alanine or methylalanine;
n is glutamine or arginine;
q is methionine or norleucine;
u is threonine or isoleucine;
o is glycine or serine;
p is glycine, alanine, proline or N-methylglycine;
r is isoleucine, alanine or phenylglycine;
s is valine or phenylglycine;
t is phenylalanine or an amino acid with side chain containing CH$_2$—Ar or CH$_2$—S—CH$_2$—Ar, where Ar represents phenyl or naphtyl, optionally substituted by halogen or nitro group; and
$J^1$ represents a fatty acid C6 to C18 bound by the amide bond to the amino group of the N-terminal amino acid.

In some embodiments, substitutions of amino acids in positions 1-24 of formula III or in positions 1-13 of formula IV are performed that do not increase the binding affinity value of the resulting lipidated peptide to the receptor GPR10 over $K_i$ $10^{-6}$ mol·l$^{-1}$, measured in the rat hypophyseal cell line RC-4B/C grown on 24-well plates, which had their bottom coated with polyethyleneimine, up to the optimal density of 300-450 thousand per well; then the following agents are added: binding buffer containing 20 mmol·l$^{-1}$ HEPES, pH 7.4, 118 mmol·l$^{-1}$ NaCl, 4.7 mmol·l$^{-1}$ KCl, 5 mmol·l$^{-1}$ MgCl$_2$, 5.5 mmol·l$^{-1}$ glucose, 1 mg/ml bovine serum albumin, 0.1 mg/ml bovine pancreatic trypsin inhibitor; unlabelled analogs of PrRP of final concentration within $10^{-11}$ to $10^{-4}$ mol·l$^{-1}$, and $^{125}$I—PrRP31 of final concentration of $10^{-10}$ mol·l$^{-1}$; the plate is incubated for 60 minutes at room temperature and thereafter the cells are solubilized in 0.1 mol/l solution of NaOH and the radioactivity bound to the cell is counted in the γ-counter.

Additional embodiments relate to lipidated analogs of of prolactin-releasing peptide of formula:

$J^1$-SRmHnHSqEuRTPDINPAWYmoRprRPsGRt-NH$_2$ (SEQ ID NO: 6)     (IV), wherein
m is threonine, alanine or methylalanine;
n is glutamine or arginine;
q is methionine or norleucine;
u is threonine or isoleucine;
o is glycine or serine;
p is glycine, alanine, proline or N-methylglycine;
r is isoleucine, alanine or phenylglycine, s is chosen from valine or phenylglycine;
t is phenylalanine or an amino acid with side chain containing CH$_2$—Ar or CH$_2$—S—CH$_2$—Ar, where Ar represents phenyl or naphtyl, optionally substituted by halogen or nitro group; and
$J^1$ represents a fatty acid C6 to C18 bound by an amide bond to the amino group of the N-terminal amino acid.

In some embodiments, the C-terminal amino acid of any of the lipidated analogs of prolactin-releasing peptide disclosed herein is naphtylalanine, benzylcystein, benzylhistidine, pentafluorophenylalanine, or nitrophenylalanine.

In some embodiments, the fatty acid of any of the lipidated analogs of prolactin-releasing peptide disclosed herein is selected from the group consisting of fatty acids with 6 to 18 carbons and fatty acids with 13 to 18 carbon atoms. In some embodiments, the fatty acid is 6, 7, 8, 9, 10, 11, 12, 13, 14, 15, 16, 17, or 18 carbon atoms.

Further embodiments relate to a lipidated analog of prolactin-releasing peptide selected from the group consisting of:
Dpr(oct))RmHnHSNleETRTPDINPAWYmoRGrRPs-GRF-NH$_2$ (SEQ ID NO: 7),
(Dpr(dodec))RmHnHSNleETRTPDINPAWYmoRGr-RPsGRF-NH$_2$ (SEQ ID NO: 8),
(Dpr(tridec))RmHnHSNleETRTPDINPAWYmoRGr-RPsGRF-NH$_2$ (SEQ ID NO: 9),
(Dpr(myr))RmHnHSNleETRTPDINPAWYmoRGrRPs-GRF-NH$_2$ (SEQ ID NO: 10),
(Dpr(palm))RmHnHSNleETRTPDINPAWYmoRGrRPs-GRF-NH$_2$ (SEQ ID NO: 11),
(myr)TPDINPAWYmoRGrRPsGRF-NH$_2$ (SEQ ID NO: 12),
(palm)TPDINPAWYmoRGrRPsGRF-NH$_2$ (SEQ ID NO: 13),
(Dpr(oct))RmHnHSNleETRTPDINPAWYmoRGr-RPsGR 1-Nal-NH$_2$ (SEQ ID NO: 14),
(Dpr(dodec))RmHnHSNleETRTPDINPAWYmoRGr-RPsGR 1-Nal-NH$_2$ (SEQ ID NO: 15),
(Dpr(tridec))RmHnHSNleETRTPDINPAWYmoRGr-RPsGR 1-Nal-NH$_2$ (SEQ ID NO: 16),
(Dpr(myr))RmHnHSNleETRTPDINPAWYmoRGr-RPsGR 1-Nal-NH$_2$ (SEQ ID NO: 17),
(Dpr(palm))RmHnHSNleETRTPDINPAWYmoRGr-RPsGR 1-Nal-NH$_2$ (SEQ ID NO: 18),
(myr)TPDINPAWYmoRGrRPsGR 1-Nal-NH$_2$ (SEQ ID NO: 19), and
(palm)TPDINPAWYmoRGrRPsGR 1-Nal-NH$_2$ (SEQ ID NO: 20);
wherein m is T or A; o is G or S; n is Q or R; r is I, A or phenylglycine; s is V or phenylglycine, and wherein at the peptide positions 1 to 24, such substitutions of amino acids may be performed that do not increase the binding affinity value of the resulting lipidated peptide to the receptor GPR10 over $K_i$ $10^{-6}$ mol·l$^{-1}$, and its anorexic activity evaluated by the food intake test in fasted mice after both peripheral and central administration is equal or higher as compared to administered PrRP.

More embodiments relate to a lipidated analog of prolactin-releasing peptide selected from the group consisting of:
(Dpr(oct))RmHnHSNleETRTPDINPAWYmoRGIR-PVGRF-NH$_2$ (SEQ ID NO: 21),
(Dpr(dodec))RmHnHSNleETRTPDINPAWYmoRGIR-PVGRF-NH$_2$ (SEQ ID NO: 22),
(Dpr(tridec))RmHnHSNleETRTPDINPAWYmoRGIR-PVGRF-NH$_2$ (SEQ ID NO: 23),
(Dpr(myr))RmHnHSNleETRTPDINPAWYmoRGIR-PVGRF-NH$_2$ (SEQ ID NO: 24),
(Dpr(palm))RmHnHSNleETRTPDINPAWYmoRGIR-PVGRF-NH$_2$ (SEQ ID NO: 25),
(myr)TPDINPAWYmoRGIRPVGRF-NH$_2$ (SEQ ID NO: 26),
(palm)TPDINPAWYmoRGIRPVGRF-NH$_2$ (SEQ ID NO: 27),
(Dpr(oct))RmHnHSNleETRTPDINPAWYmoRGIR-PVGR 1-Nal-NH$_2$ (SEQ ID NO: 28), (Dpr(dodec))RmHnHSNleETRTPDINPAWYmoRGIR-PVGR 1-Nal-NH$_2$ (SEQ ID NO: 29),
(Dpr(tridec))RmHnHSNleETRTPDINPAWYmoRGIR-PVGR 1-Nal-NH$_2$ (SEQ ID NO: 30),
(Dpr(myr))RmHnHSNleETRTPDINPAWYmoRGIR-PVGR 1-Nal-NH$_2$ (SEQ ID NO: 31),
(Dpr(palm))RmHnHSNleETRTPDINPAWYmoRGIR-PVGR 1-Nal-NH$_2$ (SEQ ID NO: 32),
(myr)TPDINPAWYmoRGIRPVGR 1-Nal-NH$_2$ (SEQ ID NO: 33), and
(palm)TPDINPAWYmoRGIRPVGR 1-Nal-NH$_2$ (SEQ ID NO: 34); wherein
m is T or A;
o is G or S;
n is Q or R, and wherein
at the peptide positions 1 to 24, such substitutions in amino acids may be performed that do not increase the binding affinity value of the lipidated analog to the receptor GPR10 over $K_i$ $10^{-6}$ mol·l$^{-1}$ and its anorexic activity evaluated by the food intake test in fasted mice after both peripheral and central administration is equal or higher as compared to administered PrRP.

Additional embodiments relate to a lipidated analog of prolactin-releasing peptide selected from the group consisting of:
J$^a$-SRAHQHSMETRTPDINPAWYTGRGIRPVGRF-NH$_2$ (SEQ ID NO: 35),
J$^a$-SRTHRHSMEIRTPDINPAWYASRGIRPVGRF-NH$_2$ (SEQ ID NO: 36),
(N-palm)-SRTHRHSMEIRTPDINPAWYASRGIR-PVGRF-NHMe (SEQ ID NO: 37),
(N-palm)-SRTHRHSMEIRTPDINPAWYASRGIR-PVGRF-NOMe (SEQ ID NO: 38),
(N-myr)-TPDINPAWYTGRGIRPVGRF-NH$_2$ (SEQ ID NO: 39),
(N-myr)-TPDINPAWYASRGIRPVGRF-NH$_2$ (SEQ ID NO: 40),
(N-oct)-TPDINPAWYASRGIRPVGRF-NH$_2$ (SEQ ID NO: 41),
(N-dec)-TPDINPAWYASRGIRPVGRF-NH$_2$ (SEQ ID NO: 42),
(N-dodec)-TPDINPAWYASRGIRPVGRF-NH$_2$ (SEQ ID NO: 43),
J$^{1'}$-SRAHQHS Nle ETRTPDINPAWYTGRGIRPVGRF-NH$_2$ (SEQ ID NO: 44), J$^a$-SRAHQHS Nle ETRTPDINPAWYTGRGIRPVGR 1-Nal-NH$_2$ (SEQ ID NO: 45),
J$^a$-SRAHQHS Nle ETRTPDINPAWYTGRGIRPVGR PheCl$_2$—NH$_2$ (SEQ ID NO: 46),
J$^a$-SRAHQHS Nle ETRTPDINPAWYTGRGIRPVGR PheNO$_2$—NH$_2$ (SEQ ID NO: 47),
J$^a$-SRAHQHS Nle ETRTPDINPAWYTGRGIRPVGR PheF$_5$—NH$_2$ (SEQ ID NO: 48),
J$^a$-SRAHQHS Nle ETRTPDINPAWYTGRGIRPVGRY-NH$_2$ (SEQ ID NO: 49),
J$^a$-SRAHRHS Nle EIRTPDINPAWYASRGIRPVGRY-NH$_2$ (SEQ ID NO: 50),
(N-myr)-Nle-ETRTPDINPAWYTGRGIRPVGRF-NH$_2$ (SEQ ID NO: 51),
(N-myr)-QHSMETRTPDINPAWYTGRGIRPVGRF-NH$_2$ (SEQ ID NO: 52),
(N-myr)-QHSMETRTPDINPAWYASRGIRPVGRF-NH$_2$ (SEQ ID NO: 53) and
(N-palm)SRTHRHSMEIRTPDINPAWYASRGIR-PVGRF-NOMe SEQ ID NO: 54; wherein
J$^{1'}$ is palmitic acid, myristic acid or stearic acid; and
J$^a$ is palmitic acid or myristic acid.

Some embodiments described herein relate to the use of lipidated analogs of prolactin-releasing peptide disclosed herein as anorexigenic agents lowering food intake after peripheral administration.

Some embodiments described herein relate to the use of lipidated analogs of prolactin-releasing peptide disclosed herein as an agent for the treatment of obesity.

Additional embodiments described herein relate to a lipidated analog of prolactin-releasing peptide selected from:
(palm)-SRTHRHSMEIRTPDINPAWYASRGIRPVGRF-NH$_2$ (SEQ ID NO: 55), or
(myr)-SRTHRHSMEIRTPDINPAWYASRGIRPVGRF-NH$_2$ (SEQ ID NO: 56).

In some embodiments, the lipidated analog of prolactin-releasing peptide has the structure:
(palm)-SRTHRHSMEIRTPDINPAWYASRGIRPVGRF-NH$_2$ (SEQ ID NO: 55).

Additional embodiments described herein relate to lipidated analog of prolactin-releasing peptide according to formula:

$$J^a\text{-TPDINPAWYmoRGIRPVGRF-NH}_2 \text{ (SEQ ID NO: 57),}$$

wherein
J$^a$ is palmitic acid or myristic acid; m is T or A; and o is G or S. In some embodiments, J$^a$ is myristic acid.

In some embodiments, the lipidated analog of prolactin-releasing peptide has the structure:
(myr)-TPDINPAWYASRGIRPVGRF-NH$_2$ (SEQ ID NO: 40).

Further embodiments relate to a method of preventing or treating a subject diagnosed with or susceptible to having obesity comprising administering a lipidated analog of prolactin-releasing peptide disclosed herein. In some embodiments, the lipidated analog is:
(palm)-SRTHRHSMEIRTPDINPAWYASRGIRPVGRF-NH$_2$ (SEQ ID NO: 55), or
(myr)-TPDINPAWYASRGIRPVGRF-NH$_2$ (SEQ ID NO: 40).

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Prolactin-Releasing Peptide (PrRP)

Figure 1:
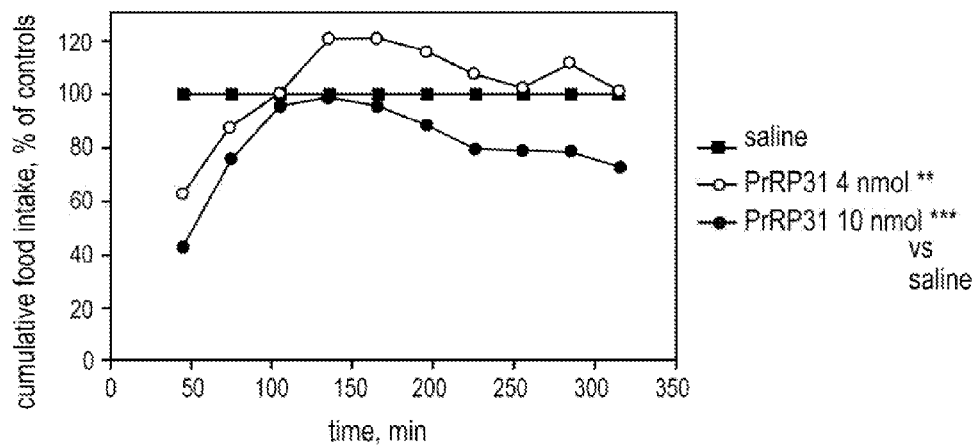
FIG. 1 represents the time course of food intake after ICV administration of PrRP31 in the dose of 4 and 10 nmol/mouse to the fasted C57BL/6 mice. On the x axis is time in minutes, on the y axis, the cumulative food intake as a % of food intake in the control group injected with the saline (n=6-7). The significance is $P<0.01$, *$P<0.001$ versus saline at time points 45 and 75 minutes after injection (one-way ANOVA followed by Dunnett post-hoc test). ■—saline, ○—PrRP31 (4 nmol), ●—PrRP31 (10 nmol).

The neuropeptide PrRP, the prolactin-releasing peptide has been shown to fundamentally affect the regulation of energy metabolism (Hinuma, S., et al. "A prolactin-releasing peptide in the brain," Nature 393:272-276, 1998). There are two forms of PrRP, one composed of 31 amino acids (PrRP31), the other of 20 amino acids (PrRP20) (Hinuma et al.).

PrRP has multiple functions in the body. The first described biological effect was the stimulation of prolactin release (Hinuma et al.). Subsequently it was found, however, that this is not affected in male rats and therefore most likely it is not the primary function of PrRP (Jarry, H., et al., "Prolactin-releasing peptides do not stimulate prolactin release in vivo," Neuroendocrinology, 71:262-267, 2000). Upon finding the PrRP in hypothalamic paraventricular and dorsomedial nuclei (PVN and DMN) which are important for maintaining the metabolic equilibrium, PrRP was considered as a factor affecting food intake (Lawrence, C., at al., "Alternative role for prolactin-releasing peptide in the regulation of food intake," Nat. Neurosci, 3:645-646, 2000).

The anorexigenic effect of PrRP31 was demonstrated when injected into the third brain ventricle where the front wall and base are formed by the hypothalamus (so called intracerebroventricular administration, ICV). It led to significant lowering of food intake and subsequently to a decrease of body weight in rats (Lawrence at al., 2000; Lawrence, C., et al., "Anorectic actions of prolactin-releasing peptide are mediated by corticotrophin-releasing hormone receptors," Am J Physiol Regul Integr Comp Physiol, 286:R101-107, 2004). The decrease in food intake did not affect water consumption or behaviour of the experimental animals. Nausea or anorexia were not demonstrated (Lawrence at al., 2000). It was also found that administration of a shorter peptide, tridecapeptide PrRP13 (containing amino acids 18 to 31 of PrRP31) is not sufficient for maintaining the anorexigenic activity in mice after central administration. (Maixnerová, J., et al., "Characterization of prolactin-releasing peptide: binding, signaling and hormone secretion in rodent pituitary cell lines endogenously expressing its receptor," Peptides, 32:811-817, 2011).

The anorexigenic function of PrRP was also shown in additional experiments. It was found that during negative energy balance, encountered for example during breast feeding or starvation, PrRP gene transcription decreased. The reduced body weight after ICV injection of PrRP is not only the consequence of lower food intake but also of the increased body temperature and oxygen consumption which are indirect measures of increased energy output. There is also an increase in uncoupling protein 1 (UCP-1) mRNA production in the brown adipose tissue which is a further indication of an increased energy output (Ellacott, K., et al., "Repeated administration of the anorectic factor prolactin-releasing peptide leads to tolerance to its effects on energy homeostasis," Am J Physiol Regul Integr Comp Physiol, 285:R1005-1010, 2003).

Genetically modified animals were also used to determine the PrRP function in the body (knock-out (KO) animals with deleted gene coding for PrRP or its receptor GPR10) (Bjursell, M., et al., "GPR10 deficiency in mice results in altered energy expenditure and obesity," *Biochem Biophys Res Commun*, 363:633-638, 2007; Takayanagi, Y., et al., "Endogenous prolactin-releasing peptide regulates food intake in rodents," *J Clin Invest*, 118:4014-4024, 2008). Mice with the deleted PrRP gene suffered from hyperphagia. While the frequency of individual meals was not affected, the amount of each meal increased. Lowering of the energy output was not observed in these mice as body temperature and oxygen consumption are comparable to the control animals (Takayanagi et al.; Mochiduki, A., et al., "Stress response of prolactin-releasing peptide knockout mice as to glucocorticoid secretion," *J Neuroendocrinol*, 22:576-584, 2010).

Similarly, the mice with a deleted gene for the receptor GPR10 had higher food intake leading to obesity, and this effect was more pronounced in the females (Gu, W., et al., "The prolactin-releasing peptide receptor (GPR10) regulates body weight homeostasis in mice," *J Mol Neurosci*, 22:93-103, 2004; Bjursell et al.). The food intake in the GPR10 KO mice was not reduced after the administration of cholecystokinin (CCK). This finding supports the hypothesis that the GPR10-PrRP system may have a key role in the signal transfer of CCK, a peripheral peptide that induces satiety sensation during food intake (Bechtold D, et al., "Prolactin-releasing peptide mediates cholecystokinin-induced satiety in mice," *Endocrinology*, 147:4723-4729, 2006).

From a structural point of view, the presence of arginine in the position 30 is critical for the proper function of PrRP. Its modification or substitution with a different amino acid leads to a loss of binding to the receptor and of biological activity. Furthermore, for the binding of PrRP to the receptor GPR10, the position 31 is important and requires phenylalanine or other amino acid with aromatic moiety bound to at least one $CH_2$ group of the side chain of the amino acid (Boyle, R., et al., "Structure-activity studies on prolactin-releasing peptide (PrRP). Analogues of PrRP-(19-31)-peptide," *J Pept Sci*, 11:161-165, 2005).

For binding experiments with PrRP analogs, the PrRP with $^{125}I$ on the tyrosine in position 20 is used (Satoh, F., et al., "Characterization and distribution of prolactin releasing peptide (PrRP) binding sites in the rat-evidence for a novel binding site subtype in cardiac and skeletal muscle," *Br J Pharmacol*, 129:1787-1793, 2000). It was confirmed the monoiodation of tyrosine does not affect PrRP binding to the receptor (Maixnerová, J., et al., 2011). Modifications of the natural peptide PrRP20 which biological activity in vitro is comparable to PrRP31 (Langmead, C., et al., "Characterization of the binding of [(125)I]-human prolactin releasing peptide (PrRP) to GPR10, a novel G protein coupled receptor," *Br J Pharmacol*, 131:683-688, 2000; Maixnerová et al., 2011) were used in a recent study (Maletínská, L., et al., "Biological properties of prolactin-releasing peptide analogues with a modified aromatic ring of a C-terminal phenylalanine amide," *Peptides*, 32:1887-1892, 2011). C-terminal phenylalanine was replaced by noncoded amino acids, phenylalanine derivatives $PheCl_2$, $PheF_5$ and $PheNO_2$, or by noncoded amino acids with bulky naphtylalanine 1-Nal and 2-Nal, or by tyrosine. All analogs had conserved C-terminal amide which is necessary for biological activity (Hinuma et al.; Roland, B., et al., "Anatomical distribution of prolactin-releasing peptide and its receptor suggests additional functions in the central nervous system and periphery," *Endocrinology*, 140:5736-5745, 1999) and in addition, they were acetylated at the N-terminus of the peptide chain to increase its stability, especially for the in vivo experiments. Biological activity was not dependent on the substitution of amino acids in positions before the C-terminal heptapeptide.

The analogues $[Tyr^{31}]PrRP20$, $[1-Nal^{31}]PrRP20$, $[PheF_5^{31}]PrRP20$, $[PheCl_2^{31}]PrRP20$ and $[PheNO_2^{31}]$PrRP20 bind to the pituitary cell line RC-4B/C which expresses the receptor GPR10 in the order of tens of thousands of binding sites per cell (Maixnerová et al., 2011) with $K_b$ comparable to values for PrRP31 and PrRP20 (Maletínská et al., 2011). In addition, all the analogs increased phosphorylation of enzymes mitogen activated phosphorylase/extracellular-regulated kinase (MAPK/ERK1/2) and the cAMP response element-binding protein (CREB), and stimulated the prolactin release into the medium with $EC_{50}$ comparable to that of PrRP20 (Hinuma et al.). These analogs of PrRP upon ICV administration in the dose of 10 nmol caused statistically significant reduction of food intake in fasted mice (Maletínská et al., 2011). These analogs, therefore, represent very potent anorexigenic peptides which lower food intake when centrally administered, however, not after peripheral administration such as, e.g, subcutaneous, SC, administration.

Provided herein are analogs of the neuropeptides PrRP31 and PrRP20 lipidated by fatty acids (e.g. by myristoyl or palmitoyl) at the N-terminus of the peptide. The lipidated analogs can further possess modified amino acid compositions as described herein. Both types of neuropeptides with different chain length bound to the PrRP receptor with high affinity in in vitro conditions. The lipidated analogs of PrRP20 and PrRP31 significantly increased functionality. The effect was observed in experiments in vitro and in vivo. Advantageously, the lipidated analogs of PrRP20 and PrRP31 demonstrated increased functionality when administered peripherally (e.g, subcutaneously, SC). In particular, peripheral (e.g, subcutaneous, SC) administration of lipidated analogs of PrRP20 and PrRP30 caused a statistically significant reduction of food intake in fasted mice. In fasted mice the lipidated analogs demonstrated a statistically significant dose-dependent reduction in food intake ($P<0.001$) not only after central administration but also after peripheral administration. Furthermore, the effect of lowering food intake was long-lasting and persisted for more than 10 hours after administration. Without being bound by theory, it is thought this is most likely due to increased resistance to degradation by proteases (e.g by introduction of fatty acid and/or noncoded amino acids), and to the binding of lipopeptide to serum albumin. Accordingly, lipidation of PrRP20 and PrRP31 presents a new alternative to deliver these peptides across the blood brain barrier after peripheral administration in order to lower food intake. Furthermore, the lipidated analogs did not induce secretion of prolactin after SC administration to mice and rats in any of the performed tests described herein.

Lipidated Analogs of PrRP20 and PrRP31

Some embodiments disclosed herein include lipidated analogs that are lipidated peptides formed by 20 or 31 amino acids, with the sequence of IRPVGRF-$NH_2$ (SEQ ID NO: 59) at the C-terminus. In this sequence, isoleucine may be substituted by phenylglycine or alanine, and valine may be substituted by phenylglycine. The terminal phenylalanine may be replaced by an amino acid with a side chain containing $CH_2$—Ar or $CH_2$—S—$CH_2$—Ar, where Ar represents phenyl or naphtyl, optionally substituted by a halogen or nitro group. The amino group on the N-terminal amino acid can be serine, diaminopropionic acid or threonine and the C6 to C18 fatty acid is bound by the amide bond. In some embodiments, amino acid substitutions can be made in the lipidated analog. For example, the methionine at position 8 in PrRP31 can be replaced by a norleucine, for example, to increase stability.

In some embodiments, the amino acids in positions before the C-terminal heptapeptide are not essential for the described biological activity of the lipidated analogs. Their substitution by a different amino acid or a slight reduction of their number is possible as long as the resulting lipidated peptide has the binding affinity to the PrRP receptor with $K_i$ in the order of $10^{-6}$ mol·l$^{-1}$ or lower, (or even better $10^{-8}$ mol·l$^{-1}$ or lower), exhibits agonist activity towards PrRP (as determined by MAPK/ERK1/2 signaling in RC-4B/C cells) and the anorexigenic activity, tested by food intake in fasted mice after central and peripheral administration, equal as PrRP or higher.

In some embodiments, the lipidated analogs of PrRP20 or PrRP31 have the general formula J$^1$-J$^2$-rRPsGRt-NH$_2$ (SEQ ID NO: 1)  (I), wherein J$^1$ represents a fatty acid C6 to C18 bound by an amide bond to an amino group of a N-terminal amino acid, J$^2$ represents a chain of 13 or 24 amino acids, r is chosen from isoleucine, alanine, or phenylglycine, s is chosen from valine or phenylglycine, t is chosen from phenylalanine or an amino acid with a side chain containing CH$_2$—Ar or CH$_2$—S—CH$_2$—Ar, where Ar represents phenyl or naphtyl, optionally substituted by halogen or nitro group.

In additional embodiments, the lipidated analogs of PrRP20 or PrRP31 have the general formula J$^1$-k-J$^3$-rRPsGRt-NH$_2$ (SEQ ID NO: 2)  (II), wherein J$^1$ represents a fatty acid C6 to C18 bound by an amide bond to an amino group of a N-terminal amino acid, k is chosen from serine, threonine or diaminopropionic acid, J$^3$ represents a chain of 23 or 12 amino acids, r is chosen from isoleucine, alanine, or phenylglycine, s is chosen from valine or phenylglycine, t is chosen from phenylalanine or an amino acid with a side chain containing CH$_2$—Ar or CH$_2$—S—CH$_2$—Ar, where Ar represents phenyl or naphtyl, optionally substituted by halogen or nitro group.

Yet further embodiments relate to lipidated analogs of PrRP20 or PrRP31 that have the general formula J$^1$-kRmHnHSqEuRTPDINPAWYmoRprRPsGRt-NH$_2$
(SEQ ID NO: 3)  (III), wherein k is chosen from serine, threonine or diaminopropionic acid, m is chosen from threonine, alanine or methylalanine, n is chosen from glutamine or arginine, q is chosen from methionine or norleucine, u is chosen from threonine or isoleucine, o is chosen from glycine or serine, p is chosen from glycine, alanine, proline or N-methylglycine, r is chosen from isoleucine, alanine or phenylglycine, s is chosen from valine or phenylglycine, t is chosen from phenylalanine or an amino acid with side chain containing CH$_2$—Ar or CH$_2$—S—CH$_2$—Ar, where Ar represents phenyl or naphtyl, optionally substituted by halogen or nitro group, J$^1$ represents a fatty acid C6 to C18 bound by the amide bond to the amino group of the N-terminal amino acid, where the chain of amino acids kRmHnHSqEuRTPDINPAWYmoRp (SEQ ID NO: 4) is optionally shortened by eliminating from 1 to 10 amino acids.

Additional embodiments relate to lipidated analogs of PrRP20 or PrRP31 that have the general formula J$^1$-kRmHnHSqEuRTPDINPAWYmoRprRPsGRt-NH$_2$
(SEQ ID NO: 3)  (III)

wherein k is chosen from serine, threonine or diaminopropionic acid, m is chosen from threonine, alanine or methylalanine, n is chosen from glutamine or arginine, q is chosen from methionine or norleucine, u is chosen from threonine or isoleucine, o is chosen from glycine or serine, p is chosen from glycine, alanine, proline or N-methylglycine, r is chosen from isoleucine, alanine or phenylglycine, s is chosen from valine or phenylglycine, t is chosen from phenylalanine or an amino acid with side chain containing CH$_2$—Ar or CH$_2$—S—CH$_2$—Ar, where Ar represents phenyl or naphtyl, optionally substituted by halogen or nitro group, J$^1$ represents a fatty acid C6 to C18 bound by the amide bond to the amino group of the N-terminal amino acid, where the chain of amino acids kRmHnHSqEuRTPDINPAWYmoRp (SEQ ID NO: 4) is optionally shortened from its N-terminal by eliminating from 1 to 10 amino acids.

Further embodiments relate to lipidated analogs of PrRP20 or PrRP31 that have the general formula J$^1$-kRmHnHSqEuRTPDINPAWYmoRprRPsGRt-NH$_2$
(SEQ ID NO: 3)  (III), or J$^1$-TPDINPAWYmoRprRPsGRt-NH$_2$ (SEQ ID NO: 5)  (IV), wherein k is chosen from serine, threonine or diaminopropionic acid, m is chosen from threonine, alanine or methylalanine, n is chosen from glutamine or arginine, q is chosen from methionine or norleucine, u is chosen from threonine or isoleucine, o is chosen from glycine or serine, p is chosen from glycine, alanine, proline or N-methylglycine, r is chosen from isoleucine, alanine or phenylglycine, s is chosen from valine or phenylglycine, t is chosen from phenylalanine or an amino acid with side chain containing CH$_2$—Ar or CH$_2$—S—CH$_2$—Ar, where Ar represents phenyl or naphtyl, optionally substituted by halogen or nitro group, J$^1$ represents a fatty acid C6 to C18 bound by the amide bond to the amino group of the N-terminal amino acid.

Additional embodiments disclosed herein relate to lipidated analogs of PrRP20 or PrRP31 described above where such substitutions of amino acids in positions 1-24 of formula III or in positions 1-13 of formula IV are performed that do not increase the binding affinity value of the resulting lipidated peptide to the receptor GPR10 over $K_i$ $10^{-6}$ mol·l$^{-1}$, measured in the rat pituitary cell line RC-4B/C grown on 24-well plates, which had their bottom coated with polyethyleneimine, up to the optimal density of 300-450 thousand cells per well; then the following agents are added: binding buffer containing 20 mmol·l$^{-1}$ HEPES, pH 7.4, 118 mmol·l$^{-1}$ NaCl, 4.7 mmol·l$^{-1}$ KCl, 5 mmol·l$^{-1}$ MgCl$_2$, 5.5 mmol·l$^{-1}$ glucose, 1 mg/ml bovine serum albumin, 0.1 mg/ml bovine pancreatic trypsin inhibitor; unlabelled analogs of PrRP of final concentration within $10^{-11}$ to $10^{-4}$ mol·l$^{-1}$, and $^{125}$I—PrRP31 of final concentration of $10^{-10}$ mol·l$^{-1}$; the plate is incubated for 60 minutes at room temperature and thereafter the cells are solubilized in 0.1 mol/l solution of NaOH and the radioactivity bound to the cell is counted in the γ-counter.

Further embodiments relate to lipidated analogs of PrRP31 having the general formula J$^1$-SRmHnHSqEuRTPDINPAWYmoRprRPsGRt-NH$_2$
(SEQ ID NO:6)  (V), wherein m is chosen from threonine, alanine or methylalanine, n is chosen from glutamine or arginine, q is chosen from methionine or norleucine, u is chosen from threonine or isoleucine, o is chosen from glycine or serine, p is chosen from glycine, alanine, proline or N-methylglycine, r is chosen from isoleucine, alanine or phenylglycine, s is chosen from valine or phenylglycine, t is chosen from phenylalanine or an amino acid with side chain containing $CH_2$—Ar or $CH_2$—S—$CH_2$—Ar, where Ar represents phenyl or naphtyl, optionally substituted by halogen or nitro group, $J^1$ represents a fatty acid C6 to C18 bound by the amide bond to the amino group of the N-terminal amino acid.

In some embodiments, the lipidated analogs described herein (e.g, the lipidated analogs of formulas I, II, III, IV, and V) include a C-terminal amino acid selected from naphtylalanine, benzylcysteine, benzylhistidine, pentafluorophenyalanine, and nitrophenylalanine.

In additional embodiments, the lipidated analogs described herein (e.g, the lipidated analogs of formulas I, II, III, IV, and V) include a fatty acid is selected from a group that includes fatty acids of 6 to 18, and more preferably, of 13 to 18 carbon atoms. In some embodiments, the lipidated analogs described herein include a fatty acid of 6, 7, 8, 9, 10, 11, 12, 13, 14, 15, 16, 17, or 18 carbon atoms.

Additional embodiments include lipidated analogs selected from the group which includes the following:

(Dpr(oct))RmHnHSNleETRTPDINPAWYmoRGrRPsGRF-NH$_2$ (SEQ ID NO: 7),
(Dpr(dodec))RmHnHSNleETRTPDINPAWYmoRGrRPsGRF-NH$_2$ (SEQ ID NO: 8),
(Dpr(tridec))RmHnHSNleETRTPDINPAWYmoRGrRPsGRF-NH$_2$ (SEQ ID NO: 9),
(Dpr(myr))RmHnHSNleETRTPDINPAWYmoRGrRPsGRF-NH$_2$ (SEQ ID NO: 10),
(Dpr(palm))RmHnHSNleETRTPDINPAWYmoRGrRPsGRF-NH$_2$ (SEQ ID NO: 11),
(myr)TPDINPAWYmoRGrRPsGRF-NH$_2$ (SEQ ID NO: 12),
(palm)TPDINPAWYmoRGrRPsGRF-NH$_2$ (SEQ ID NO: 13),
(Dpr(oct))RmHnHSNleETRTPDINPAWYmoRGrRPsGR 1-Nal-NH$_2$ (SEQ ID NO: 14),
(Dpr(dodec))RmHnHSNleETRTPDINPAWYmoRGrRPsGR 1-Nal-NH$_2$ (SEQ ID NO: 15),
(Dpr(tridec))RmHnHSNleETRTPDINPAWYmoRGrRPsGR 1-Nal-NH$_2$ (SEQ ID NO: 16),
(Dpr(myr))RmHnHSNleETRTPDINPAWYmoRGrRPsGR 1-Nal-NH$_2$ (SEQ ID NO: 17),
(Dpr(palm))RmHnHSNleETRTPDINPAWYmoRGrRPsGR 1-Nal-NH$_2$ (SEQ ID NO: 18),
(myr)TPDINPAWYmoRGrRPsGR 1-Nal-NH$_2$ (SEQ ID NO: 19), and
(palm)TPDINPAWYmoRGrRPsGR 1-Nal-NH$_2$ (SEQ ID NO: 20);

where m is T or A and o is G or S, n is Q or R, r is I, A or phenylglycine, s is V or phenylglycine, Dpr is diaminopropionic acid, 1-Nal is 1-naphtylalanine, Nle is norleucine, myr is myristoyl, palm is palmitoyl, oct is octanoyl, dodec is dodecanoyl, tridec is tridecanoyl. In the peptide positions 1 to 24, such substitutions in amino acids may be performed that do not increase the binding affinity value of the lipidated peptide to the receptor GPR10 over $K_i$ $10^{-6}$ mol·l$^{-1}$, and its anorectic activity evaluated by food intake test in fasted mice after both peripheral and central administration is equal or higher as compared to administered PrRP.

Further embodiments include lipidated analogs selected from the group that includes:

(Dpr(oct))RmHnHSNleETRTPDINPAWYmoRGIRPVGRF-NH$_2$ (SEQ ID NO: 21),
(Dpr(dodec))RmHnHSNleETRTPDINPAWYmoRGIRPVGRF-NH$_2$ (SEQ ID NO: 22),
(Dpr(tridec))RmHnHSNleETRTPDINPAWYmoRGIRPVGRF-NH$_2$ (SEQ ID NO: 23),
(Dpr(myr))RmHnHSNleETRTPDINPAWYmoRGIRPVGRF-NH$_2$ (SEQ ID NO: 24),
(Dpr(palm))RmHnHSNleETRTPDINPAWYmoRGIRPVGRF-NH$_2$ (SEQ ID NO: 25),
(myr)TPDINPAWYmoRGIRPVGRF-NH$_2$ (SEQ ID NO: 26),
(palm)TPDINPAWYmoRGIRPVGRF-NH$_2$ (SEQ ID NO: 27),
(Dpr(oct))RmHnHSNleETRTPDINPAWYmoRGIRPVGR 1-Nal-NH$_2$ (SEQ ID NO: 28),
(Dpr(dodec))RmHnHSNleETRTPDINPAWYmoRGIRPVGR 1-Nal-NH$_2$ (SEQ ID NO: 29),
(Dpr(tridec))RmHnHSNleETRTPDINPAWYmoRGIRPVGR 1-Nal-NH$_2$ (SEQ ID NO: 30),
(Dpr(myr))RmHnHSNleETRTPDINPAWYmoRGIRPVGR 1-Nal-NH$_2$ (SEQ ID NO: 31),
(Dpr(palm))RmHnHSNleETRTPDINPAWYmoRGIRPVGR 1-Nal-NH$_2$ (SEQ ID NO: 32),
(myr)TPDINPAWYmoRGIRPVGR 1-Nal-NH$_2$ (SEQ ID NO: 33), and
(palm)TPDINPAWYmoRGIRPVGR 1-Nal-NH$_2$ (SEQ ID NO: 34);

where m is T or A and o is G or S, n is Q or R, Dpr is diaminopropionic acid, 1-Nal is 1-naphtylalanine, Nle is norleucine, myr is myristoyl, palm is palmitoyl, oct is octanoyl, dodec is dodecanoyl, tridec is tridecanoyl. In the peptide positions 1 to 24, such substitutions in amino acids may be performed that do not increase the binding affinity value of the lipidated peptide to the receptor GPR10 over $K_i$ $10^{-6}$ mol·l$^{-1}$, and its anorexic activity evaluated by food intake test in fasted mice after both peripheral and central administration is equal or higher as compared to administered PrRP.

Some embodiments disclosed herein include lipidated analogs of PrRP20 or PrRP31 selected from the group that includes:

$J^a$-SRAHQHSMETRTPDINPAWYTGRGIRPVGRF-NH$_2$ (SEQ ID NO: 35),
$J^a$-SRTHRHSMEIRTPDINPAWYASRGIRPVGRF-NH$_2$ (SEQ ID NO: 36),
(N-palm)-SRTHRHSMEIRTPDINPAWYASRGIRPVGRF-NHMe (SEQ ID NO: 37),
(N-palm)-SRTHRHSMEIRTPDINPAWYASRGIRPVGRF-NOMe (SEQ ID NO: 38),
(N-myr)-TPDINPAWYTGRGIRPVGRF-NH$_2$, (SEQ ID NO: 39),
(N-myr)-TPDINPAWYASRGIRPVGRF-NH$_2$ (SEQ ID NO: 40),
(N-oct)-TPDINPAWYASRGIRPVGRF-NH$_2$ (SEQ ID NO: 41),
(N-dec)-TPDINPAWYASRGIRPVGRF-NH$_2$ (SEQ ID NO: 42),
(N-dodec)-TPDINPAWYASRGIRPVGRF-NH$_2$ (SEQ ID NO: 43),
$J^{1'}$-SRAHQHS Nle ETRTPDINPAWYTGRGIRPVGRF-NH$_2$ (SEQ ID NO: 44),
$J^a$-SRAHQHS Nle ETRTPDINPAWYTGRGIRPVGR 1-Nal-NH$_2$ (SEQ ID NO: 45),
$J^a$-SRAHQHS Nle ETRTPDINPAWYTGRGIRPVGR PheCl$_2$—NH$_2$ (SEQ ID NO: 46),
$J^a$-SRAHQHS Nle ETRTPDINPAWYTGRGIRPVGR PheNO$_2$—NH$_2$ (SEQ ID NO: 47),
$J^a$-SRAHQHS Nle ETRTPDINPAWYTGRGIRPVGR PheF$_5$—NH$_2$ (SEQ ID NO: 48),
$J^a$-SRAHQHS Nle ETRTPDINPAWYTGRGIRPVGRY-NH$_2$ (SEQ ID NO: 49), J$^a$-SRAHRHS Nle EIRTPDINPAWYASRGIRPVGRY-NH$_2$ (SEQ ID NO: 50),
(N-myr)-Nle-ETRTPDINPAWYTGRGIRPVGRF-NH$_2$ (SEQ ID NO: 51),
(N-myr)-QHSMETRTPDINPAWYTGRGIRPVGRF-NH$_2$ (SEQ ID NO: 52),
(N-myr)-QHSMETRTPDINPAWYASRGIRPVGRF-NH$_2$ (SEQ ID NO: 53), and
(N-palm)SRTHRHSMEIRTPDINPAWYASRGIR-PVGRF-NOMe (SEQ ID NO: 54);
where J$^{1'}$ is chosen from palmitic acid, myristic acid or stearic acid, and J$^a$ is chosen from palmitic acid or myristic acid, wherein N-oct represents N-octanoic acid, N-dec represents N-decanoic acid, N-dodec represents N-dodecanoic acid, N-myr represents N-myristic acid, N-palm represents palmitic acid, wherein each above mentioned fatty acid is always bound by the amide bond to the amino group of the N-terminal amino acid; and wherein Nle represents norleucine, 1-Nal represents naftylalanine, and Me represents methyl.

Some embodiments disclosed herein include a lipidated analog of PrRP20 or PrRP31 or a modified PrRP20 or PrRP31 (e.g., a peptide with an amino acid substitution or reduction) selected from:
(Dpr) RAHQHS Nle ETRTPDINPAWYTGRGIRPVGRF-NH$_2$ (SEQ ID NO: 60),
(Dpr(oct)) RAHQHS Nle ETRTPDINPAWYTGRGIR-PVGRF-NH$_2$ (SEQ ID NO: 61),
(Dpr(dodec)) RAHQHS Nle ETRTPDINPAWYTGRGIR-PVGRF-NH$_2$ (SEQ ID NO: 62),
(Dpr(tridec)) RAHQHS Nle ETRTPDINPAWYTGRGIR-PVGRF-NH$_2$ (SEQ ID NO: 63),
(Dpr(myr)) RAHQHS Nle ETRTPDINPAWYTGRGIR-PVGRF-NH$_2$ (SEQ ID NO: 64),
(Dpr(palm)) RAHQHS Nle ETRTPDINPAWYTGRGIR-PVGRF-NH$_2$ (SEQ ID NO: 65),
(Dpr) RAHQHS Nle ETRTPDINPAWYTGRGIRPVGR 1-Nal-NH$_2$ (SEQ ID NO: 66),
(Dpr(oct)) RAHQHS Nle ETRTPDINPAWYTGRGIR-PVGR 1-Nal-NH$_2$ (SEQ ID NO: 67),
(Dpr(myr)) RAHQHS Nle ETRTPDINPAWYTGRGIR-PVGR 1-Nal-NH$_2$ (SEQ ID NO: 68),
(myr)TPDINPAWYTGRGIRPVGRF-NH$_2$ (SEQ ID NO: 69),
(Dpr) RTHRHS Nle EIRTPDINPAWYASRGIRPVGRF-NH$_2$ (SEQ ID NO: 70),
(Dpr(myr)) RTHRHS Nle EIRTPDINPAWYASRGIR-PVGRF-NH$_2$ (SEQ ID NO: 71),
(myr)TPDINPAWYASRGIRPVGRF-NH$_2$ (SEQ ID NO: 58),
(N-oct) S RAHQHS Nle ETRTPDINPAWYTGRGIR-PVGRF-NH$_2$ (SEQ ID NO: 73),
(N-dec) S RAHQHS Nle ETRTPDINPAWYTGRGIR-PVGRF-NH$_2$ (SEQ ID NO: 74),
(N-dodec) S RAHQHS Nle ETRTPDINPAWYTGRGIR-PVGRF-NH$_2$ (SEQ ID NO: 75),
(N-myr) S RAHQHS Nle ETRTPDINPAWYTGRGIR-PVGRF-NH$_2$ (SEQ ID NO: 76),
(N-palm)S RAHQHS Nle ETRTPDINPAWYTGRGIR-PVGRF-NH$_2$ (SEQ ID NO: 77),
(N-stear)S RAHQHS Nle ETRTPDINPAWYTGRGIR-PVGRF-NH$_2$ (SEQ ID NO: 78),
(N-myr)S RAHQHS Nle ETRTPDINPAWYTGRGIRPVGR 1-Nal-NH$_2$ (SEQ ID NO: 79),
(N-palm)S RAHQHS Nle ETRTPDINPAWYTGRGIR-PVGR 1-Nal-NH$_2$ (SEQ ID NO: 80),
(N-myr)S RAHQHS Nle ETRTPDINPAWYTGRGIRPVGR PheCl$_2$—NH$_2$ (SEQ ID NO: 81),
(N-palm)S RAHQHS Nle ETRTPDINPAWYTGRGIR-PVGR PheCl$_2$—NH$_2$ (SEQ ID NO: 82),
(N-myr)S RAHQHS Nle ETRTPDINPAWYTGRGIRPVGR PheNO$_2$—NH$_2$ (SEQ ID NO: 83),
(N-palm)S RAHQHS Nle ETRTPDINPAWYTGRGIR-PVGR PheNO$_2$—NH$_2$ (SEQ ID NO: 84),
(N-palm)S RAHQHS Nle ETRTPDINPAWYTGRGIR-PVGR PheF$_5$—NH$_2$ (SEQ ID NO: 85),
(N-palm)S RAHQHS Nle ETRTPDINPAWYTGRGIR-PVGR Tyr-NH$_2$ (SEQ ID NO: 86),
(N-myr)TPDINPAWYTGR Sar IRPVGRF-NH$_2$ (SEQ ID NO: 87),
(N-myr)TPDINPAWY N-Me-Ala SRGIRPVGRF-NH$_2$ (SEQ ID NO: 88),
(N-myr)TPDINPAWYTGRGARPFGRF-NH$_2$ (SEQ ID NO: 89),
(N-myr)TPDINPAWYASRPFRPVGRF-NH$_2$ (SEQ ID NO: 90),
(N-myr)Nle-ETRTPDINPAWYTGRGIRPVGRF-NH$_2$ (SEQ ID NO: 91),
(N-myr)QHSMETRTPDINPAWYTGRGIRPVGRF-NH$_2$ (SEQ ID NO: 52),
(N-oct)TPDINPAWYASRGIRPVGRF-NH$_2$ (SEQ ID NO: 41),
(N-dec)TPDINPAWYASRGIRPVGRF-NH$_2$ (SEQ ID NO: 42),
(N-dodec)TPDINPAWYASRGIRPVGRF-NH$_2$ (SEQ ID NO: 43),
(N-myr)TPDINPAWYASRGIRPVGRF-NH$_2$ (SEQ ID NO: 58),
(N-myr)SRTHRHSMEIRTPDINPAWYASRGIRPVGRF-NH$_2$ (SEQ ID NO: 56),
(N-palm)SRTHRHSMEIRTPDINPAWYASRGIRPVGRF-NH$_2$ (SEQ ID NO: 55),
(N-palm)SRTHRHSMEIRTPDINPAWYASRGIRPVGRF-NHMe (SEQ ID NO: 37),
(N-palm)SRTHRHSMEIRTPDINPAWYASRGIRPVGRF-NOMe (SEQ ID NO: 38),
(N-myr)SRAHQHSMETRTPDINPAWYTGRGIRPVGRF-NH$_2$ (SEQ ID NO: 101), and
(N-palm)SRAHQHSMETRTPDINPAWYTGRGIR-PVGRF-NH$_2$ (SEQ ID NO: 102).

Further embodiments disclosed herein include a myristoylated analog selected from:
(Dpr(myr)) RAHQHS Nle ETRTPDINPAWYTGRGIR-PVGRF-NH$_2$ (SEQ ID NO: 64),
(Dpr(myr)) RAHQHS Nle ETRTPDINPAWYTGRGIR-PVGR 1-Nal-NH$_2$ (SEQ ID NO: 68), and
(myr)S RAHQHS Nle ETRTPDINPAWYTGRGIRPVGRF-NH$_2$ (SEQ ID NO: 76).

Additional embodiments disclosed herein include a palmitoylated analog selected from:
(Dpr(palm)) RAHQHS Nle ETRTPDINPAWYTGRGIR-PVGRF-NH$_2$ (SEQ ID NO: 65) and
(palm)S RAHQHS Nle ETRTPDINPAWYTGRGIR-PVGRF-NH$_2$ (SEQ ID NO: 77).

Some embodiments include the stearoylated analog:
(stear)S RAHQHS Nle ETRTPDINPAWYTGRGIR-PVGRF-NH$_2$ (SEQ ID NO: 78).

Further embodiments disclosed herein include the myristoylated analog:
(myr)TPDINPAWYTGRGIRPVGRF-NH2 (SEQ ID NO: 39).

Additional embodiments disclosed herein include a lipidated analog selected from:
(N-myr)TPDINPAWYASRGIRPVGRF-NH$_2$ (SEQ ID NO: 40) and
(N-palm)SRTHRHSMEIRTPDINPAWYASRGIRPVGRF-NH$_2$ (SEQ ID NO: 55).

Some embodiments relate to the use of the lipidated analogs described herein (e.g., the lipidated analogs of formulas I, II, III, IV, and V) as anorexigenic agents which lower food intake after peripheral administration (e.g, subcutaneous administration).

Additional embodiments relate to the use of the lipidated analogs described herein (e.g, the lipidated analogs of formulas I, II, III, IV, and V) for the manufacturing of medication for the treatment of obesity.

Methods of Use

The methods described herein include administering to a subject in need a lipidated analog described herein (e.g., a pharmaceutical composition) containing a therapeutically effective amount of one or more lipidated analogs described herein. Without being bound by theory, the characteristics of the lipidated analogs described herein allow the analogs to be useful for preventing or treating obesity. A mammal can be identified as having or being likely to develop obesity using standard clinical techniques. For example, analysis of a human's family history or eating habits can be used to determine whether or not the human is likely to develop an obesity condition. As described herein, a mammal identified as having or being susceptible to developing an obesity condition can be treated by administering a lipidated analog disclosed herein.

Pharmaceutical Compositions, Routes of Administration, and Dosing

Provided herein, in certain embodiments, are pharmaceutical compositions comprising at least one lipidated analog as described herein.

Pharmaceutical compositions are typically formulated using one or more physiologically acceptable carriers including excipients and auxiliaries which facilitate processing of the therapeutic composition into preparations which are used pharmaceutically. Proper formulation is dependent upon the route of administration chosen. A summary of pharmaceutical compositions is found, for example, in Remington: The Science and Practice of Pharmacy, Nineteenth Ed (Ea hston, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999).

Provided herein are pharmaceutical compositions that include one or more lipidated analogs described herein and one or more pharmaceutically acceptable diluent(s), excipient(s), or carrier(s). In addition, the lipidated analog is optionally administered as pharmaceutical compositions in which it is mixed with other active ingredients, as in combination therapy. In some embodiments, the pharmaceutical composition includes other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions can also contain other therapeutically valuable substances.

A pharmaceutical composition, as used herein, refers to a mixture of a lipidated analog with one or more other chemical components, such as carriers, stabilizers, diluents, dispersing agents, suspending agents, thickening agents, and/or excipients. The pharmaceutical composition facilitates administration of the lipidated analog to an organism. In practicing the methods of treatment or use provided herein, a lipidated analog is administered in a pharmaceutical composition to a mammal having a condition, disease, or disorder to be treated. Preferably, the mammal is a human. The dose and dosing regimen varies depending on the severity and stage of the condition, the age and relative health of an individual, the potency of the therapeutic composition used and other factors. The lipidated analog is optionally used singly or in combination with one or more therapeutic agents as components of mixtures.

The pharmaceutical compositions described herein can be formulated, for example, as aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations. The pharmaceutical formulations described herein are optionally administered to a individual by one or more administration routes, including but not limited to, parenteral (e.g., intravenous, subcutaneous, intramuscular, intrathecal), intracerebroventricular, intranasal, buccal, topical, rectal, oral, or transdermal administration routes.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

The following specific and non-limiting examples are to be construed as merely illustrative, and do not limit the present disclosure in any way whatsoever. Without further elaboration, it is believed that one skilled in the art can, based on the description herein, utilize the present disclosure to its fullest extent.

The following abbreviations are used herein: analysis of variance (ANOVA); bovine serum albumin (BSA); bovine pancreatic trypsin inhibitor (BPTI); epidermal growth factor (EGF); 4-(2-hydroxyethyl)-1-piperazineethansulfonic acid (HEPES); phosphate buffer saline (PBS); sodium dodecyl sulfate (SDS); Tris-buffered saline (TBS); diaminopropionic acid (Dpr); 1-naphtylalanine (1-Nal); norleucine (Nle); myristoyl (myr); palmitoyl (palm); octanoyl (oct); dodecanoyl (dodec); and tridecanoyl (tridec).

Example 1: Synthesis of the PrRP Peptides and PrRP Analogs

The peptides were synthesized using the method of solid phase synthesis according to Maixnerová et al. (Maixnerová, J., et al., "Structure-activity relationship of CART (cocaine- and amphetamine-regulated transcript) peptide fragments," *Peptides*, 28:1945-1953, 2007) utilizing the Fmoc strategy on the ABI 433A synthesizer (Applied Biosystems, Foster City, Calif., USA). Lipidation with the appropriate fatty acid was performed before cleaving the peptide off the resin as reported in Maletínská, L., et al., "Characterization of new stable ghrelin analogs with prolonged orexigenic potency," *J Pharmacol Exp Ther*, 340:781-786, 2012.

The peptide PrRP31 was iodinated with $Na^{125}I$ using Iodo-Gen (Pierce, Rockford, Ill., USA) according to the published procedure (Maixnerová et al., 2011). Monoiodinated peptide was stored in aliquots at −20° C. and was used up in binding assays within one month.

Table 1 describes the structures of PrRP31, PrRP20, and analogs of PrRP31 and PrRP20 synthesized:

TABLE 1

Structures of PrRP31, PrRP20, and lipidated analogs of PrRP31 and PrRP20

Rat PrRP31 and lipidated PrRP31 analogs

PrRP31 SRAHQHSMETRTPDINPAWYTGRGIRPVGRF-NH$_2$ (SEQ ID NO: 106)
| | |
|---|---|
| 1 | (Dpr) RAHQHS Nle ETRTPDINPAWYTGRGIRPVGRF-NH$_2$ (SEQ ID NO: 60) |
| 2 | (Dpr(oct)) RAHQHS Nle ETRTPDINPAWYTGRGIRPVGRF-NH$_2$ (SEQ ID NO: 61) |
| 3 | (Dpr(dodec)) RAHQHS Nle ETRTPDINPAWYTGRGIRPVGRF-NH$_2$ (SEQ ID NO: 62) |
| 4 | (Dpr(tridec)) RAHQHS Nle ETRTPDINPAWYTGRGIRPVGRF-NH$_2$ (SEQ ID NO: 63) |
| 5 | (Dpr(myr)) RAHQHS Nle ETRTPDINPAWYTGRGIRPVGRF-NH$_2$ (SEQ ID NO: 64) |
| 6 | (Dpr(palm)) RAHQHS Nle ETRTPDINPAWYTGRGIRPVGRF-NH$_2$ (SEQ ID NO: 65) |
| 7 | (Dpr) RAHQHS Nle ETRTPDINPAWYTGRGIRPVGR 1-Nal-NH$_2$ (SEQ ID NO: 66) |
| 8 | (Dpr(oct)) RAHQHS Nle ETRTPDINPAWYTGRGIRPVGR 1-Nal-NH$_2$ (SEQ ID NO: 67) |
| 9 | (Dpr(myr)) RAHQHS Nle ETRTPDINPAWYTGRGIRPVGR 1-Nal-NH$_2$ (SEQ ID NO: 68) |

Rat PrRP20 and lipidated PrRP20 analog

| Analog no. | Sequence |
|---|---|
| PrRP20 | TPDINPAWYTGRGIRPVGRF-NH$_2$ (SEQ ID NO: 107) |
| 10 | (myr) TPDINPAWYTGRGIRPVGRF-NH$_2$ (SEQ ID NO: 39) |

Human PrRP31 lipidated PrRP31 and PrRP20 analogs:

| Analog no. | Sequence |
|---|---|
| hPrRP31 | SRTHRHSMEIRTPDINPAWYASRGIRPVGRF-NH$_2$ (SEQ ID NO: 125) |
| 11 | (Dpr) RTHRHS Nle EIRTPDINPAWYASRGIRPVGRF-NH$_2$ (SEQ ID NO: 70) |
| 12 | (Dpr(myr)) RTHRHS Nle EIRTPDINPAWYASRGIRPVGRF-NH$_2$ (SEQ ID NO: 71) |
| 13 | (myr) TPDINPAWYASRGIRPVGRF-NH$_2$ (SEQ ID NO: 40) |

Other rat and human PrRP peptides and lipidated PrRP31 and PrRP20 analogs tested:

| Analog no. | Sequence |
|---|---|
| 14 | S RAHQHS Nle ETRTPDINPAWYTGRGIRPVGRF-NH$_2$, (SEQ ID NO: 109) |
| 15 | (N-oct) S RAHQHS Nle ETRTPDINPAWYTGRGIRPVGRF-NH$_2$ (SEQ ID NO: 73) |
| 16 | (N-dec) S RAHQHS Nle ETRTPDINPAWYTGRGIRPVGRF-NH$_2$ (SEQ ID NO: 74) |
| 17 | (N-dodec) S RAHQHS Nle ETRTPDINPAWYTGRGIRPVGRF-NH$_2$ (SEQ ID NO: 75) |
| 18 | (N-myr) S RAHQHS Nle ETRTPDINPAWYTGRGIRPVGRF-NH$_2$ (SEQ ID NO: 76) |
| 19 | (N-palm) S RAHQHS Nle ETRTPDINPAWYTGRGIRPVGRF-NH$_2$ (SEQ ID NO: 77) |
| 20 | (N-stear) S RAHQHS Nle ETRTPDINPAWYTGRGIRPVGRF-NH$_2$ (SEQ ID NO: 78) |
| 21 | S RAHQHS Nle ETRTPDINPAWYTGRGIRPVGR 1-Nal-NH$_2$ (SEQ ID NO: 110) |
| 22 | (N-myr) S RAHQHS Nle ETRTPDINPAWYTGRGIRPVGR 1-Nal-NH$_2$ (SEQ ID NO: 79) |
| 23 | (N-palm) S RAHQHS Nle ETRTPDINPAWYTGRGIRPVGR 1-Nal-NH$_2$ (SEQ ID NO: 80) |
| 24 | S RAHQHS Nle ETRTPDINPAWYTGRGIRPVGR PheCl$_2$ -NH$_2$ (SEQ ID NO: 111) |
| 25 | (N-myr) S RAHQHS Nle ETRTPDINPAWYTGRGIRPVGR PheCl$_2$ -NH$_2$ (SEQ ID NO: 81) |
| 26 | (N-palm) S RAHQHS Nle ETRTPDINPAWYTGRGIRPVGR PheCl$_2$ -NH$_2$ (SEQ ID NO: 82) |
| 27 | S RAHQHS Nle ETRTPDINPAWYTGRGIRPVGR PheNO2-NH$_2$ (SEQ ID NO: 112) |
| 28 | (N-myr) S RAHQHS Nle ETRTPDINPAWYTGRGIRPVGR PheNO$_2$-NH$_2$ (SEQ ID NO: 83) |
| 29 | (N-palm) S RAHQHS Nle ETRTPDINPAWYTGRGIRPVGR PheNO$_2$-NH$_2$ (SEQ ID NO: 84) |
| 30 | SHQRPADTHWYPRG Nle FPTIGRITARNGEVSR (SEQ ID NO: 113) |
| 31 | (N-myr) SHQRPADTHWYPRG Nle FPTIGRITARNGEVSR (SEQ ID NO: 114) |
| 32 | S RAHQHS Nle ETRTPDINPAWYTGRGIRPVGR PheF$_5$ -NH$_2$ (SEQ ID NO: 115) |
| 33 | (N-palm) S RAHQHS Nle ETRTPDINPAWYTGRGIRPVGR PheF$_5$ -NH$_2$ (SEQ ID NO: 85) |
| 34 | S RAHQHS Nle ETRTPDINPAWYTGRGIRPVGR Tyr-NH$_2$ (SEQ ID NO: 116) |
| 35 | (N-palm) S RAHQHS Nle ETRTPDINPAWYTGRGIRPVGR Tyr-NH$_2$ (SEQ ID NO: 86) |
| 36 | f r GVPRIGRGTYWAPNIDPT-NH$_2$ (SEQ ID NO: 117) |
| 37 | (N-myr) f r GVPRIGRGTYWAPNIDPT-NH$_2$ (SEQ ID NO: 118) |
| 38 | TPDINPAWYTGR Sar IRPVGRF-NH$_2$ (SEQ ID NO: 119) |
| 39 | (N-myr) TPDINPAWYTGR Sar IRPVGRF-NH$_2$ (SEQ ID NO: 87) |
| 40 | TPDINPAWY N-Me-Ala SRGIRPVGRF-NH$_2$ (SEQ ID NO: 120) |
| 41 | (N-myr) TPDINPAWY N-Me-Ala SRGIRPVGRF-NH$_2$ (SEQ ID NO: 88) |

TABLE 1-continued

Structures of PrRP31, PrRP20, and lipidated analogs of PrRP31 and PrRP20

| | | |
|---|---|---|
| 42 | TPDINPAWYTGRGARPFGRF-NH$_2$ | (SEQ ID NO: 121) |
| 43 | (N-myr)TPDINPAWYTGRGARPFGRF-NH$_2$ | (SEQ ID NO: 89) |
| 44 | TPDINPAWYASRPFRPVGRF-NH$_2$ | (SEQ ID NO: 122) |
| 45 | (N-myr)TPDINPAWYASRPFRPVGRF-NH$_2$ | (SEQ ID NO: 90) |
| 46 | Nle-ETRTPDINPAWYTGRGIRPVGRF-NH$_2$ | (SEQ ID NO: 123) |
| 47 | (N-myr)Nle-ETRTPDINPAWYTGRGIRPVGRF-NH$_2$ | (SEQ ID NO: 91) |
| 48 | QHSMETRTPDINPAWYTGRGIRPVGRF-NH$_2$ | (SEQ ID NO: 124) |
| 49 | (N-myr)QHSMETRTPDINPAWYTGRGIRPVGRF-NH$_2$ | (SEQ ID NO: 52) |
| 50 | SRTHRHSMEIRTPDINPAWYASRGIRPVGRF-NH$_2$ | (SEQ ID NO: 125) |
| 51 | TPDINPAWYASRGIRPVGRF-NH$_2$ | (SEQ ID NO: 126) |
| 52 | (N-oct)TPDINPAWYASRGIRPVGRF-NH$_2$ | (SEQ ID NO: 41) |
| 53 | (N-dec)TPDINPAWYASRGIRPVGRF-NH$_2$ | (SEQ ID NO: 42) |
| 54 | (N-dodec)TPDINPAWYASRGIRPVGRF-NH$_2$ | (SEQ ID NO: 43) |
| 55 | (N-myr)TPDINPAWYASRGIRPVGRF-NH$_2$ | (SEQ ID NO: 40) |
| 56 | (N-myr)SRTHRHSMEIRTPDINPAWYASRGIRPVGRF-NH$_2$ | (SEQ ID NO: 56) |
| 57 | (N-palm)SRTHRHSMEIRTPDINPAWYASRGIRPVGRF-NH$_2$ | (SEQ ID NO: 55) |
| 58 | (N-palm)SRTHRHSMEIRTPDINPAWYASRGIRPVGRF-NHMe | (SEQ ID NO: 37) |
| 59 | (N-palm)SRTHRHSMEIRTPDINPAWYASRGIRPVGRF-NOMe | (SEQ ID NO: 38) |
| 60 | (N-myr)SRAHQHSMETRTPDINPAWYTGRGIRPVGRF-NH$_2$ | (SEQ ID NO: 101) |
| 61 | (N-palm)SRAHQHSMETRTPDINPAWYTGRGIRPVGRF-NH$_2$ | (SEQ ID NO: 102) |

Example 2: Competitive Binding Experiments

Competitive binding experiments were performed according to Motulsky and Neubig (Motulsky, A., et al., "Analyzing radioligand binding data," *Curr Protoc Neurosci*, Chapter 7, Unit 7.5, 2002).

Binding experiments were conducted with rat pituitary cells and CHO cells as follows:

The rat pituitary cell line RC-4B/C (ATCC, Manassas, USA) was grown on 24-well plates which had their bottom coated with polyethyleneimine. The cells were grown to the optimal density of 300-450 thousand per well. The following agents were used for the experiment: binding buffer (20 mmol·l$^{-1}$ HEPES, pH 7.4; 118 mmol·l$^{-1}$ NaCl, 4.7 mmol·l$^{-1}$ KCl, 5 mmol·l$^{-1}$ MgCl$_2$, 5.5 mmol·l$^{-1}$ glucose, 1 mg/ml BSA, 0.1 mg/ml BPTI), unlabelled analogs of PrRP of final concentration within $10^{-11}$ to $10^{-4}$ mol·l$^{-1}$, and rat $^{125}$I—PrRP31 of final concentration of $10^{-10}$ mol·l$^{-1}$ (Maixnerová et al., 2011).

CHO cells with transfected human PrRP receptor, GPR10 (Perkin Elmer, USA) were grown on 24-well plates coated with polyethyleneimine. The cells were grown to the optimal density of 40-80 thousand cells per well. The following agents were used for the experiment: binding buffer (25 mmol·l$^{-1}$ Tris, pH 7.4; 118 mmol·l$^{-1}$ NaCl, 10 mmol·l$^{-1}$ MgCl$_2$, 1 mmol·l$^{-1}$ CaCl$_2$, 5.5 mmol·l$^{-1}$ glucose, 0.5 mg/ml BSA), unlabelled analogs of PrRP of final concentration within $10^{-11}$ to $10^{-4}$ mol·l$^{-1}$, and human $^{125}$I—PrRP31 of final concentration of $5\times10^{-11}$ mol·l$^{-1}$.

Plates were incubated for 60 minutes at room temperature. After incubation, the cells were solubilized in 0.1 mol/l solution of NaOH and the radioactivity bound to the cells was counted using a γ-counter. The experiments were performed in duplicate and repeated at least three times.

All the tested rat and human PrRP analogs (for structures, see Table 1), the lipidated peptides, bound with high affinity to the rat receptor in RC-4B/C cells (Table 2, 5) and the human receptor GPR10 in CHO cells (Table 5) (on the order of nmol·l$^{-1}$). With the lengthening of the fatty acid chain, the value of K$_i$ decreased, indicating the affinity was stronger with the lipidated PrRP analogs, up to an order of magnitude as compared to the original unlipidated peptide (see Table 2, 5).

The results indicate the lipidation of the tested peptides led to the increase in receptor binding and the lipidated analogs lowered the Ki in binding to rat RC-4B/C cells and human GPR10 receptor in correlation with the chain length of the fatty acid present on the lipidated analog. The addition of fatty acid not only preserved receptor binding (as a result of N-terminal lipidation, whereas the receptor binding depends on the C-terminal RF-amide), it increased the binding affinity by up to an order of magnitude.

Human lipidated PrRP analogs (for structures, see Table 1, analog nos: 11-13) displaced to a similar extent the binding of both the rat and human $^{125}$I—PrRP to the RC-4B/C cells with the rat PrRP receptor and human GPR10 receptor in the nmol·l$^{-1}$ range (see Table 3). Lipidized shortened PrRP31 analogs (21-30 amino acids, C-terminal heptapeptide preserved) showed binding afinities similar to both native forms of PrRP.

For evaluation of competitive binding experiments, the program Graph Pad Prism Software (San Diego, Calif., USA) was used. A method of nonlinear regression assuming one-site binding was used. The value of K$_i$ was calculated using the equation of Cheng and Prussof (Cheng, Y., et al., "Relationship between the inhibition constant (K1) and the concentration of inhibitor which causes 50 percent inhibition (I50) of an enzymatic reaction," *Biochem Pharmacol*, 22:33099-3108, 1973), using the value of K$_d$ 4.21 nmol·l$^{-1}$ and concentration of radioligand was 0.1 nmol·l$^{-1}$ (Maixnerová et al., 2011).

Example 3: Cellular Signaling

RC-4B/C cells, which were used to determine if lipidated PrRP20 analogs are able to initiate the MAPK/ERK1/2 signaling pathway, were grown in 6-well plates up to the optimal density of 700-900 cells per well. Seventeen hours before sample harvest, the growth medium was replaced by a serum-free medium lacking epidermal growth factor (EGF). The respective lipidated PrRP analog was added to each well in the final concentration of $10^{-6}$ mol·l$^{-1}$. After a 5 minute incubation at 37° C., the plate was placed on ice and each well was rinsed three times with PBS pH 7.4 (137 mmol·l$^{-1}$ NaCl, 2.7 mmol·l$^{-1}$ KCl, 8 mmol·l$^{-1}$ Na$_2$HPO$_4$.2H$_2$O a 1.76 mmol·l$^{-1}$ KH$_2$PO$_4$) and cooled to 4° C. The cells were then solubilized in a sample buffer (62.5 mmol·l$^{-1}$ Tris-HCl pH 6.8, 10% glycerol, 2% SDS, 0.01% bromophenol blue, 5% merkaptoethanol, 50 mmol·l$^{-1}$ NaF and 1 mmol·l$^{-1}$ Na$_3$VO$_4$), and collected into microtubes and frozen at −20° C. Samples were collected in at least three independent experiments.

To determine if the lipidated PrRP20 analogs initiated the MAPK/ERK1/2 signaling pathway, Western blot analysis was used. Electrophoresis was performed on 5%/12% polyacrylamide gel in the presence of SDS (SDS-PAGE) on the instrument MiniProtean 3 (BioRad, Herkules, Calif., USA). Samples that were loaded on the gel were first disintegrated by ultrasound, then heated at 100° C. for 2 minutes, and centrifuged for 5 minutes at 500×g at room temperature. PrRP20, which was shown to initiate MAPK/ERK1/2 signaling (Maixnerová et al., 2011), was used as a positive control. Electrophoresis was performed at a constant voltage of 100 V for 10 minutes, or for 60 minutes at 150 V.

To show the presence of phosphorylated proteins in the samples, the proteins from the SDS-PAGE gel were transferred to the Immobilon™-P PVDF (polyvinylidene difluoride) membrane (Sigma-Aldrich, USA). The transfer was performed in blotting buffer at pH 8.3 (25 mmol·l$^{-1}$ Tris, 192 mmol·l$^{-1}$ glycine and 20% methanol) for 20 hours at 4° C. at a constant voltage of 30 V.

After the protein transfer to the PVDF membrane, the membranes were washed for 5 minutes in TBS washing buffer (20 mmol·l$^{-1}$ Tris, 140 mmol·l$^{-1}$ NaCl and 0.1% Tween-20) and then incubated for 1 hour in blocking buffer (TBS with 5% non-fat milk powder and 5 mmol·l$^{-1}$ Na$_3$VO$_4$ and 50 mmol·l$^{-1}$ NaF) at room temperature. Further, the membranes were washed three times for 5 minutes using the TBS washing buffer. The membranes were then incubated with the primary antibody against phospho-p44/42 MAPK (Thr202/Tyr204) (Cell Signaling Technology, Beverly, USA) which was diluted in blocking buffer at 1:1000. After the next three washes with the TBS washing buffer for 5 minutes, the membranes were incubated for 1 hour with rabbit secondary antibody labeled with peroxidase (Sigma, St. Louis, USA) which was diluted in blocking buffer at 1:12,000.

The membranes were then washed three times in TBS washing buffer for 5 minutes and then the solution Femto (Pierce SuperSignal, Thermo Fisher Scientific, Rockford, Ill., USA) was applied. The induced chemiluminiscence was detected by a CCD camera (LAS 3000, Fuji Photo Film GmBH, Düsseldorf, Germany).

To assess the initiation of signaling pathways, a densitometric analysis using the program Quantity One (BioRad, Hercules, Calif., USA) was used. For statistical evaluation of the statistically significant response of the cellular signaling, one-way ANOVA with subsequent Dunnett post-hoc test was used. Data was statistically significant at P<0.05.

The results of the MAPK/ERK1/2 signaling analysis are shown in Table 2.

TABLE 2

The affinity of lipidated peptidic analogs of the rat PrRP31 and PrRP20 to the rat receptor, and biological activity in RC-4B/C cells.

| | $^{125}$I-rat PrRP31 | | |
| --- | --- | --- | --- |
| Analog | K$_i$ (nM) | % of PrRP31 binding | ERK signaling |
| PrRP31 | 4.93 ± 0.61 | 100 | agonist |
| 1 | 3.74 ± 0.29 | 132 | agonist |
| 2 | 2.86 ± 0.17 | 172 | agonist |
| 3 | 1.12 ± 0.12 | 440 | agonist |
| 4 | 0.51 ± 0.03 | 967 | agonist |
| 5 | 0.82 ± 0.13 | 601 | agonist |
| 6 | 0.46 ± 0.06 | 1072 | agonist |
| 7 | 60.07 ± 2.10 | 8 | agonist |
| 8 | 39.24 ± 2.71 | 13 | agonist |

TABLE 2-continued

The affinity of lipidated peptidic analogs of the rat PrRP31 and PrRP20 to the rat receptor, and biological activity in RC-4B/C cells.

| | $^{125}$I-rat PrRP31 | | |
| --- | --- | --- | --- |
| Analog | K$_i$ (nM) | % of PrRP31 binding | ERK signaling |
| 9 | 2.95 ± 0.62 | 167 | agonist |
| PrRP20 | 3.44 ± 0.85 | 143 | agonist |
| 10 | 0.78 ± 0.45 | 632 | agonist |

All of the tested lipidated peptides displayed a positive result for signaling in RC-4B/C cells which was comparable or higher to the effect of PrRP31. All of the lipidated peptides were therefore agonists in vitro.

TABLE 3

Affinity of lipidated analogs of rat and human PrRP to the rat receptor in RC-4B/C cells

| Analog | $^{125}$I-rat PrRP31 Ki (nM) | $^{125}$I-human PrRP31 Ki (nM) |
| --- | --- | --- |
| hPrRP31 | 1.54 ± 0.42 | 3.01 ± 0.70 |
| 11 | 2.28 ± 1.30 | 2.00 ± 1.26 |
| 12 | 4.13 ± 2.57 | 3.16 ± 0.83 |
| 13 | 0.41 ± 0.13 | 0.66 ± 0.14 |

Table 2 and 3: The values of the inhibition constant K$_i$ were calculated from IC$_{50}$ using Cheng and Prusoff's equation (for K$_d$ the value 4.21 nmol·l$^{-1}$ found in the saturation binding experiments was used and the concentration of the radioligand was 0.1 nmol·l$^{-1}$ with relevant values of S.E.M.

Example 4. Test of Food Intake after SC or ICV Administration of Lipidated PrRP Analogs Male C57BL/6 mice (An Lab, Prague 4) were bred in the accredited animal facility in the Institute of Organic Chemistry and Biochemistry, Czech Academy of Sciences, Prague, at the Institute of Molecular Genetics, Prague 4, at the temperature of 22±2° C. with access to food and water ad libitum. The day/night cycle was 12/12 hours (light turned on at 6:00 am). Animals were treated according to the Animal Protection Act (Act No. 246/1992). The males were fed standard chow diet St-1 (Mlýn Kocanda, Praha, Czech Republic) which contained 66% saccharides, 25% proteins and 9% lipids with a caloric value of 3.4 kcal/g.

The food was withdrawn 17 hours prior to injection of lipidated peptide and free access to water was maintained. The administration of saline, PrRP or lipidated analogs was performed either by SC injection at doses of 1-10 mg/kg (volume 0.2 ml/mouse), or by ICV using infusion pump (cannulae were inserted into the third brain ventricle 4 days before the experiment following the procedure of Maixnerová et al. (Maixnerová et al., 2011)). The single dose of peptide was 4 nmol/mouse (5 μl/mouse).

Fifteen minutes after the lipidated peptide administration, the mice were given pre-weighed food. The food was then weighed every 30 minutes for 5-10 hours. The administration of every dose was performed at least twice and one group of mice consisted of at least 6 mice. The results were presented as % of food intake as compared with the control group injected with saline.

Statistical evaluation was performed using program Graph-Pad Prism Software (San Diego, Calif., USA), and the one-way ANOVA with a subsequent Dunnettovým post-hoc test. The difference in food intake between mice injected with saline and mice injected with the examined peptide were considered statistically significant at P<0.05.

The results are summarized in Table 4 and 5 and FIGS. 1-6.

TABLE 4

Biological activity of lipidated peptides - rat PrRP analogs in vivo

| | SC administration | | | | ICV administration | | | |
|---|---|---|---|---|---|---|---|---|
| | 45 minutes | | 300 minutes | | 45 minutes | | 300 minutes | |
| Analog | food intake (g) | % control | food intake (g) | % control | food intake (g) | % control | food intake (g) | % control |
| PrRP31 | 0.32 | 100 | 1.15 | 105 | 0.42 | 75 | 1.37 | 104 |
| 1 | 0.38 | 117 | 1.05 | 97 | 0.39 | 70 | 0.71 | 53 |
| 3 | 0.12 | 50 | 0.61 | 60 | | NT | | |
| 4 | 0.07 | 30 | 1.04 | 101 | 0.38 | 71 | 1.4 | 105 |
| 5 | 0.05 | 25 | 0.18 | 21 | 0.35 | 62 | 0.96 | 73 |
| 6 | 0 | 0 | 0.14 | 14 | 0.38 | 71 | 1.3 | 100 |
| 7 | 0.16 | 49 | 0.88 | 81 | | NT | | |
| 8 | 0.17 | 76 | 0.78 | 90 | 0.34 | 60 | 1.05 | 79 |
| 9 | 0.01 | 2 | 0.22 | 25 | 0.28 | 51 | 1.03 | 78 |
| PrRP20 | 0.32 | 100 | 1.1 | 100 | 0.32 | 68 | 1.29 | 100 |
| 10 | 0.11 | 32 | 44 | 44 | 0.28 | 51 | 1.1 | 86 |

The food intake was evaluated at 300 minutes after administration of the compound. At 45 minutes after administration, the effect was at the maximum. Compounds 1, 2, 5, 7, 9 were administered at the dose of 10 mg/kg, and compounds 3, 4, 6, 10 were administered at the dose of 5 mg/kg (SC administration). NT indicates not tested.

TABLE 5

Competitive binding to rat RC-4B/C cells and CHO cells with transfected human GPR10 receptor and food intake in fasted C57BL/6 mice (5 mg/kg SC)

| Analog no. | C-4B/C cells $^{125}$I-rat PrRP31 $K_i$ (nM) | GPR10 receptor in CHO cells $K_i$ (nM) | Food intake in mice (5 mg/kg SC) % saline-treated group (45 min) |
|---|---|---|---|
| 14 | 1.28 ± 0.2 | 1.92 ± 0.43 | 100 |
| 15 | 0.98 ± 0.22 | 1.53 ± 0.07 | 94 |
| 16 | 0.65 ± 0.41 | 1.46 ± 0.57 | 57 |
| 17 | 0.39 ± 0.14 | 1.19 ± 0.36 | 22 |
| 18 | 0.69 ± 0.09 | 0.71 ± 0.09 | 3 |
| 19 | 0.51 ± 0.16 | 3.03 ± 0.34 | 2 |
| 20 | 0.96 ± 0.10 | 5.39 ± 0.58 | 3.5 |
| 21 | 102 ± 19.1 | 34.52 ± 16.00 | NT |
| 22 | 3.96 ± 1.22 | 1.33 ± 0.22 | NT |
| 23 | 2.17 ± 1.29 | 4.27 ± 0.77 | 13 |
| 24 | 3.84 ± 0.93 | 2.27 ± 0.48 | NT |
| 25 | 1.79 ± 1.02 | 0.95 ± 0.33 | 13 |
| 26 | 1.30 ± 0.29 | 1.05 ± 0.41 | 5 |
| 27 | 19.90 ± 5.9 | 4.80 ± 0.88 | NT |
| 28 | 1.97 ± 1.26 | 1.59 ± 1.05 | NT |
| 29 | 0.58 ± 0.10 | 0.77 ± 0.28 | 0.7 |
| 30 | 1317000 ± 1259000 | >10$^7$ | NT |
| 31 | 123 ± 16.1 | 262.0 ± 55.4 | 100 |
| 32 | 9.69 ± 1.86 | 8.59 ± 1.20 | NT |
| 33 | 0.51 ± 0.08 | 1.92 ± 0.53 | 41 |
| 34 | 3.25 ± 0.15 | 2.02 ± 0.09 | NT |
| 35 | 0.44 ± 0.22 | 1.57 ± 0.39 | 22 |
| 36 | 5200 ± 420 | 6290 ± 3970 | NT |
| 37 | 364 ± 83 | >10$^7$ | 100 |
| 38 | 7.94 ± 3.74 | 4.51 ± 1.49 | NT |
| 39 | 0.32 ± 0.07 | 3.12 ± 0.37 | NT |
| 40 | 49.4 ± 9.35 | 8.72 ± 2.22 | NT |
| 41 | 0.46 ± 0.05 | 2.10 ± 0.77 | NT |
| 42 | 655 ± 164 | 583 ± 293 | NT |
| 43 | 7.21 ± 0.71 | 8.47 ± 3.18 | NT |
| 44 | 2.14 ± 0.53 | 1.73 ± 0.22 | NT |
| 45 | 0.84 ± 0.17 | 0.58 ± 0.26 | NT |
| 46 | 2.94 ± 0.62 | 3.44 ± 0.48 | NT |
| 47 | 0.45 ± 0.04 | 5.48 ± 0.64 | NT |
| 48 | 2.61 ± 0.15 | 5.92 ± 0.76 | NT |
| 49 | 0.37 ± 0.11 | 6.93 ± 4.74 | NT |
| 50 | 1.78 ± 0.46 | 8.70 ± 1.56 | 100 |
| 51 | 2.38 ± 0.19 | 4.53 ± 0.80 | 100 |
| 52 | NT | 3.02 ± 0.49 | 100 |
| 53 | NT | 2.41 ± 0.26 | 100 |
| 54 | NT | 2.41 ± 0.26 | 85 |
| 55 | 0.48 ± 0.18 | 4.33 ± 0.25 | 10 |
| 56 | 0.95 ± 0.35 | NT | 35 |
| 57 | 0.28 ± 0.80 | 4.71 ± 0.56 | 11 |
| 58 | NT | 3.16 ± 0.51 | NT |
| 59 | NT | 4.21 ± 0.55 | NT |
| 60 | 0.75 ± 0.10 | NT | 20 |
| 61 | 0.41 ± 0.12 | NT | 2 |

NT—not-tested

Figure 2:
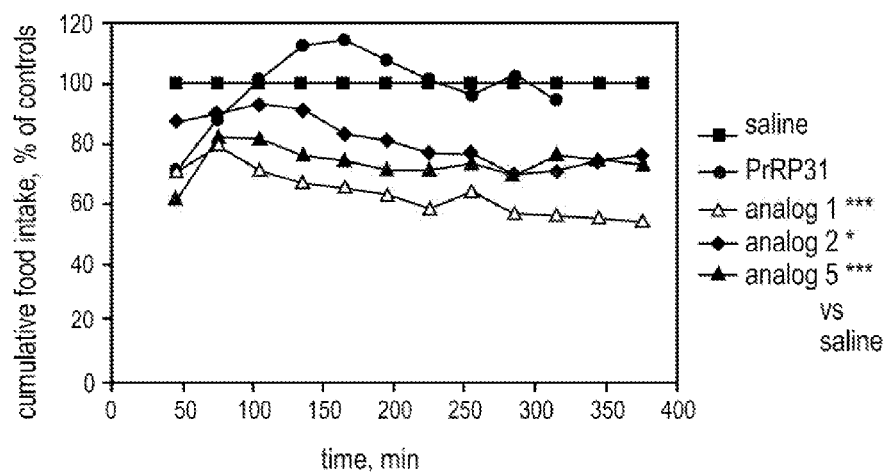
FIG. 2 represents the time course of food intake after ICV administration of analogs PrRP31 with varying length of the lipid chain to fasted C57BL/6 mice at the dose of 4 nmol/mouse. On the x axis is time in minutes, on the y axis, the cumulative food intake as a % of food intake in the control group injected with the saline (n=6-7). The significance is P<0.01, *P<0.001 versus saline throughout the time course of the test (one-way ANOVA followed by Dunnett post-hoc test). ■—saline, ●—PrRP31, △—analog 1, ♦—analog 2, ▲—analog 5.
Figure 3:
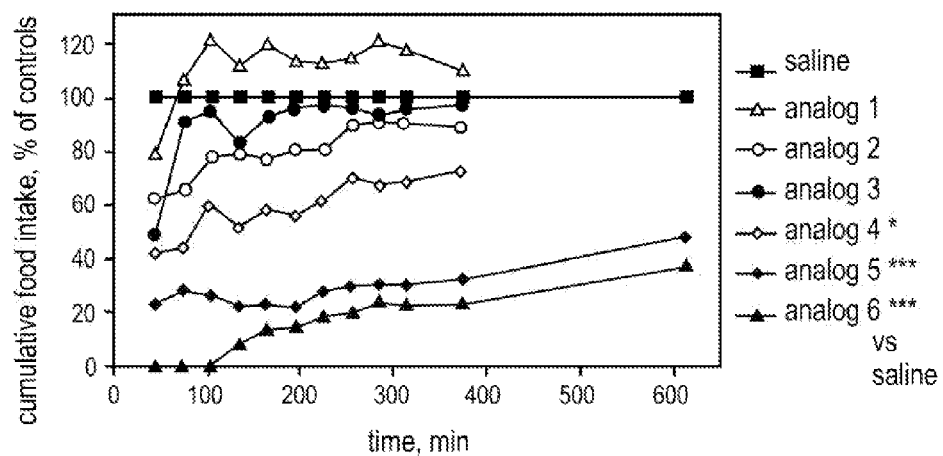
FIG. 3 represents the time course of food intake after SC administration of analogs of PrRP31 with varying length of the lipid chain to fasted C57BL/6 mice at a dose of 5 mg/kg. On the x axis is time in minutes, on the y axis, the cumulative food intake as a % of food intake in the control group injected with the saline (n=6). The significance is *P<0.05, ***P<0.001 versus saline throughout the time course of the test (one-way ANOVA followed by Dunnett post-hoc test). ■—saline, △—analog 1, ○—analog 2, ●—analog 3, ◇—analog 4, ♦—analog 5, ▲—analog 6.

Lipidated analogs of PrRP31 and PrRP20 lowered food intake in fasted mice after ICV administration to a comparable degree as PrRP31 (FIG. 1) but the effect was prolonged (see, e.g., FIG. 2). The effect of lipidated analogs of PrRP after ICV administration was not dependent on the length or presence of the fatty acid.

Lipidated analogs of the rat PrRP31 and PrRP20 with bound myristic or palmitic acid (FIG. 3) significantly lowered (and for a prolonged period of time) the food intake in fasted mice after SC administration. The analog with tridecanoic acid partially lowered the food intake, however. The analogs lacking fatty acid or containing octanoyl or dodecanoyl had no effect or did not significantly lower food intake. This was most likely caused by a poor penetration through the hematocephalic barrier.

Figure 4:
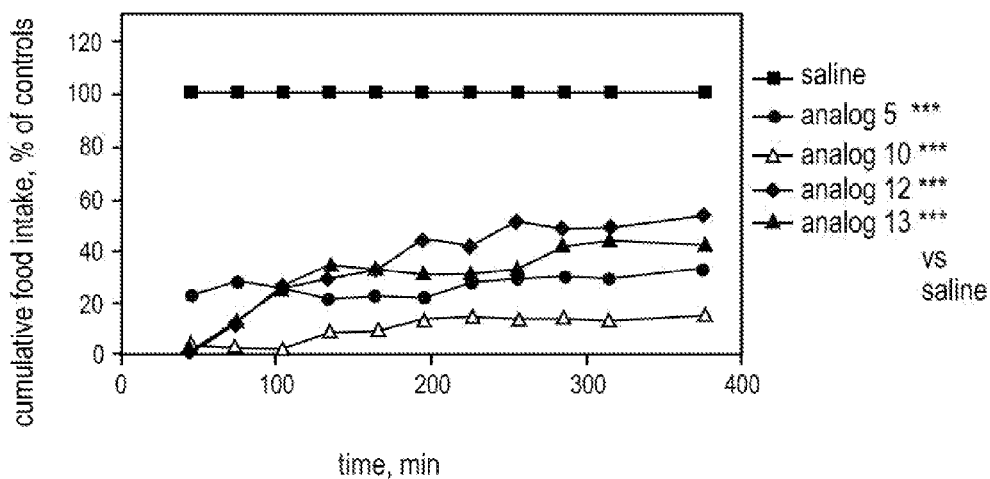
FIG. 4 represents the time course of food intake after SC administration of human and rat lipidated analogs of PrRP31 and PrRP20 to fasted C57BL/6 mice at a dose of 5 mg/kg. On the x axis is time in minutes, on the y axis, the cumulative food intake as a % of food intake in the control group injected with the saline (n=6). The significance is ***P<0.001 versus saline throughout the time course of the test (one-way ANOVA followed by Dunnett post-hoc test). ■—saline, ●—analog 5, △—analog 10, ♦—analog 12, ▲—analog 13.
Figure 5:
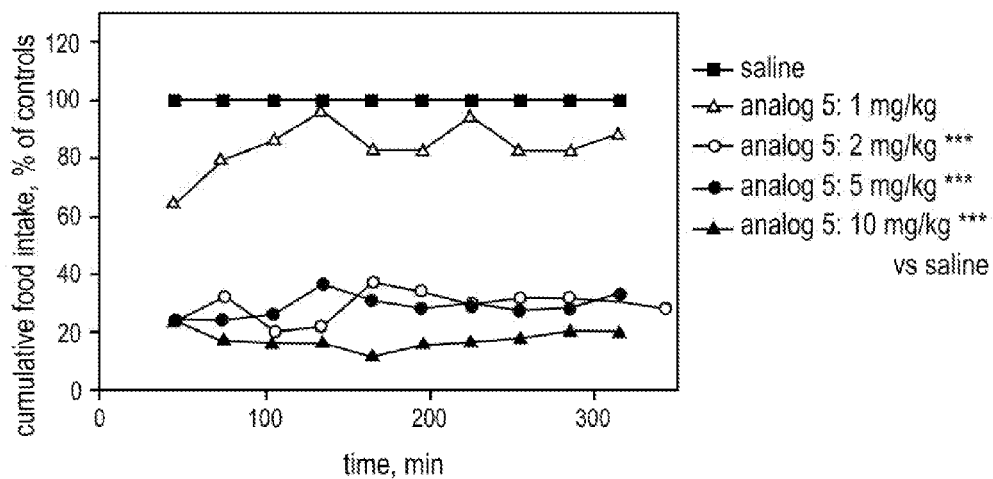
FIG. 5 represents the time course of food intake after SC administration of myristoylated analog [Dpr$^1$]PrRP31 (No. 5) to fasted C57BL/6 mice at the doses of 1, 2, 5 and 10 mg/kg. On the x axis is time in minutes, on the y axis, the cumulative food intake as a % of food intake in the control group injected with the saline (n=6). The significance is ***P<0.001 versus saline throughout the time course of the test (one-way ANOVA followed by Dunnett post-hoc test). ■—saline, △—analog 5: 1 mg/kg, ○—analog 5: 2 mg/kg, ●—analog 5: 5 mg/kg, ▲—analog 5: 10 mg/kg.
Figure 6:
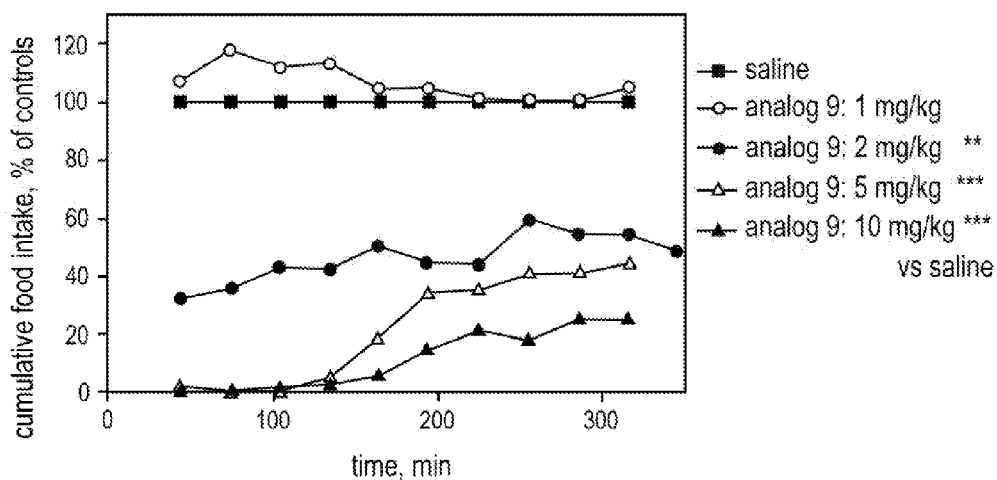
FIG. 6 represents the time course of food intake after SC administration of myristoylated analog [Dpr$^1$ Nal$^{31}$]PrRP31 (No. 9) to fasted C57BL/6 mice at the doses of 1, 2, 5 and 10 mg/kg. On the x axis is time in minutes, on the y axis, the cumulative food intake as a % of food intake in the control group injected with the saline (n=6). The significance is P<0.01, *P<0.001 versus saline (one-way ANOVA followed by Dunnett post-hoc test). ■—saline, ○—analog 9: 1 mg/kg, ●—analog 9: 2 mg/kg, △—analog 9: 5 mg/kg, ▲—analog 9: 10 mg/kg.

Myristoylated analogs of human PrRP31 and PrRP20 significantly lowered food intake in fasted mice, comparable to the effect of corresponding rat analogs (FIG. 4). The lowering of food intake in mice after SC administration of the lipidated PrRP analogs was dose dependent (FIG. 5 demonstrates the effect of compound 5 and FIG. 6, the effect of compound 9). Doses of 2-10 mg/kg significantly lowered food intake.

Example 5. Fos Immunohistochemistry

Tissue Processing

For Fos immunohistochemical processing, overnight fasted mice (n=5 mice/group) were treated SC with saline, [Dpr$^1$]PrRP31, [Dpr(oct)$^1$]PrRP31, [Dpr(myr)$^1$]PrRP31 or [Dpr(palm)$^1$]PrRP31 (dose 5 mg/kg). Ninety minutes after SC injection, the mice were deeply anesthetized with pentobarbital (50 mg/kg, IP) and perfused transcardially with 0.1 M phosphate buffer (PB, pH 7.4) containing 4% paraformaldehyde, 0.1% glutaraldehyde, and 10% picric acid (w/w). Then the brains were removed, postfixed in the same fixative overnight at 4° C., and infiltrated with 30% sucrose in 0.1 M PB for 48 h at 4° C. Before sectioning, the brains were rapidly (20 sec) frozen in cold isopentane (−30/−40° C.) and placed into a Reichert cryocut device adjusted to −16° C. for 1 h. 30 μm coronal sections were cut from the brains and collected as free floating in cold (4° C.) PB.

Immunohistochemistry

Free floating sections were repeatedly washed in cold PB followed by preincubation in 3% $H_2O_2$ for 40 min at room temperature. They were incubated with polyclonal Fos protein antiserum (1:2000), diluted in 0.1 M PB containing 4% normal goat serum (Gibco, Grand Island, N.Y., USA), 0.5% Triton X-100 (Koch-Light Lab. Ltd., Colnbrook, Berks, England), and 0.1% sodium azide for 48 h at 4° C. After several rinses in PB, the sections were incubated with biotinylated goat-anti-rabbit IgG (1:500, VectorStain Elite ABC, Vector Lab., Burlingame, Calif., USA) for 90 min at room temperature. Next PB rinses were followed by incubation with the avidin-biotin peroxidase complex (1:250) for 90 min at room temperature. PB washing was followed by washing in 0.05 M sodium acetate buffer (SAB, pH 6.0). The Fos antigenic sites were visualized with 0.0266% 3,3'-diaminobenzidine tetrahydrochloride (DAB) dissolved in SAB containing 0.0042% $H_2O_2$ and 2.5% nickel ammonium sulfate, for 7 min. The metal-intensification of DAB produced black staining in the labeled nuclei. Finally, the sections were rinsed in 0.05 M SAB, mounted into 0.1% of gelatine dissolved in 0.0125 M SAB, air-dried and coverslipped with Permount (Sigma, St. Louis, Mo., USA). Immunostaining of negative controls, which did not show any antiserum immunolabeling, included substitution of the primary antiserum with normal rabbit serum, and sequential elimination of the primary or secondary antibody from the staining series.

Evaluation of the Immunostaining

An identical set of mice was used for determination of Fos immunoreactivity in NTS, PVN, and Arc. Counting of Fos immunoreactive cells within the NTS, from Bregma −7.48 mm to Bregma −7.32 mm, PVN, from Bregma −0.7 mm to −0.94 mm, and DMH, from Bregma −1.46 mm to −1.82 mm according to the mouse brain atlas (Franklin K B J, Paxinos G: *The mouse brain in stereotaxic coordinates.* New York: Academic Press; 1997), was performed separately in each side of the sections. Quantitative assessment was performed from the images captured with a Canon digital camera (PowerShot S40) and Leica DMLS light microscope on a computer screen obtained from 5-6 brain sections per animal. Representative sections were captured by the same computerized system. The counting of Fos-positive neurons was done under blinded conditions (the counted slides from each animal were analyzed independently and randomly and encoded by other person).

Figure 7A:
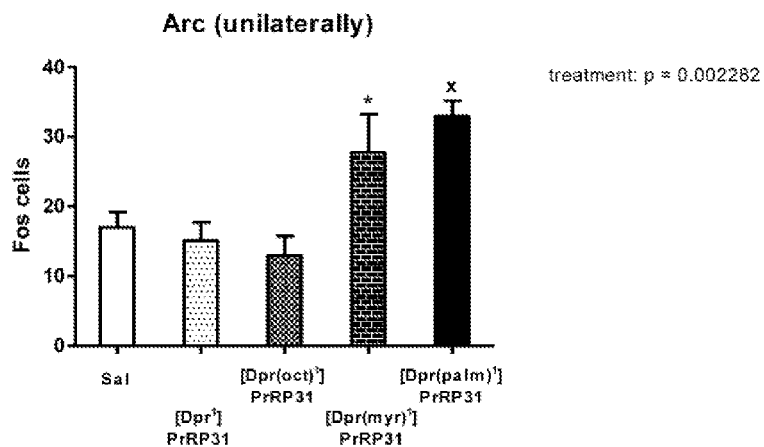
FIG. 7 represents neural activity showed as Fos immunoreactivity. Fos-immunostained cells in coronal section and number of Fos-immunopositive cells of A/Arc, B/PVN, C/NTS, 90 minutes after SC application of saline, [Dpr$^1$]PrRP31, [Dpr(oct)$^1$]PrRP31, [Dpr(myr)$^1$]PrRP31 or [Dpr(palm)$^1$]PrRP31 (dose 5 mg/kg, unilaterally per mouse (n=5) and section (n=5-6)). Significance: A/*p<0.05 vs [Dpr(oct)$^1$]PrRP31, $^x$p<0.05 vs Sal, [Dpr$^1$]PrRP31, Dpr(oct)$^1$] PrRP31, B, C/*p<0.05 vs Sal, [Dpr$^1$]PrRP31, Dpr(oct)$^1$]PrRP31. Sal—saline, NTS—solitary tract nucleus, AP—area postrema, PVN—paraventricular nucleus.
Figure 7B:
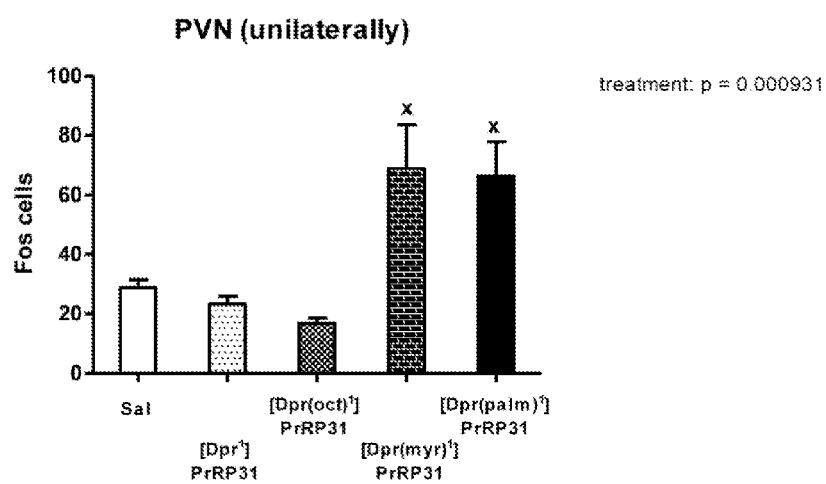
Figure 7C:
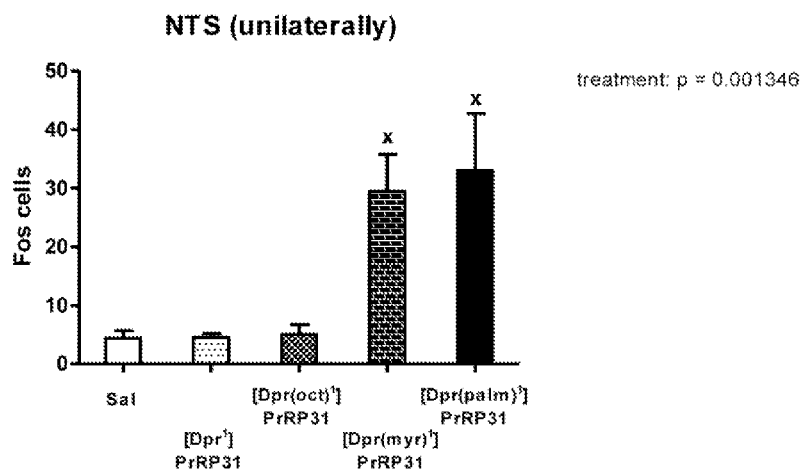

Results are shown in FIG. 7. Neural activity presented in Fos immunoreactivity was significantly increased in a case of [Dpr(myr)$^1$]PrRP31 and [Dpr(palm)$^1$]PrRP31 analogs in all brain nuclei involved in food intake regulation tested (i.e. Arc, PVN and NTS). These two analogs also significantly decreased food intake.

Example 6. Open Field Locomotor Activity and Hot-Plate Analgesic Test

Locomotor activity was measured using the VideoMot system (TSE Systems, Bad Homburg, Germany). Ad libitum fed mice were placed individually in the open field (1×1 m) and their locomotor activity, total distance traveled, was measured for 10 min. Mice were administered with SC injection of saline, [Dpr$^1$]PrRP31, [Dpr(palm)$^1$]PrRP31 or myr-PrRP20 (dose 5 mg/kg, n=5 mice/group).

Analgesia was measured by a hot-plate analgesia meter (TSE Systems, Bad Homburg, Germany) set at 53° C. after completion of the locomotor activity test. The end-point was the latency to jump, after which the animals were immediately removed from the plate.

Figure 8A:
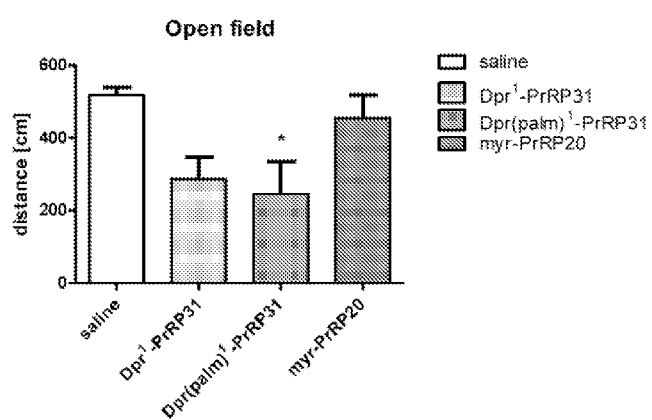
FIG. 8 represents behavioral activity of fed mice: A/open field test, total distance traveled for 10 min and B/analgesic test, hot plate (latency to jump) after administration with SC injection of saline, [Dpr$^1$]PrRP31, [Dpr(palm)$^1$]PrRP31 or myr-PrRP20 (dose 5 mg/kg, n=5 mice/group).
Figure 8B:

Results of behavioral tests in mice are described in FIG. 8. Administration of lipidized PrRP analogs caused mild sedative effect similar as an effect accompanying satiety induced by, for example, cholecystokinin. PrRP analogs also showed some analgesic effect.

Example 7. 14-Day Administration of Lipopeptides in Model of Diet-Induced (DIO) Mice Inbred C57BL/6 male mice (AnLab, Prague, Czech Republic) were housed at a temperature of 23° C. under a daily cycle of 12 hours light and dark (light from 6:00 a.m.) with free access to water and food pellets (St-1, Mlýn Kocanda, Jesenice, Czech Republic).

At 8 weeks of age, mice were divided into a standard (St) diet-fed group (the energy content of the St-1 diet was 3.4 kcal/g, containing 25, 9, and 66% of calories from protein, fat, and carbohydrate, respectively (St-1, Mlýn Kocanda, Jesenice, Czech Republic)) and a high fat (HF) diet-fed group (the energy content of the HF diet was 5.3 kcal/g, containing 13, 60, and 27% of calories from protein, fat, and carbohydrate, respectively). The HF diet consisted of 40% standard St-1 diet, 34% powdered cow milk for human neonates, 25% lard, and 1% corn starch w/w (Kopecký, J., et al., "Reduction of dietary obesity in aP2-Ucp transgenic mice: physiology and adipose tissue distribution," *Am J Physiol,* 270:E768-75, 1996). Food intake and body weight were monitored weekly from 9 to 20 weeks of age. Mice resistant to the HF diet were withdrawn from the experiment (approximately 10% of mice).

At the age of 20 weeks, mice were placed into separate cages with free access to food and water. The following week, mice were subjected to a 14-day food intake experiment. They were injected with palm-PrRP31 or myr-PrRP20 dissolved in saline at doses of 5 mg/kg (n=10) or saline twice a day (at 8:00 and 18:00) for 14 days. Consumption of the St or HF diet and the weight of the mice were simultaneously followed.

After 14 days of treatment, mice were fasted overnight and sacrificed the following morning. Their blood sera were isolated, and the white adipose tissue (subcutaneous, abdominal, and gonadal), and the liver of all mice were dissected, weighed, and stored at −70° C. Fat to body weight ratio was calculated as a ratio of adipose tissue weight to body weight.

Determination of Hormonal and Biochemical Parameters

Serum insulin and leptin concentrations were measured by RIA assays. Serum glucose levels were measured using a Glucocard glucometer (Arkray, Kyoto, Japan). Serum triglyceride levels were measured by quantitative enzymatic reactions (Sigma, St. Louis, USA).

Statistical Analysis

The data are presented as means±SEM for the number of animals indicated in the Figures and Tables. They were analyzed by a one-way ANOVA followed by a Dunnett post-hoc test (metabolic parameters, behavioral study) or two-way ANOVA followed by a Bonferroni post-hoc test (body weight evaluation) using Graph-Pad Software (San Diego, Calif., USA). $P<0.05$ was considered statistically significant.

Figure 9:
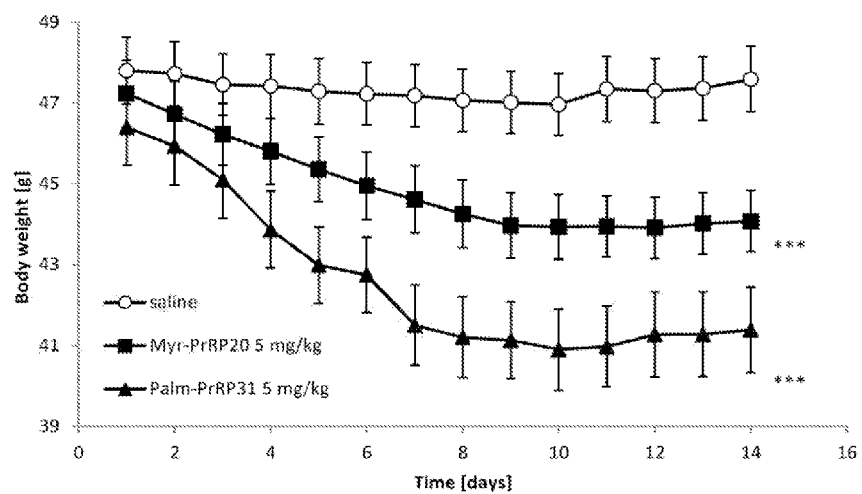
FIG. 9 represents long-term effect of lipidized PrRP analogs on body weight in a DIO model of mice (SC administration, dose 5 mg/kg, twice per day for 14 days) (n=10). The data were analyzed by two-way ANOVA (treatment×time after injection). ***P<0.001 vs. respective saline-treated group.

Results of long-term administration of myr-PrRP20 and palm-PrRP31 into DIO mice are shown in FIG. 9 (body weight change) and Table 6 (metabolic parameters). Body weight of DIO mice significantly decreased both after myr-PrRP20 and palm-PrRP31 treatment. Fat/body weight, liver weight, leptin and insulin were also significantly lowered, especially after palm-PrRP31 administration.

of analog 55 in a dose of 1.0 mg/kg or 2.0 mg/kg. Test item formulation was prepared in saline solution as a fresh solution, just before dosing.

All of the animals were observed for clinical signs, morbidity or mortality once a day during acclimatisation and frequently after the administration. Food intake monitoring was performed 2, 4, 8 and 24 hours after single administration.

All of the animals were in good health throughout the acclimatisation, treatment period, no clinical symptoms of toxicity were observed after the administration of analog 55. Significantly lower food intake after both injected doses of the peptide in comparison to the saline-treated animals was observed between 1-6 hours after the single subcutaneous administration of analog 55.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope

TABLE 6

Metabolic parameters after 14-days SC administration of lipidized PrRP analogs in 17 h fasted DIO male mice

| Treatment | Fat/body weight [%] | Liver/body weight [%] | Leptin [ng/ml] | Glucose [mmol/l] | Insulin [ng/ml] | Triglycerides [mg/dl] |
|---|---|---|---|---|---|---|
| Saline | 16.15 ± 0.40 | 4.07 ± 0.19 | 53.26 ± 3.49 | 6.94 ± 0.28 | 4.09 ± 0.55 | 72.25 ± 3.20 |
| Myr-PrRP20 | 15.30 ± 0.42 | 3.60 ± 0.18* | 39.56 ± 3.47*** | 7.52 ± 0.16 | 3.54 ± 0.47 | 68.71 ± 4.16 |
| Palm-PrRP31 | 12.69 ± 0.71*** | 3.56 ± 0.07** | 24.71 ± 3.39*** | 7.26 ± 0.29 | 2.37 ± 0.47** | 66.81 ± 8.74 |

All values are expressed as mean ± SEM (n = 10 per group).

Significance (one-way ANOVA following by Dunnett post-hoc test) is $*P < 0.05$, $P < 0.01$, $*P < 0.001$ vs saline.

Example 8: Test of Food Intake after Administration of Analog No. 55 to Rhesus Monkeys Food intake (amount of pellets consumed) was measured in Rhesus monkey (n=4) after a single subcutaneous administration of myristoylated human PrRP20 (analog no. 55).

The study was conducted on overnight fasted animals in Meditox breeding facility (Konárovice, Czech Republic). Each animal received a subcutaneous injection of saline, or of the invention and that methods and structures within the scope of these claims and their equivalents be covered thereby.

Work underlying this disclosure was undertaken pursuant to a joint research agreement between Ustav Organicke Chemie A Biochemie Akademie Ved CR, V.V.I. and Fyziologicky Ustav Akademie Ved CR, V.V.I., both institutions located in the Czech Republic.

What is claimed is:

1. A lipidated analog of prolactin-releasing peptide having the formula:

(palm)-SRTHRHSMEIRTPDINPAWYASRGIR-PVGRF-NH$_2$ (SEQ ID NO: 55).

2. A pharmaceutical composition comprising a lipidated analog of prolactin-releasing peptide according to claim 1 and one or more physiologically acceptable substances selected from a carrier, a diluent, and an excipient.

3. A pharmaceutical composition comprising a lipidated analog of prolactin-releasing peptide according to claim 1 and at least one additional active ingredient.

4. A lipidated analog of prolactin-releasing peptide having the formula:

(myr)-SRTHRHSMEIRTPDINPAWYASRGIR-PVGRF-NH2 (SEQ ID NO: 56).

5. A pharmaceutical composition comprising a lipidated analog of prolactin-releasing peptide according to claim 4 and one or more physiologically acceptable substances selected from a carrier, a diluent, and an excipient.

6. A pharmaceutical composition comprising a lipidated analog of prolactin-releasing peptide according to claim 4 and at least one additional active ingredient.

7. A method of lowering food intake in a subject suffering from obesity, comprising peripheral administration of a prolactin-releasing peptide analog according to claim 1 to a subject in need thereof.

8. A method of treating a subject diagnosed with obesity, the method comprising administering a lipidated analog of prolactin-releasing peptide according to claim 1 to a subject in need thereof.

9. A method of treating a subject diagnosed with obesity, the method comprising administering a lipidated analog of prolactin-releasing peptide according to claim 4 to a subject in need thereof.

10. A method of lowering food intake in a subject diagnosed with obesity, the method comprising peripheral administration of a lipidated analog of prolactin-releasing peptide according to claim 4 to a subject in need thereof.

* * * * *

SEQUENCE LISTING

<160> NUMBER OF SEQ ID NOS: 126

<210> SEQ ID NO 1
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="Fatty acid C6 to C18 bound by an amide
      bond to an amino group of a N-terminal amino acid"
<220> FEATURE:
<221> NAME/KEY: misc_feature
<222> LOCATION: (1)..(24)
<223> OTHER INFORMATION: /note="Any amino acid and this region may
      encompass 13 or 24 residues"
<220> FEATURE:
<221> NAME/KEY: VARIANT
<222> LOCATION: (14)..(24)
<223> OTHER INFORMATION: /replace=" "
<220> FEATURE:
<221> NAME/KEY: VARIANT
<222> LOCATION: (25)..(25)
<223> OTHER INFORMATION: /replace="Ala" or "phenylglycine"
<220> FEATURE:
<221> NAME/KEY: VARIANT
<222> LOCATION: (28)..(28)
<223> OTHER INFORMATION: /replace="phenylglycine"
<220> FEATURE:
<221> NAME/KEY: VARIANT
<222> LOCATION: (31)..(31)
<223> OTHER INFORMATION: /replace="An amino acid with a side chain
      containing CH2-Ar or CH2-S-CH2-Ar, wherein Ar represents phenyl
      or napthyl, optionally substituted by a halogen or nitro group"
<220> FEATURE:
<221> NAME/KEY: misc_feature
<222> LOCATION: (31)..(31)
<223> OTHER INFORMATION: /note="C-term NH2"
<220> FEATURE:
<221> NAME/KEY: misc_feature
<222> LOCATION: (1)..(31)
<223> OTHER INFORMATION: /note="Variant residues given in the sequence
      have no preference with respect to those in the annotations for
      variant positions"

<400> SEQUENCE: 1

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Ile Arg Pro Val Gly Arg Phe
            20                  25                  30

<210> SEQ ID NO 2
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="Fatty acid C6 to C18 bound by an amide
      bond to an amino group of a N-terminal amino acid"
<220> FEATURE:
<221> NAME/KEY: VARIANT
<222> LOCATION: (1)..(1)
<223> OTHER INFORMATION: /replace="Thr" or "diaminopropionic acid"
<220> FEATURE:
<221> NAME/KEY: misc_feature
<222> LOCATION: (2)..(24)

```
<223> OTHER INFORMATION: /note="Any amino acid and this region may
      encompass 12 or 23 residues"
<220> FEATURE:
<221> NAME/KEY: VARIANT
<222> LOCATION: (14)..(24)
<223> OTHER INFORMATION: /replace=" "
<220> FEATURE:
<221> NAME/KEY: VARIANT
<222> LOCATION: (25)..(25)
<223> OTHER INFORMATION: /replace="Ala" or "phenylglycine"
<220> FEATURE:
<221> NAME/KEY: VARIANT
<222> LOCATION: (28)..(28)
<223> OTHER INFORMATION: /replace="phenylglycine"
<220> FEATURE:
<221> NAME/KEY: VARIANT
<222> LOCATION: (31)..(31)
<223> OTHER INFORMATION: /replace="An amino acid with a side chain
      containing CH2-Ar or CH2-S-CH2-Ar, wherein Ar represents phenyl
      or napthyl, optionally substituted by a halogen or nitro group"
<220> FEATURE:
<221> NAME/KEY: misc_feature
<222> LOCATION: (31)..(31)
<223> OTHER INFORMATION: /note="C-term NH2"
<220> FEATURE:
<221> NAME/KEY: misc_feature
<222> LOCATION: (1)..(31)
<223> OTHER INFORMATION: /note="Variant residues given in the sequence
      have no preference with respect to those in the annotations for
      variant positions"

<400> SEQUENCE: 2

Ser Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Ile Arg Pro Val Gly Arg Phe
            20                  25                  30

<210> SEQ ID NO 3
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="Fatty acid C6 to C18 bound by an amide
      bond to an amino group of a N-terminal amino acid"
<220> FEATURE:
<221> NAME/KEY: VARIANT
<222> LOCATION: (1)..(1)
<223> OTHER INFORMATION: /replace="Thr" or "diaminopropionic acid"
<220> FEATURE:
<221> NAME/KEY: VARIANT
<222> LOCATION: (3)..(3)
<223> OTHER INFORMATION: /replace="Ala" or "methylalanine"
<220> FEATURE:
<221> NAME/KEY: VARIANT
<222> LOCATION: (5)..(5)
<223> OTHER INFORMATION: /replace="Arg"
<220> FEATURE:
<221> NAME/KEY: VARIANT
<222> LOCATION: (8)..(8)
<223> OTHER INFORMATION: /replace="Norleucine"
<220> FEATURE:
<221> NAME/KEY: VARIANT
<222> LOCATION: (10)..(10)
<223> OTHER INFORMATION: /replace="Ile"
<220> FEATURE:
<221> NAME/KEY: VARIANT
<222> LOCATION: (21)..(21)
<223> OTHER INFORMATION: /replace="Ala" or "methylalanine"
<220> FEATURE:
<221> NAME/KEY: VARIANT
```

```
<222> LOCATION: (22)..(22)
<223> OTHER INFORMATION: /replace="Ser"
<220> FEATURE:
<221> NAME/KEY: VARIANT
<222> LOCATION: (24)..(24)
<223> OTHER INFORMATION: /replace="Ala" or "Pro" or "N-methylglycine"
<220> FEATURE:
<221> NAME/KEY: VARIANT
<222> LOCATION: (25)..(25)
<223> OTHER INFORMATION: /replace="Ala" or "phenylglycine"
<220> FEATURE:
<221> NAME/KEY: VARIANT
<222> LOCATION: (28)..(28)
<223> OTHER INFORMATION: /replace="phenylglycine"
<220> FEATURE:
<221> NAME/KEY: VARIANT
<222> LOCATION: (31)..(31)
<223> OTHER INFORMATION: /replace="An amino acid with a side chain
      containing CH2-Ar or CH2-S-CH2-Ar, wherein Ar represents phenyl
      or napthyl, optionally substituted by a halogen or nitro group"
<220> FEATURE:
<221> NAME/KEY: misc_feature
<222> LOCATION: (31)..(31)
<223> OTHER INFORMATION: /note="C-term NH2"
<220> FEATURE:
<221> NAME/KEY: misc_feature
<222> LOCATION: (1)..(31)
<223> OTHER INFORMATION: /note="Variant residues given in the sequence
      have no preference with respect to those in the annotations for
      variant positions"
<220> FEATURE:
<221> NAME/KEY: misc_feature
<222> LOCATION: (1)..(31)
<223> OTHER INFORMATION: /note="see specification as filed for detailed
      description of substitutions and preferred embodiments"

<400> SEQUENCE: 3

Ser Arg Thr His Gln His Ser Met Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 4
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Thr" or "diaminopropionic acid"
<220> FEATURE:
<221> NAME/KEY: VARIANT
<222> LOCATION: (3)..(3)
<223> OTHER INFORMATION: /replace="Ala" or "methylalanine"
<220> FEATURE:
<221> NAME/KEY: VARIANT
<222> LOCATION: (5)..(5)
<223> OTHER INFORMATION: /replace="Arg"
<220> FEATURE:
<221> NAME/KEY: VARIANT
<222> LOCATION: (8)..(8)
<223> OTHER INFORMATION: /replace="Norleucine"
<220> FEATURE:
<221> NAME/KEY: VARIANT
<222> LOCATION: (10)..(10)
<223> OTHER INFORMATION: /replace="Ile"
<220> FEATURE:
<221> NAME/KEY: VARIANT
<222> LOCATION: (21)..(21)
<223> OTHER INFORMATION: /replace="Ala" or "methylalanine"
<220> FEATURE:
<221> NAME/KEY: VARIANT
```

```
<222> LOCATION: (22)..(22)
<223> OTHER INFORMATION: /replace="Ser"
<220> FEATURE:
<221> NAME/KEY: VARIANT
<222> LOCATION: (24)..(24)
<223> OTHER INFORMATION: /replace="Ala" or "Pro" or "N-methylglycine"
<220> FEATURE:
<221> NAME/KEY: misc_feature
<222> LOCATION: (1)..(24)
<223> OTHER INFORMATION: /note="Variant residues given in the sequence
      have no preference with respect to those in the annotations for
      variant positions"

<400> SEQUENCE: 4

Ser Arg Thr His Gln His Ser Met Glu Thr Arg Thr Pro Asp Ile Asn
1               5                   10                  15

Pro Ala Trp Tyr Thr Gly Arg Gly
            20

<210> SEQ ID NO 5
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="Fatty acid C6 to C18 bound by an amide
      bond to an amino group of a N-terminal amino acid"
<220> FEATURE:
<221> NAME/KEY: VARIANT
<222> LOCATION: (10)..(10)
<223> OTHER INFORMATION: /replace="Ala" or "methylalanine"
<220> FEATURE:
<221> NAME/KEY: VARIANT
<222> LOCATION: (11)..(11)
<223> OTHER INFORMATION: /replace="Ser"
<220> FEATURE:
<221> NAME/KEY: VARIANT
<222> LOCATION: (13)..(13)
<223> OTHER INFORMATION: /replace="Ala" or "Pro" or "N-methylglycine"
<220> FEATURE:
<221> NAME/KEY: VARIANT
<222> LOCATION: (14)..(14)
<223> OTHER INFORMATION: /replace="Ala" or "phenylglycine"
<220> FEATURE:
<221> NAME/KEY: VARIANT
<222> LOCATION: (17)..(17)
<223> OTHER INFORMATION: /replace="phenylglycine"
<220> FEATURE:
<221> NAME/KEY: VARIANT
<222> LOCATION: (20)..(20)
<223> OTHER INFORMATION: /replace="An amino acid with a side chain
      containing CH2-Ar or CH2-S-CH2-Ar, wherein Ar represents phenyl
      or napthyl, optionally substituted by a halogen or nitro group"
<220> FEATURE:
<221> NAME/KEY: misc_feature
<222> LOCATION: (20)..(20)
<223> OTHER INFORMATION: /note="C-term NH2"
<220> FEATURE:
<221> NAME/KEY: misc_feature
<222> LOCATION: (1)..(20)
<223> OTHER INFORMATION: /note="Variant residues given in the sequence
      have no preference with respect to those in the annotations for
      variant positions"

<400> SEQUENCE: 5

Thr Pro Asp Ile Asn Pro Ala Trp Tyr Thr Gly Arg Gly Ile Arg Pro
1               5                   10                  15

Val Gly Arg Phe
            20
```

```
<210> SEQ ID NO 6
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="Fatty acid C6 to C18 bound by an amide
      bond to an amino group of a N-terminal amino acid"
<220> FEATURE:
<221> NAME/KEY: VARIANT
<222> LOCATION: (3)..(3)
<223> OTHER INFORMATION: /replace="Ala" or "methylalanine"
<220> FEATURE:
<221> NAME/KEY: VARIANT
<222> LOCATION: (5)..(5)
<223> OTHER INFORMATION: /replace="Arg"
<220> FEATURE:
<221> NAME/KEY: VARIANT
<222> LOCATION: (8)..(8)
<223> OTHER INFORMATION: /replace="Norleucine"
<220> FEATURE:
<221> NAME/KEY: VARIANT
<222> LOCATION: (10)..(10)
<223> OTHER INFORMATION: /replace="Ile"
<220> FEATURE:
<221> NAME/KEY: VARIANT
<222> LOCATION: (21)..(21)
<223> OTHER INFORMATION: /replace="Ala" or "methylalanine"
<220> FEATURE:
<221> NAME/KEY: VARIANT
<222> LOCATION: (22)..(22)
<223> OTHER INFORMATION: /replace="Ser"
<220> FEATURE:
<221> NAME/KEY: VARIANT
<222> LOCATION: (24)..(24)
<223> OTHER INFORMATION: /replace="Ala" or "Pro" or "N-methylglycine"
<220> FEATURE:
<221> NAME/KEY: VARIANT
<222> LOCATION: (25)..(25)
<223> OTHER INFORMATION: /replace="Ala" or "phenylglycine"
<220> FEATURE:
<221> NAME/KEY: VARIANT
<222> LOCATION: (28)..(28)
<223> OTHER INFORMATION: /replace="phenylglycine"
<220> FEATURE:
<221> NAME/KEY: VARIANT
<222> LOCATION: (31)..(31)
<223> OTHER INFORMATION: /replace="Any amino acid with a side chain
      containing CH2-Ar or CH2-S-CH2-Ar, wherein Ar represents phenyl
      or napthyl, optionally substituted by a halogen or nitro group"
<220> FEATURE:
<221> NAME/KEY: misc_feature
<222> LOCATION: (1)..(31)
<223> OTHER INFORMATION: /note="Variant residues given in the sequence
      have no preference with respect to those in the annotations for
      variant positions"

<400> SEQUENCE: 6

Ser Arg Thr His Gln His Ser Met Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 7
<211> LENGTH: 31
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: (Dpr(oct))
<220> FEATURE:
<221> NAME/KEY: VARIANT
<222> LOCATION: (3)..(3)
<223> OTHER INFORMATION: /replace="Ala"
<220> FEATURE:
<221> NAME/KEY: VARIANT
<222> LOCATION: (5)..(5)
<223> OTHER INFORMATION: /replace="Arg"
<220> FEATURE:
<221> NAME/KEY: MOD_RES
<222> LOCATION: (8)..(8)
<223> OTHER INFORMATION: Nle
<220> FEATURE:
<221> NAME/KEY: VARIANT
<222> LOCATION: (21)..(21)
<223> OTHER INFORMATION: /replace="Ala"
<220> FEATURE:
<221> NAME/KEY: VARIANT
<222> LOCATION: (22)..(22)
<223> OTHER INFORMATION: /replace="Ser"
<220> FEATURE:
<221> NAME/KEY: VARIANT
<222> LOCATION: (25)..(25)
<223> OTHER INFORMATION: /replace="Ala" or "phenylglycine"
<220> FEATURE:
<221> NAME/KEY: VARIANT
<222> LOCATION: (28)..(28)
<223> OTHER INFORMATION: /replace="phenylglycine"
<220> FEATURE:
<221> NAME/KEY: misc_feature
<222> LOCATION: (31)..(31)
<223> OTHER INFORMATION: /note="C-term NH2"
<220> FEATURE:
<221> NAME/KEY: misc_feature
<222> LOCATION: (1)..(31)
<223> OTHER INFORMATION: /note="Variant residues given in the sequence
      have no preference with respect to those in the annotations for
      variant positions"

<400> SEQUENCE: 7

Xaa Arg Thr His Gln His Ser Leu Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 8
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: (Dpr(dodec))
<220> FEATURE:
<221> NAME/KEY: VARIANT
<222> LOCATION: (3)..(3)
<223> OTHER INFORMATION: /replace="Ala"
<220> FEATURE:
<221> NAME/KEY: VARIANT
<222> LOCATION: (5)..(5)
<223> OTHER INFORMATION: /replace="Arg"
<220> FEATURE:
<221> NAME/KEY: MOD_RES
<222> LOCATION: (8)..(8)
<223> OTHER INFORMATION: Nle
<220> FEATURE:

```
<221> NAME/KEY: VARIANT
<222> LOCATION: (21)..(21)
<223> OTHER INFORMATION: /replace="Ala"
<220> FEATURE:
<221> NAME/KEY: VARIANT
<222> LOCATION: (22)..(22)
<223> OTHER INFORMATION: /replace="Ser"
<220> FEATURE:
<221> NAME/KEY: VARIANT
<222> LOCATION: (25)..(25)
<223> OTHER INFORMATION: /replace="Ala" or "phenylglycine"
<220> FEATURE:
<221> NAME/KEY: VARIANT
<222> LOCATION: (28)..(28)
<223> OTHER INFORMATION: /replace="phenylglycine"
<220> FEATURE:
<221> NAME/KEY: misc_feature
<222> LOCATION: (31)..(31)
<223> OTHER INFORMATION: /note="C-term NH2"
<220> FEATURE:
<221> NAME/KEY: misc_feature
<222> LOCATION: (1)..(31)
<223> OTHER INFORMATION: /note="Variant residues given in the sequence
      have no preference with respect to those in the annotations for
      variant positions"

<400> SEQUENCE: 8

Xaa Arg Thr His Gln His Ser Leu Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 9
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: (Dpr(tridec))
<220> FEATURE:
<221> NAME/KEY: VARIANT
<222> LOCATION: (3)..(3)
<223> OTHER INFORMATION: /replace="Ala"
<220> FEATURE:
<221> NAME/KEY: VARIANT
<222> LOCATION: (5)..(5)
<223> OTHER INFORMATION: /replace="Arg"
<220> FEATURE:
<221> NAME/KEY: MOD_RES
<222> LOCATION: (8)..(8)
<223> OTHER INFORMATION: Nle
<220> FEATURE:
<221> NAME/KEY: VARIANT
<222> LOCATION: (21)..(21)
<223> OTHER INFORMATION: /replace="Ala"
<220> FEATURE:
<221> NAME/KEY: VARIANT
<222> LOCATION: (22)..(22)
<223> OTHER INFORMATION: /replace="Ser"
<220> FEATURE:
<221> NAME/KEY: VARIANT
<222> LOCATION: (25)..(25)
<223> OTHER INFORMATION: /replace="Ala" or "phenylglycine"
<220> FEATURE:
<221> NAME/KEY: VARIANT
<222> LOCATION: (28)..(28)
<223> OTHER INFORMATION: /replace="phenylglycine"
<220> FEATURE:
<221> NAME/KEY: misc_feature
<222> LOCATION: (31)..(31)
<223> OTHER INFORMATION: /note="C-term NH2"
```

-continued

```
<220> FEATURE:
<221> NAME/KEY: misc_feature
<222> LOCATION: (1)..(31)
<223> OTHER INFORMATION: /note="Variant residues given in the sequence
      have no preference with respect to those in the annotations for
      variant positions"

<400> SEQUENCE: 9

Xaa Arg Thr His Gln His Ser Leu Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 10
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: (Dpr(myr))
<220> FEATURE:
<221> NAME/KEY: VARIANT
<222> LOCATION: (3)..(3)
<223> OTHER INFORMATION: /replace="Ala"
<220> FEATURE:
<221> NAME/KEY: VARIANT
<222> LOCATION: (5)..(5)
<223> OTHER INFORMATION: /replace="Arg"
<220> FEATURE:
<221> NAME/KEY: MOD_RES
<222> LOCATION: (8)..(8)
<223> OTHER INFORMATION: Nle
<220> FEATURE:
<221> NAME/KEY: VARIANT
<222> LOCATION: (21)..(21)
<223> OTHER INFORMATION: /replace="Ala"
<220> FEATURE:
<221> NAME/KEY: VARIANT
<222> LOCATION: (22)..(22)
<223> OTHER INFORMATION: /replace="Ser"
<220> FEATURE:
<221> NAME/KEY: VARIANT
<222> LOCATION: (25)..(25)
<223> OTHER INFORMATION: /replace="Ala" or "phenylglycine"
<220> FEATURE:
<221> NAME/KEY: VARIANT
<222> LOCATION: (28)..(28)
<223> OTHER INFORMATION: /replace="phenylglycine"
<220> FEATURE:
<221> NAME/KEY: misc_feature
<222> LOCATION: (31)..(31)
<223> OTHER INFORMATION: /note="C-term NH2"
<220> FEATURE:
<221> NAME/KEY: misc_feature
<222> LOCATION: (1)..(31)
<223> OTHER INFORMATION: /note="Variant residues given in the sequence
      have no preference with respect to those in the annotations for
      variant positions"

<400> SEQUENCE: 10

Xaa Arg Thr His Gln His Ser Leu Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 11
<211> LENGTH: 31
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: (Dpr(palm))
<220> FEATURE:
<221> NAME/KEY: VARIANT
<222> LOCATION: (3)..(3)
<223> OTHER INFORMATION: /replace="Ala"
<220> FEATURE:
<221> NAME/KEY: VARIANT
<222> LOCATION: (5)..(5)
<223> OTHER INFORMATION: /replace="Arg"
<220> FEATURE:
<221> NAME/KEY: MOD_RES
<222> LOCATION: (8)..(8)
<223> OTHER INFORMATION: Nle
<220> FEATURE:
<221> NAME/KEY: VARIANT
<222> LOCATION: (21)..(21)
<223> OTHER INFORMATION: /replace="Ala"
<220> FEATURE:
<221> NAME/KEY: VARIANT
<222> LOCATION: (22)..(22)
<223> OTHER INFORMATION: /replace="Ser"
<220> FEATURE:
<221> NAME/KEY: VARIANT
<222> LOCATION: (25)..(25)
<223> OTHER INFORMATION: /replace="Ala" or "phenylglycine"
<220> FEATURE:
<221> NAME/KEY: VARIANT
<222> LOCATION: (28)..(28)
<223> OTHER INFORMATION: /replace="phenylglycine"
<220> FEATURE:
<221> NAME/KEY: misc_feature
<222> LOCATION: (31)..(31)
<223> OTHER INFORMATION: /note="C-term NH2"
<220> FEATURE:
<221> NAME/KEY: misc_feature
<222> LOCATION: (1)..(31)
<223> OTHER INFORMATION: /note="Variant residues given in the sequence
      have no preference with respect to those in the annotations for
      variant positions"

<400> SEQUENCE: 11

Xaa Arg Thr His Gln His Ser Leu Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 12
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term (myr)"
<220> FEATURE:
<221> NAME/KEY: VARIANT
<222> LOCATION: (10)..(10)
<223> OTHER INFORMATION: /replace="Ala"
<220> FEATURE:
<221> NAME/KEY: VARIANT
<222> LOCATION: (11)..(11)
<223> OTHER INFORMATION: /replace="Ser"
<220> FEATURE:
<221> NAME/KEY: VARIANT
```

```
<222> LOCATION: (14)..(14)
<223> OTHER INFORMATION: /replace="Ala" or "phenylglycine"
<220> FEATURE:
<221> NAME/KEY: VARIANT
<222> LOCATION: (17)..(17)
<223> OTHER INFORMATION: /replace="phenylglycine"
<220> FEATURE:
<221> NAME/KEY: misc_feature
<222> LOCATION: (20)..(20)
<223> OTHER INFORMATION: /note="C-term NH2"
<220> FEATURE:
<221> NAME/KEY: misc_feature
<222> LOCATION: (1)..(20)
<223> OTHER INFORMATION: /note="Variant residues given in the sequence
      have no preference with respect to those in the annotations for
      variant positions"

<400> SEQUENCE: 12

Thr Pro Asp Ile Asn Pro Ala Trp Tyr Thr Gly Arg Gly Ile Arg Pro
1               5                   10                  15

Val Gly Arg Phe
            20

<210> SEQ ID NO 13
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term (palm)"
<220> FEATURE:
<221> NAME/KEY: VARIANT
<222> LOCATION: (10)..(10)
<223> OTHER INFORMATION: /replace="Ala"
<220> FEATURE:
<221> NAME/KEY: VARIANT
<222> LOCATION: (11)..(11)
<223> OTHER INFORMATION: /replace="Ser"
<220> FEATURE:
<221> NAME/KEY: VARIANT
<222> LOCATION: (14)..(14)
<223> OTHER INFORMATION: /replace="Ala" or "phenylglycine"
<220> FEATURE:
<221> NAME/KEY: VARIANT
<222> LOCATION: (17)..(17)
<223> OTHER INFORMATION: /replace="phenylglycine"
<220> FEATURE:
<221> NAME/KEY: misc_feature
<222> LOCATION: (20)..(20)
<223> OTHER INFORMATION: /note="C-term NH2"
<220> FEATURE:
<221> NAME/KEY: misc_feature
<222> LOCATION: (1)..(20)
<223> OTHER INFORMATION: /note="Variant residues given in the sequence
      have no preference with respect to those in the annotations for
      variant positions"

<400> SEQUENCE: 13

Thr Pro Asp Ile Asn Pro Ala Trp Tyr Thr Gly Arg Gly Ile Arg Pro
1               5                   10                  15

Val Gly Arg Phe
            20

<210> SEQ ID NO 14
<211> LENGTH: 31
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: (Dpr(oct))
<220> FEATURE:
<221> NAME/KEY: VARIANT
<222> LOCATION: (3)..(3)
<223> OTHER INFORMATION: /replace="Ala"
<220> FEATURE:
<221> NAME/KEY: VARIANT
<222> LOCATION: (5)..(5)
<223> OTHER INFORMATION: /replace="Arg"
<220> FEATURE:
<221> NAME/KEY: MOD_RES
<222> LOCATION: (8)..(8)
<223> OTHER INFORMATION: Nle
<220> FEATURE:
<221> NAME/KEY: VARIANT
<222> LOCATION: (21)..(21)
<223> OTHER INFORMATION: /replace="Ala"
<220> FEATURE:
<221> NAME/KEY: VARIANT
<222> LOCATION: (22)..(22)
<223> OTHER INFORMATION: /replace="Ser"
<220> FEATURE:
<221> NAME/KEY: VARIANT
<222> LOCATION: (25)..(25)
<223> OTHER INFORMATION: /replace="Ala" or "phenylglycine"
<220> FEATURE:
<221> NAME/KEY: VARIANT
<222> LOCATION: (28)..(28)
<223> OTHER INFORMATION: /replace="phenylglycine"
<220> FEATURE:
<221> NAME/KEY: MOD_RES
<222> LOCATION: (31)..(31)
<223> OTHER INFORMATION: 1-Nal
<220> FEATURE:
<221> NAME/KEY: misc_feature
<222> LOCATION: (31)..(31)
<223> OTHER INFORMATION: /note="C-term NH2"
<220> FEATURE:
<221> NAME/KEY: misc_feature
<222> LOCATION: (1)..(31)
<223> OTHER INFORMATION: /note="Variant residues given in the sequence
      have no preference with respect to those in the annotations for
      variant positions"

<400> SEQUENCE: 14

Xaa Arg Thr His Gln His Ser Leu Glu Thr Arg Thr Pro Asp Ile Asn
1               5                   10                  15

Pro Ala Trp Tyr Thr Gly Arg Gly Ile Arg Pro Val Gly Arg Ala
            20                  25                  30

<210> SEQ ID NO 15
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: (Dpr(dodec))
<220> FEATURE:
<221> NAME/KEY: VARIANT
<222> LOCATION: (3)..(3)
<223> OTHER INFORMATION: /replace="Ala"
<220> FEATURE:
<221> NAME/KEY: VARIANT
<222> LOCATION: (5)..(5)
<223> OTHER INFORMATION: /replace="Arg"
```

```
<220> FEATURE:
<221> NAME/KEY: MOD_RES
<222> LOCATION: (8)..(8)
<223> OTHER INFORMATION: Nle
<220> FEATURE:
<221> NAME/KEY: VARIANT
<222> LOCATION: (21)..(21)
<223> OTHER INFORMATION: /replace="Ala"
<220> FEATURE:
<221> NAME/KEY: VARIANT
<222> LOCATION: (22)..(22)
<223> OTHER INFORMATION: /replace="Ser"
<220> FEATURE:
<221> NAME/KEY: VARIANT
<222> LOCATION: (25)..(25)
<223> OTHER INFORMATION: /replace="Ala" or "phenylglycine"
<220> FEATURE:
<221> NAME/KEY: VARIANT
<222> LOCATION: (28)..(28)
<223> OTHER INFORMATION: /replace="phenylglycine"
<220> FEATURE:
<221> NAME/KEY: MOD_RES
<222> LOCATION: (31)..(31)
<223> OTHER INFORMATION: 1-Nal
<220> FEATURE:
<221> NAME/KEY: misc_feature
<222> LOCATION: (31)..(31)
<223> OTHER INFORMATION: /note="C-term NH2"
<220> FEATURE:
<221> NAME/KEY: misc_feature
<222> LOCATION: (1)..(31)
<223> OTHER INFORMATION: /note="Variant residues given in the sequence
      have no preference with respect to those in the annotations for
      variant positions"

<400> SEQUENCE: 15

Xaa Arg Thr His Gln His Ser Leu Glu Thr Arg Thr Pro Asp Ile Asn
1               5                   10                  15

Pro Ala Trp Tyr Thr Gly Arg Gly Ile Arg Pro Val Gly Arg Ala
            20                  25                  30

<210> SEQ ID NO 16
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: (Dpr(tridec))
<220> FEATURE:
<221> NAME/KEY: VARIANT
<222> LOCATION: (3)..(3)
<223> OTHER INFORMATION: /replace="Ala"
<220> FEATURE:
<221> NAME/KEY: VARIANT
<222> LOCATION: (5)..(5)
<223> OTHER INFORMATION: /replace="Arg"
<220> FEATURE:
<221> NAME/KEY: MOD_RES
<222> LOCATION: (8)..(8)
<223> OTHER INFORMATION: Nle
<220> FEATURE:
<221> NAME/KEY: VARIANT
<222> LOCATION: (21)..(21)
<223> OTHER INFORMATION: /replace="Ala"
<220> FEATURE:
<221> NAME/KEY: VARIANT
<222> LOCATION: (22)..(22)
<223> OTHER INFORMATION: /replace="Ser"
<220> FEATURE:
<221> NAME/KEY: VARIANT
<222> LOCATION: (25)..(25)
```

```
<223> OTHER INFORMATION: /replace="Ala" or "phenylglycine"
<220> FEATURE:
<221> NAME/KEY: VARIANT
<222> LOCATION: (28)..(28)
<223> OTHER INFORMATION: /replace="phenylglycine"
<220> FEATURE:
<221> NAME/KEY: MOD_RES
<222> LOCATION: (31)..(31)
<223> OTHER INFORMATION: 1-Nal
<220> FEATURE:
<221> NAME/KEY: misc_feature
<222> LOCATION: (31)..(31)
<223> OTHER INFORMATION: /note="C-term NH2"
<220> FEATURE:
<221> NAME/KEY: misc_feature
<222> LOCATION: (1)..(31)
<223> OTHER INFORMATION: /note="Variant residues given in the sequence
      have no preference with respect to those in the annotations for
      variant positions"

<400> SEQUENCE: 16

Xaa Arg Thr His Gln His Ser Leu Glu Thr Arg Thr Pro Asp Ile Asn
1               5                   10                  15

Pro Ala Trp Tyr Thr Gly Arg Gly Ile Arg Pro Val Gly Arg Ala
            20                  25                  30

<210> SEQ ID NO 17
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: (Dpr(myr))
<220> FEATURE:
<221> NAME/KEY: VARIANT
<222> LOCATION: (3)..(3)
<223> OTHER INFORMATION: /replace="Ala"
<220> FEATURE:
<221> NAME/KEY: VARIANT
<222> LOCATION: (5)..(5)
<223> OTHER INFORMATION: /replace="Arg"
<220> FEATURE:
<221> NAME/KEY: MOD_RES
<222> LOCATION: (8)..(8)
<223> OTHER INFORMATION: Nle
<220> FEATURE:
<221> NAME/KEY: VARIANT
<222> LOCATION: (21)..(21)
<223> OTHER INFORMATION: /replace="Ala"
<220> FEATURE:
<221> NAME/KEY: VARIANT
<222> LOCATION: (22)..(22)
<223> OTHER INFORMATION: /replace="Ser"
<220> FEATURE:
<221> NAME/KEY: VARIANT
<222> LOCATION: (25)..(25)
<223> OTHER INFORMATION: /replace="Ala" or "phenylglycine"
<220> FEATURE:
<221> NAME/KEY: VARIANT
<222> LOCATION: (28)..(28)
<223> OTHER INFORMATION: /replace="phenylglycine"
<220> FEATURE:
<221> NAME/KEY: MOD_RES
<222> LOCATION: (31)..(31)
<223> OTHER INFORMATION: 1-Nal
<220> FEATURE:
<221> NAME/KEY: misc_feature
<222> LOCATION: (31)..(31)
<223> OTHER INFORMATION: /note="C-term NH2"
<220> FEATURE:
<221> NAME/KEY: misc_feature
```

```
<222> LOCATION: (1)..(31)
<223> OTHER INFORMATION: /note="Variant residues given in the sequence
      have no preference with respect to those in the annotations for
      variant positions"

<400> SEQUENCE: 17

Xaa Arg Thr His Gln His Ser Leu Glu Thr Arg Thr Pro Asp Ile Asn
1               5                   10                  15

Pro Ala Trp Tyr Thr Gly Arg Gly Ile Arg Pro Val Gly Arg Ala
            20                  25                  30

<210> SEQ ID NO 18
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: (Dpr(palm))
<220> FEATURE:
<221> NAME/KEY: VARIANT
<222> LOCATION: (3)..(3)
<223> OTHER INFORMATION: /replace="Ala"
<220> FEATURE:
<221> NAME/KEY: VARIANT
<222> LOCATION: (5)..(5)
<223> OTHER INFORMATION: /replace="Arg"
<220> FEATURE:
<221> NAME/KEY: MOD_RES
<222> LOCATION: (8)..(8)
<223> OTHER INFORMATION: Nle
<220> FEATURE:
<221> NAME/KEY: VARIANT
<222> LOCATION: (21)..(21)
<223> OTHER INFORMATION: /replace="Ala"
<220> FEATURE:
<221> NAME/KEY: VARIANT
<222> LOCATION: (22)..(22)
<223> OTHER INFORMATION: /replace="Ser"
<220> FEATURE:
<221> NAME/KEY: VARIANT
<222> LOCATION: (25)..(25)
<223> OTHER INFORMATION: /replace="Ala" or "phenylglycine"
<220> FEATURE:
<221> NAME/KEY: VARIANT
<222> LOCATION: (28)..(28)
<223> OTHER INFORMATION: /replace="phenylglycine"
<220> FEATURE:
<221> NAME/KEY: MOD_RES
<222> LOCATION: (31)..(31)
<223> OTHER INFORMATION: 1-Nal
<220> FEATURE:
<221> NAME/KEY: misc_feature
<222> LOCATION: (31)..(31)
<223> OTHER INFORMATION: /note="C-term NH2"
<220> FEATURE:
<221> NAME/KEY: misc_feature
<222> LOCATION: (1)..(31)
<223> OTHER INFORMATION: /note="Variant residues given in the sequence
      have no preference with respect to those in the annotations for
      variant positions"

<400> SEQUENCE: 18

Xaa Arg Thr His Gln His Ser Leu Glu Thr Arg Thr Pro Asp Ile Asn
1               5                   10                  15

Pro Ala Trp Tyr Thr Gly Arg Gly Ile Arg Pro Val Gly Arg Ala
            20                  25                  30

<210> SEQ ID NO 19
```

```
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term (myr)"
<220> FEATURE:
<221> NAME/KEY: VARIANT
<222> LOCATION: (10)..(10)
<223> OTHER INFORMATION: /replace="Ala"
<220> FEATURE:
<221> NAME/KEY: VARIANT
<222> LOCATION: (11)..(11)
<223> OTHER INFORMATION: /replace="Ser"
<220> FEATURE:
<221> NAME/KEY: VARIANT
<222> LOCATION: (14)..(14)
<223> OTHER INFORMATION: /replace="Ala" or "phenylglycine"
<220> FEATURE:
<221> NAME/KEY: VARIANT
<222> LOCATION: (17)..(17)
<223> OTHER INFORMATION: /replace="phenylglycine"
<220> FEATURE:
<221> NAME/KEY: MOD_RES
<222> LOCATION: (20)..(20)
<223> OTHER INFORMATION: 1-Nal
<220> FEATURE:
<221> NAME/KEY: misc_feature
<222> LOCATION: (20)..(20)
<223> OTHER INFORMATION: /note="C-term NH2"
<220> FEATURE:
<221> NAME/KEY: misc_feature
<222> LOCATION: (1)..(20)
<223> OTHER INFORMATION: /note="Variant residues given in the sequence
      have no preference with respect to those in the annotations for
      variant positions"

<400> SEQUENCE: 19

Thr Pro Asp Ile Asn Pro Ala Trp Tyr Thr Gly Arg Gly Ile Arg Pro
1               5                   10                  15

Val Gly Arg Ala
            20

<210> SEQ ID NO 20
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term (palm)"
<220> FEATURE:
<221> NAME/KEY: VARIANT
<222> LOCATION: (10)..(10)
<223> OTHER INFORMATION: /replace="Ala"
<220> FEATURE:
<221> NAME/KEY: VARIANT
<222> LOCATION: (11)..(11)
<223> OTHER INFORMATION: /replace="Ser"
<220> FEATURE:
<221> NAME/KEY: VARIANT
<222> LOCATION: (14)..(14)
<223> OTHER INFORMATION: /replace="Ala" or "phenylglycine"
<220> FEATURE:
<221> NAME/KEY: VARIANT
<222> LOCATION: (17)..(17)
<223> OTHER INFORMATION: /replace="phenylglycine"
```

```
<220> FEATURE:
<221> NAME/KEY: MOD_RES
<222> LOCATION: (20)..(20)
<223> OTHER INFORMATION: 1-Nal
<220> FEATURE:
<221> NAME/KEY: misc_feature
<222> LOCATION: (20)..(20)
<223> OTHER INFORMATION: /note="C-term NH2"
<220> FEATURE:
<221> NAME/KEY: misc_feature
<222> LOCATION: (1)..(20)
<223> OTHER INFORMATION: /note="Variant residues given in the sequence
      have no preference with respect to those in the annotations for
      variant positions"

<400> SEQUENCE: 20

Thr Pro Asp Ile Asn Pro Ala Trp Tyr Thr Gly Arg Gly Ile Arg Pro
1               5                   10                  15

Val Gly Arg Ala
            20

<210> SEQ ID NO 21
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: (Dpr(oct))
<220> FEATURE:
<221> NAME/KEY: VARIANT
<222> LOCATION: (3)..(3)
<223> OTHER INFORMATION: /replace="Ala"
<220> FEATURE:
<221> NAME/KEY: VARIANT
<222> LOCATION: (5)..(5)
<223> OTHER INFORMATION: /replace="Arg"
<220> FEATURE:
<221> NAME/KEY: MOD_RES
<222> LOCATION: (8)..(8)
<223> OTHER INFORMATION: Nle
<220> FEATURE:
<221> NAME/KEY: VARIANT
<222> LOCATION: (21)..(21)
<223> OTHER INFORMATION: /replace="Ala"
<220> FEATURE:
<221> NAME/KEY: VARIANT
<222> LOCATION: (22)..(22)
<223> OTHER INFORMATION: /replace="Ser"
<220> FEATURE:
<221> NAME/KEY: misc_feature
<222> LOCATION: (31)..(31)
<223> OTHER INFORMATION: /note="C-term NH2"
<220> FEATURE:
<221> NAME/KEY: misc_feature
<222> LOCATION: (1)..(31)
<223> OTHER INFORMATION: /note="Variant residues given in the sequence
      have no preference with respect to those in the annotations for
      variant positions"

<400> SEQUENCE: 21

Xaa Arg Thr His Gln His Ser Leu Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 22
<211> LENGTH: 31
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: (Dpr(dodec))
<220> FEATURE:
<221> NAME/KEY: VARIANT
<222> LOCATION: (3)..(3)
<223> OTHER INFORMATION: /replace="Ala"
<220> FEATURE:
<221> NAME/KEY: VARIANT
<222> LOCATION: (5)..(5)
<223> OTHER INFORMATION: /replace="Arg"
<220> FEATURE:
<221> NAME/KEY: MOD_RES
<222> LOCATION: (8)..(8)
<223> OTHER INFORMATION: Nle
<220> FEATURE:
<221> NAME/KEY: VARIANT
<222> LOCATION: (21)..(21)
<223> OTHER INFORMATION: /replace="Ala"
<220> FEATURE:
<221> NAME/KEY: VARIANT
<222> LOCATION: (22)..(22)
<223> OTHER INFORMATION: /replace="Ser"
<220> FEATURE:
<221> NAME/KEY: misc_feature
<222> LOCATION: (31)..(31)
<223> OTHER INFORMATION: /note="C-term NH2"
<220> FEATURE:
<221> NAME/KEY: misc_feature
<222> LOCATION: (1)..(31)
<223> OTHER INFORMATION: /note="Variant residues given in the sequence
      have no preference with respect to those in the annotations for
      variant positions"

<400> SEQUENCE: 22

Xaa Arg Thr His Gln His Ser Leu Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 23
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: (Dpr(tridec))
<220> FEATURE:
<221> NAME/KEY: VARIANT
<222> LOCATION: (3)..(3)
<223> OTHER INFORMATION: /replace="Ala"
<220> FEATURE:
<221> NAME/KEY: VARIANT
<222> LOCATION: (5)..(5)
<223> OTHER INFORMATION: /replace="Arg"
<220> FEATURE:
<221> NAME/KEY: MOD_RES
<222> LOCATION: (8)..(8)
<223> OTHER INFORMATION: Nle
<220> FEATURE:
<221> NAME/KEY: VARIANT
<222> LOCATION: (21)..(21)
<223> OTHER INFORMATION: /replace="Ala"
<220> FEATURE:
<221> NAME/KEY: VARIANT
```

```
<222> LOCATION: (22)..(22)
<223> OTHER INFORMATION: /replace="Ser"
<220> FEATURE:
<221> NAME/KEY: misc_feature
<222> LOCATION: (31)..(31)
<223> OTHER INFORMATION: /note="C-term NH2"
<220> FEATURE:
<221> NAME/KEY: misc_feature
<222> LOCATION: (1)..(31)
<223> OTHER INFORMATION: /note="Variant residues given in the sequence
      have no preference with respect to those in the annotations for
      variant positions"

<400> SEQUENCE: 23

Xaa Arg Thr His Gln His Ser Leu Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 24
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: (Dpr(myr))
<220> FEATURE:
<221> NAME/KEY: VARIANT
<222> LOCATION: (3)..(3)
<223> OTHER INFORMATION: /replace="Ala"
<220> FEATURE:
<221> NAME/KEY: VARIANT
<222> LOCATION: (5)..(5)
<223> OTHER INFORMATION: /replace="Arg"
<220> FEATURE:
<221> NAME/KEY: MOD_RES
<222> LOCATION: (8)..(8)
<223> OTHER INFORMATION: Nle
<220> FEATURE:
<221> NAME/KEY: VARIANT
<222> LOCATION: (21)..(21)
<223> OTHER INFORMATION: /replace="Ala"
<220> FEATURE:
<221> NAME/KEY: VARIANT
<222> LOCATION: (22)..(22)
<223> OTHER INFORMATION: /replace="Ser"
<220> FEATURE:
<221> NAME/KEY: misc_feature
<222> LOCATION: (31)..(31)
<223> OTHER INFORMATION: /note="C-term NH2"
<220> FEATURE:
<221> NAME/KEY: misc_feature
<222> LOCATION: (1)..(31)
<223> OTHER INFORMATION: /note="Variant residues given in the sequence
      have no preference with respect to those in the annotations for
      variant positions"

<400> SEQUENCE: 24

Xaa Arg Thr His Gln His Ser Leu Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 25
<211> LENGTH: 31
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: (Dpr(palm))
<220> FEATURE:
<221> NAME/KEY: VARIANT
<222> LOCATION: (3)..(3)
<223> OTHER INFORMATION: /replace="Ala"
<220> FEATURE:
<221> NAME/KEY: VARIANT
<222> LOCATION: (5)..(5)
<223> OTHER INFORMATION: /replace="Arg"
<220> FEATURE:
<221> NAME/KEY: MOD_RES
<222> LOCATION: (8)..(8)
<223> OTHER INFORMATION: Nle
<220> FEATURE:
<221> NAME/KEY: VARIANT
<222> LOCATION: (21)..(21)
<223> OTHER INFORMATION: /replace="Ala"
<220> FEATURE:
<221> NAME/KEY: VARIANT
<222> LOCATION: (22)..(22)
<223> OTHER INFORMATION: /replace="Ser"
<220> FEATURE:
<221> NAME/KEY: misc_feature
<222> LOCATION: (31)..(31)
<223> OTHER INFORMATION: /note="C-term NH2"
<220> FEATURE:
<221> NAME/KEY: misc_feature
<222> LOCATION: (1)..(31)
<223> OTHER INFORMATION: /note="Variant residues given in the sequence
      have no preference with respect to those in the annotations for
      variant positions"

<400> SEQUENCE: 25

Xaa Arg Thr His Gln His Ser Leu Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 26
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term (myr)"
<220> FEATURE:
<221> NAME/KEY: VARIANT
<222> LOCATION: (10)..(10)
<223> OTHER INFORMATION: /replace="Ala"
<220> FEATURE:
<221> NAME/KEY: VARIANT
<222> LOCATION: (11)..(11)
<223> OTHER INFORMATION: /replace="Ser"
<220> FEATURE:
<221> NAME/KEY: misc_feature
<222> LOCATION: (20)..(20)
<223> OTHER INFORMATION: /note="C-term NH2"
<220> FEATURE:
<221> NAME/KEY: misc_feature
<222> LOCATION: (1)..(20)
<223> OTHER INFORMATION: /note="Variant residues given in the sequence
      have no preference with respect to those in the annotations for
      variant positions"

<400> SEQUENCE: 26
```

```
Thr Pro Asp Ile Asn Pro Ala Trp Tyr Thr Gly Arg Gly Ile Arg Pro
1               5                   10                  15

Val Gly Arg Phe
            20

<210> SEQ ID NO 27
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term (palm)"
<220> FEATURE:
<221> NAME/KEY: VARIANT
<222> LOCATION: (10)..(10)
<223> OTHER INFORMATION: /replace="Ala"
<220> FEATURE:
<221> NAME/KEY: VARIANT
<222> LOCATION: (11)..(11)
<223> OTHER INFORMATION: /replace="Ser"
<220> FEATURE:
<221> NAME/KEY: misc_feature
<222> LOCATION: (20)..(20)
<223> OTHER INFORMATION: /note="C-term NH2"
<220> FEATURE:
<221> NAME/KEY: misc_feature
<222> LOCATION: (1)..(20)
<223> OTHER INFORMATION: /note="Variant residues given in the sequence
      have no preference with respect to those in the annotations for
      variant positions"

<400> SEQUENCE: 27

Thr Pro Asp Ile Asn Pro Ala Trp Tyr Thr Gly Arg Gly Ile Arg Pro
1               5                   10                  15

Val Gly Arg Phe
            20

<210> SEQ ID NO 28
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: (Dpr(oct))
<220> FEATURE:
<221> NAME/KEY: VARIANT
<222> LOCATION: (3)..(3)
<223> OTHER INFORMATION: /replace="Ala"
<220> FEATURE:
<221> NAME/KEY: VARIANT
<222> LOCATION: (5)..(5)
<223> OTHER INFORMATION: /replace="Arg"
<220> FEATURE:
<221> NAME/KEY: MOD_RES
<222> LOCATION: (8)..(8)
<223> OTHER INFORMATION: Nle
<220> FEATURE:
<221> NAME/KEY: VARIANT
<222> LOCATION: (21)..(21)
<223> OTHER INFORMATION: /replace="Ala"
<220> FEATURE:
<221> NAME/KEY: VARIANT
<222> LOCATION: (22)..(22)
```

```
<223> OTHER INFORMATION: /replace="Ser"
<220> FEATURE:
<221> NAME/KEY: MOD_RES
<222> LOCATION: (31)..(31)
<223> OTHER INFORMATION: 1-Nal
<220> FEATURE:
<221> NAME/KEY: misc_feature
<222> LOCATION: (31)..(31)
<223> OTHER INFORMATION: /note="C-term NH2"
<220> FEATURE:
<221> NAME/KEY: misc_feature
<222> LOCATION: (1)..(31)
<223> OTHER INFORMATION: /note="Variant residues given in the sequence
      have no preference with respect to those in the annotations for
      variant positions"

<400> SEQUENCE: 28

Xaa Arg Thr His Gln His Ser Leu Glu Thr Arg Thr Pro Asp Ile Asn
1               5                   10                  15

Pro Ala Trp Tyr Thr Gly Arg Gly Ile Arg Pro Val Gly Arg Ala
            20                  25                  30

<210> SEQ ID NO 29
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: (Dpr(dodec))
<220> FEATURE:
<221> NAME/KEY: VARIANT
<222> LOCATION: (3)..(3)
<223> OTHER INFORMATION: /replace="Ala"
<220> FEATURE:
<221> NAME/KEY: VARIANT
<222> LOCATION: (5)..(5)
<223> OTHER INFORMATION: /replace="Arg"
<220> FEATURE:
<221> NAME/KEY: MOD_RES
<222> LOCATION: (8)..(8)
<223> OTHER INFORMATION: Nle
<220> FEATURE:
<221> NAME/KEY: VARIANT
<222> LOCATION: (21)..(21)
<223> OTHER INFORMATION: /replace="Ala"
<220> FEATURE:
<221> NAME/KEY: VARIANT
<222> LOCATION: (22)..(22)
<223> OTHER INFORMATION: /replace="Ser"
<220> FEATURE:
<221> NAME/KEY: MOD_RES
<222> LOCATION: (31)..(31)
<223> OTHER INFORMATION: 1-Nal
<220> FEATURE:
<221> NAME/KEY: misc_feature
<222> LOCATION: (31)..(31)
<223> OTHER INFORMATION: /note="C-term NH2"
<220> FEATURE:
<221> NAME/KEY: misc_feature
<222> LOCATION: (1)..(31)
<223> OTHER INFORMATION: /note="Variant residues given in the sequence
      have no preference with respect to those in the annotations for
      variant positions"

<400> SEQUENCE: 29

Xaa Arg Thr His Gln His Ser Leu Glu Thr Arg Thr Pro Asp Ile Asn
1               5                   10                  15

Pro Ala Trp Tyr Thr Gly Arg Gly Ile Arg Pro Val Gly Arg Ala
            20                  25                  30
```

```
<210> SEQ ID NO 30
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: (Dpr(tridec))
<220> FEATURE:
<221> NAME/KEY: VARIANT
<222> LOCATION: (3)..(3)
<223> OTHER INFORMATION: /replace="Ala"
<220> FEATURE:
<221> NAME/KEY: VARIANT
<222> LOCATION: (5)..(5)
<223> OTHER INFORMATION: /replace="Arg"
<220> FEATURE:
<221> NAME/KEY: MOD_RES
<222> LOCATION: (8)..(8)
<223> OTHER INFORMATION: Nle
<220> FEATURE:
<221> NAME/KEY: VARIANT
<222> LOCATION: (21)..(21)
<223> OTHER INFORMATION: /replace="Ala"
<220> FEATURE:
<221> NAME/KEY: VARIANT
<222> LOCATION: (22)..(22)
<223> OTHER INFORMATION: /replace="Ser"
<220> FEATURE:
<221> NAME/KEY: MOD_RES
<222> LOCATION: (31)..(31)
<223> OTHER INFORMATION: 1-Nal
<220> FEATURE:
<221> NAME/KEY: misc_feature
<222> LOCATION: (31)..(31)
<223> OTHER INFORMATION: /note="C-term NH2"
<220> FEATURE:
<221> NAME/KEY: misc_feature
<222> LOCATION: (1)..(31)
<223> OTHER INFORMATION: /note="Variant residues given in the sequence
      have no preference with respect to those in the annotations for
      variant positions"

<400> SEQUENCE: 30

Xaa Arg Thr His Gln His Ser Leu Glu Thr Arg Thr Pro Asp Ile Asn
1               5                   10                  15

Pro Ala Trp Tyr Thr Gly Arg Gly Ile Arg Pro Val Gly Arg Ala
            20                  25                  30

<210> SEQ ID NO 31
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: (Dpr(myr))
<220> FEATURE:
<221> NAME/KEY: VARIANT
<222> LOCATION: (3)..(3)
<223> OTHER INFORMATION: /replace="Ala"
<220> FEATURE:
<221> NAME/KEY: VARIANT
<222> LOCATION: (5)..(5)
<223> OTHER INFORMATION: /replace="Arg"
<220> FEATURE:
```

```
<221> NAME/KEY: MOD_RES
<222> LOCATION: (8)..(8)
<223> OTHER INFORMATION: Nle
<220> FEATURE:
<221> NAME/KEY: VARIANT
<222> LOCATION: (21)..(21)
<223> OTHER INFORMATION: /replace="Ala"
<220> FEATURE:
<221> NAME/KEY: VARIANT
<222> LOCATION: (22)..(22)
<223> OTHER INFORMATION: /replace="Ser"
<220> FEATURE:
<221> NAME/KEY: MOD_RES
<222> LOCATION: (31)..(31)
<223> OTHER INFORMATION: 1-Nal
<220> FEATURE:
<221> NAME/KEY: misc_feature
<222> LOCATION: (31)..(31)
<223> OTHER INFORMATION: /note="C-term NH2"
<220> FEATURE:
<221> NAME/KEY: misc_feature
<222> LOCATION: (1)..(31)
<223> OTHER INFORMATION: /note="Variant residues given in the sequence
      have no preference with respect to those in the annotations for
      variant positions"

<400> SEQUENCE: 31

Xaa Arg Thr His Gln His Ser Leu Glu Thr Arg Thr Pro Asp Ile Asn
1               5                   10                  15

Pro Ala Trp Tyr Thr Gly Arg Gly Ile Arg Pro Val Gly Arg Ala
            20                  25                  30

<210> SEQ ID NO 32
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: (Dpr(palm))
<220> FEATURE:
<221> NAME/KEY: VARIANT
<222> LOCATION: (3)..(3)
<223> OTHER INFORMATION: /replace="Ala"
<220> FEATURE:
<221> NAME/KEY: VARIANT
<222> LOCATION: (5)..(5)
<223> OTHER INFORMATION: /replace="Arg"
<220> FEATURE:
<221> NAME/KEY: MOD_RES
<222> LOCATION: (8)..(8)
<223> OTHER INFORMATION: Nle
<220> FEATURE:
<221> NAME/KEY: VARIANT
<222> LOCATION: (21)..(21)
<223> OTHER INFORMATION: /replace="Ala"
<220> FEATURE:
<221> NAME/KEY: VARIANT
<222> LOCATION: (22)..(22)
<223> OTHER INFORMATION: /replace="Ser"
<220> FEATURE:
<221> NAME/KEY: MOD_RES
<222> LOCATION: (31)..(31)
<223> OTHER INFORMATION: 1-Nal
<220> FEATURE:
<221> NAME/KEY: misc_feature
<222> LOCATION: (31)..(31)
<223> OTHER INFORMATION: /note="C-term NH2"
<220> FEATURE:
<221> NAME/KEY: misc_feature
<222> LOCATION: (1)..(31)
<223> OTHER INFORMATION: /note="Variant residues given in the sequence
``` have no preference with respect to those in the annotations for
variant positions"

<400> SEQUENCE: 32

Xaa Arg Thr His Gln His Ser Leu Glu Thr Arg Thr Pro Asp Ile Asn
1               5                   10                  15

Pro Ala Trp Tyr Thr Gly Arg Gly Ile Arg Pro Val Gly Arg Ala
            20                  25                  30

<210> SEQ ID NO 33
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term (myr)"
<220> FEATURE:
<221> NAME/KEY: VARIANT
<222> LOCATION: (10)..(10)
<223> OTHER INFORMATION: /replace="Ala"
<220> FEATURE:
<221> NAME/KEY: VARIANT
<222> LOCATION: (11)..(11)
<223> OTHER INFORMATION: /replace="Ser"
<220> FEATURE:
<221> NAME/KEY: MOD_RES
<222> LOCATION: (20)..(20)
<223> OTHER INFORMATION: 1-Nal
<220> FEATURE:
<221> NAME/KEY: misc_feature
<222> LOCATION: (20)..(20)
<223> OTHER INFORMATION: /note="C-term NH2"
<220> FEATURE:
<221> NAME/KEY: misc_feature
<222> LOCATION: (1)..(20)
<223> OTHER INFORMATION: /note="Variant residues given in the sequence
      have no preference with respect to those in the annotations for
      variant positions"

<400> SEQUENCE: 33

Thr Pro Asp Ile Asn Pro Ala Trp Tyr Thr Gly Arg Gly Ile Arg Pro
1               5                   10                  15

Val Gly Arg Ala
            20

<210> SEQ ID NO 34
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term (palm)"
<220> FEATURE:
<221> NAME/KEY: VARIANT
<222> LOCATION: (10)..(10)
<223> OTHER INFORMATION: /replace="Ala"
<220> FEATURE:
<221> NAME/KEY: VARIANT
<222> LOCATION: (11)..(11)
<223> OTHER INFORMATION: /replace="Ser"
<220> FEATURE:
<221> NAME/KEY: MOD_RES
<222> LOCATION: (20)..(20)

```
<223> OTHER INFORMATION: 1-Nal
<220> FEATURE:
<221> NAME/KEY: misc_feature
<222> LOCATION: (20)..(20)
<223> OTHER INFORMATION: /note="C-term NH2"
<220> FEATURE:
<221> NAME/KEY: misc_feature
<222> LOCATION: (1)..(20)
<223> OTHER INFORMATION: /note="Variant residues given in the sequence
      have no preference with respect to those in the annotations for
      variant positions"

<400> SEQUENCE: 34

Thr Pro Asp Ile Asn Pro Ala Trp Tyr Thr Gly Arg Gly Ile Arg Pro
1               5                  10                  15

Val Gly Arg Ala
            20

<210> SEQ ID NO 35
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term palmitic acid or myristic acid"
<220> FEATURE:
<221> NAME/KEY: misc_feature
<222> LOCATION: (31)..(31)
<223> OTHER INFORMATION: /note="C-term NH2"

<400> SEQUENCE: 35

Ser Arg Ala His Gln His Ser Met Glu Thr Arg Thr Pro Asp Ile Asn
1               5                  10                  15

Pro Ala Trp Tyr Thr Gly Arg Gly Ile Arg Pro Val Gly Arg Phe
            20                  25                  30

<210> SEQ ID NO 36
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term palmitic acid or myristic acid"
<220> FEATURE:
<221> NAME/KEY: misc_feature
<222> LOCATION: (31)..(31)
<223> OTHER INFORMATION: /note="C-term NH2"

<400> SEQUENCE: 36

Ser Arg Thr His Arg His Ser Met Glu Ile Arg Thr Pro Asp Ile Asn
1               5                  10                  15

Pro Ala Trp Tyr Ala Ser Arg Gly Ile Arg Pro Val Gly Arg Phe
            20                  25                  30

<210> SEQ ID NO 37
<211> LENGTH: 31
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term (N-palm)"
<220> FEATURE:
<221> NAME/KEY: misc_feature
<222> LOCATION: (31)..(31)
<223> OTHER INFORMATION: /note="C-term NHMe"

<400> SEQUENCE: 37

Ser Arg Thr His Arg His Ser Met Glu Ile Arg Thr Pro Asp Ile Asn
1               5                   10                  15

Pro Ala Trp Tyr Ala Ser Arg Gly Ile Arg Pro Val Gly Arg Phe
            20                  25                  30

<210> SEQ ID NO 38
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term (N-palm)"
<220> FEATURE:
<221> NAME/KEY: misc_feature
<222> LOCATION: (31)..(31)
<223> OTHER INFORMATION: /note="C-term NOMe"

<400> SEQUENCE: 38

Ser Arg Thr His Arg His Ser Met Glu Ile Arg Thr Pro Asp Ile Asn
1               5                   10                  15

Pro Ala Trp Tyr Ala Ser Arg Gly Ile Arg Pro Val Gly Arg Phe
            20                  25                  30

<210> SEQ ID NO 39
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term (N-myr)"
<220> FEATURE:
<221> NAME/KEY: misc_feature
<222> LOCATION: (20)..(20)
<223> OTHER INFORMATION: /note="C-term NH2"

<400> SEQUENCE: 39

Thr Pro Asp Ile Asn Pro Ala Trp Tyr Thr Gly Arg Gly Ile Arg Pro
1               5                   10                  15

Val Gly Arg Phe
            20

<210> SEQ ID NO 40
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
```

```
        Synthetic peptide"
<220> FEATURE:
<221> NAME/KEY: misc_feature
<222> LOCATION: (1)..(1)
<223> OTHER INFORMATION: /note="N-term (N-myr)"
<220> FEATURE:
<221> NAME/KEY: misc_feature
<222> LOCATION: (20)..(20)
<223> OTHER INFORMATION: /note="C-term NH2"

<400> SEQUENCE: 40

Thr Pro Asp Ile Asn Pro Ala Trp Tyr Ala Ser Arg Gly Ile Arg Pro
1               5                   10                  15

Val Gly Arg Phe
            20

<210> SEQ ID NO 41
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term (N-oct)"
<220> FEATURE:
<221> NAME/KEY: misc_feature
<222> LOCATION: (20)..(20)
<223> OTHER INFORMATION: /note="C-term NH2"

<400> SEQUENCE: 41

Thr Pro Asp Ile Asn Pro Ala Trp Tyr Ala Ser Arg Gly Ile Arg Pro
1               5                   10                  15

Val Gly Arg Phe
            20

<210> SEQ ID NO 42
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term (N-dec)"
<220> FEATURE:
<221> NAME/KEY: misc_feature
<222> LOCATION: (20)..(20)
<223> OTHER INFORMATION: /note="C-term NH2"

<400> SEQUENCE: 42

Thr Pro Asp Ile Asn Pro Ala Trp Tyr Ala Ser Arg Gly Ile Arg Pro
1               5                   10                  15

Val Gly Arg Phe
            20

<210> SEQ ID NO 43
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<220> FEATURE:
<221> NAME/KEY: misc_feature
<222> LOCATION: (1)..(1)
<223> OTHER INFORMATION: /note="N-term (N-dodec)"
<220> FEATURE:
<221> NAME/KEY: misc_feature
<222> LOCATION: (20)..(20)
<223> OTHER INFORMATION: /note="C-term NH2"

<400> SEQUENCE: 43

Thr Pro Asp Ile Asn Pro Ala Trp Tyr Ala Ser Arg Gly Ile Arg Pro
1               5                   10                  15

Val Gly Arg Phe
            20

<210> SEQ ID NO 44
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term palmitic acid, myristic acid or
      stearic acid"
<220> FEATURE:
<221> NAME/KEY: MOD_RES
<222> LOCATION: (8)..(8)
<223> OTHER INFORMATION: Nle
<220> FEATURE:
<221> NAME/KEY: misc_feature
<222> LOCATION: (31)..(31)
<223> OTHER INFORMATION: /note="C-term NH2"

<400> SEQUENCE: 44

Ser Arg Ala His Gln His Ser Leu Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 45
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term palmitic acid or myristic acid"
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (31)..(31)
<223> OTHER INFORMATION: 1-Nal
<220> FEATURE:
<221> NAME/KEY: misc_feature
<222> LOCATION: (31)..(31)
<223> OTHER INFORMATION: /note="C-term NH2"

<400> SEQUENCE: 45

Ser Arg Ala His Gln His Ser Leu Glu Thr Arg Thr Pro Asp Ile Asn
1               5                   10                  15
```

Pro Ala Trp Tyr Thr Gly Arg Gly Ile Arg Pro Val Gly Arg Ala
            20                  25                  30

<210> SEQ ID NO 46
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term palmitic acid or myristic acid"
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (31)..(31)
<223> OTHER INFORMATION: PheCl2
<220> FEATURE:
<221> NAME/KEY: misc_feature
<222> LOCATION: (31)..(31)
<223> OTHER INFORMATION: /note="C-term NH2"

<400> SEQUENCE: 46

Ser Arg Ala His Gln His Ser Leu Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 47
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term palmitic acid or myristic acid"
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (31)..(31)
<223> OTHER INFORMATION: PheNO2
<220> FEATURE:
<221> NAME/KEY: misc_feature
<222> LOCATION: (31)..(31)
<223> OTHER INFORMATION: /note="C-term NH2"

<400> SEQUENCE: 47

Ser Arg Ala His Gln His Ser Leu Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 48
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:

```
  Synthetic polypeptide"
<220> FEATURE:
<221> NAME/KEY: misc_feature
<222> LOCATION: (1)..(1)
<223> OTHER INFORMATION: /note="N-term palmitic acid or myristic acid"
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (31)..(31)
<223> OTHER INFORMATION: PheF5
<220> FEATURE:
<221> NAME/KEY: misc_feature
<222> LOCATION: (31)..(31)
<223> OTHER INFORMATION: /note="C-term NH2"

<400> SEQUENCE: 48

Ser Arg Ala His Gln His Ser Leu Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 49
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term palmitic acid or myristic acid"
<220> FEATURE:
<221> NAME/KEY: MOD_RES
<222> LOCATION: (8)..(8)
<223> OTHER INFORMATION: Nle
<220> FEATURE:
<221> NAME/KEY: misc_feature
<222> LOCATION: (31)..(31)
<223> OTHER INFORMATION: /note="C-term NH2"

<400> SEQUENCE: 49

Ser Arg Ala His Gln His Ser Leu Glu Thr Arg Thr Pro Asp Ile Asn
1               5                   10                  15

Pro Ala Trp Tyr Thr Gly Arg Gly Ile Arg Pro Val Gly Arg Tyr
            20                  25                  30

<210> SEQ ID NO 50
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term palmitic acid or myristic acid"
<220> FEATURE:
<221> NAME/KEY: MOD_RES
<222> LOCATION: (8)..(8)
<223> OTHER INFORMATION: Nle
<220> FEATURE:
<221> NAME/KEY: misc_feature
<222> LOCATION: (31)..(31)
<223> OTHER INFORMATION: /note="C-term NH2"

<400> SEQUENCE: 50
```

```
Ser Arg Ala His Arg His Ser Leu Glu Ile Arg Thr Pro Asp Ile Asn
1               5                   10                  15

Pro Ala Trp Tyr Ala Ser Arg Gly Ile Arg Pro Val Gly Arg Tyr
                20                  25                  30

<210> SEQ ID NO 51
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term (N-myr)"
<220> FEATURE:
<221> NAME/KEY: MOD_RES
<222> LOCATION: (1)..(1)
<223> OTHER INFORMATION: Nle
<220> FEATURE:
<221> NAME/KEY: misc_feature
<222> LOCATION: (24)..(24)
<223> OTHER INFORMATION: /note="C-term NH2"

<400> SEQUENCE: 51

Leu Glu Thr Arg Thr Pro Asp Ile Asn Pro Ala Trp Tyr Thr Gly Arg
1               5                   10                  15

Gly Ile Arg Pro Val Gly Arg Phe
                20

<210> SEQ ID NO 52
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term (N-myr)"
<220> FEATURE:
<221> NAME/KEY: misc_feature
<222> LOCATION: (27)..(27)
<223> OTHER INFORMATION: /note="C-term NH2"

<400> SEQUENCE: 52

Gln His Ser Met Glu Thr Arg Thr Pro Asp Ile Asn Pro Ala Trp Tyr
1               5                   10                  15

Thr Gly Arg Gly Ile Arg Pro Val Gly Arg Phe
                20                  25

<210> SEQ ID NO 53
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term (N-myr)"
<220> FEATURE:
<221> NAME/KEY: misc_feature
<222> LOCATION: (27)..(27)
```

<223> OTHER INFORMATION: /note="C-term NH2"

<400> SEQUENCE: 53

Gln His Ser Met Glu Thr Arg Thr Pro Asp Ile Asn Pro Ala Trp Tyr
1               5                   10                  15

Ala Ser Arg Gly Ile Arg Pro Val Gly Arg Phe
            20                  25

<210> SEQ ID NO 54
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term (N-palm)"
<220> FEATURE:
<221> NAME/KEY: misc_feature
<222> LOCATION: (31)..(31)
<223> OTHER INFORMATION: /note="C-term NOMe"

<400> SEQUENCE: 54

Ser Arg Thr His Arg His Ser Met Glu Ile Arg Thr Pro Asp Ile Asn
1               5                   10                  15

Pro Ala Trp Tyr Ala Ser Arg Gly Ile Arg Pro Val Gly Arg Phe
            20                  25                  30

<210> SEQ ID NO 55
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term (palm)"
<220> FEATURE:
<221> NAME/KEY: misc_feature
<222> LOCATION: (31)..(31)
<223> OTHER INFORMATION: /note="C-term NH2"

<400> SEQUENCE: 55

Ser Arg Thr His Arg His Ser Met Glu Ile Arg Thr Pro Asp Ile Asn
1               5                   10                  15

Pro Ala Trp Tyr Ala Ser Arg Gly Ile Arg Pro Val Gly Arg Phe
            20                  25                  30

<210> SEQ ID NO 56
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term (myr)"
<220> FEATURE:
<221> NAME/KEY: misc_feature
<222> LOCATION: (31)..(31)
<223> OTHER INFORMATION: /note="C-term NH2"

```
<400> SEQUENCE: 56

Ser Arg Thr His Arg His Ser Met Glu Ile Arg Thr Pro Asp Ile Asn
1               5                   10                  15

Pro Ala Trp Tyr Ala Ser Arg Gly Ile Arg Pro Val Gly Arg Phe
            20                  25                  30

<210> SEQ ID NO 57
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term palmitic acid or myristic acid"
<220> FEATURE:
<221> NAME/KEY: VARIANT
<222> LOCATION: (10)..(10)
<223> OTHER INFORMATION: /replace="Ala" or "methylalanine"
<220> FEATURE:
<221> NAME/KEY: VARIANT
<222> LOCATION: (11)..(11)
<223> OTHER INFORMATION: /replace="Ser"
<220> FEATURE:
<221> NAME/KEY: misc_feature
<222> LOCATION: (20)..(20)
<223> OTHER INFORMATION: /note="C-term NH2"
<220> FEATURE:
<221> NAME/KEY: misc_feature
<222> LOCATION: (1)..(20)
<223> OTHER INFORMATION: /note="Variant residues given in the sequence
      have no preference with respect to those in the annotations for
      variant positions"

<400> SEQUENCE: 57

Thr Pro Asp Ile Asn Pro Ala Trp Tyr Thr Gly Arg Gly Ile Arg Pro
1               5                   10                  15

Val Gly Arg Phe
            20

<210> SEQ ID NO 58
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term (myr)"
<220> FEATURE:
<221> NAME/KEY: misc_feature
<222> LOCATION: (20)..(20)
<223> OTHER INFORMATION: /note="C-term NH2"

<400> SEQUENCE: 58

Thr Pro Asp Ile Asn Pro Ala Trp Tyr Ala Ser Arg Gly Ile Arg Pro
1               5                   10                  15

Val Gly Arg Phe
            20

<210> SEQ ID NO 59
<211> LENGTH: 7
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (7)..(7)
<223> OTHER INFORMATION: /note="C-term NH2"

<400> SEQUENCE: 59

Ile Arg Pro Val Gly Arg Phe
1               5

<210> SEQ ID NO 60
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: (Dpr)
<220> FEATURE:
<221> NAME/KEY: MOD_RES
<222> LOCATION: (8)..(8)
<223> OTHER INFORMATION: Nle
<220> FEATURE:
<221> NAME/KEY: misc_feature
<222> LOCATION: (31)..(31)
<223> OTHER INFORMATION: /note="C-term NH2"

<400> SEQUENCE: 60

Xaa Arg Ala His Gln His Ser Leu Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 61
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: (Dpr(oct))
<220> FEATURE:
<221> NAME/KEY: MOD_RES
<222> LOCATION: (8)..(8)
<223> OTHER INFORMATION: Nle
<220> FEATURE:
<221> NAME/KEY: misc_feature
<222> LOCATION: (31)..(31)
<223> OTHER INFORMATION: /note="C-term NH2"

<400> SEQUENCE: 61

Xaa Arg Ala His Gln His Ser Leu Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 62
<211> LENGTH: 31
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: (Dpr(dodec))
<220> FEATURE:
<221> NAME/KEY: MOD_RES
<222> LOCATION: (8)..(8)
<223> OTHER INFORMATION: Nle
<220> FEATURE:
<221> NAME/KEY: misc_feature
<222> LOCATION: (31)..(31)
<223> OTHER INFORMATION: /note="C-term NH2"

<400> SEQUENCE: 62

Xaa Arg Ala His Gln His Ser Leu Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 63
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: (Dpr(tridec))
<220> FEATURE:
<221> NAME/KEY: MOD_RES
<222> LOCATION: (8)..(8)
<223> OTHER INFORMATION: Nle
<220> FEATURE:
<221> NAME/KEY: misc_feature
<222> LOCATION: (31)..(31)
<223> OTHER INFORMATION: /note="C-term NH2"

<400> SEQUENCE: 63

Xaa Arg Ala His Gln His Ser Leu Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 64
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: (Dpr(myr))
<220> FEATURE:
<221> NAME/KEY: MOD_RES
<222> LOCATION: (8)..(8)
<223> OTHER INFORMATION: Nle
<220> FEATURE:
<221> NAME/KEY: misc_feature
<222> LOCATION: (31)..(31)
<223> OTHER INFORMATION: /note="C-term NH2"

<400> SEQUENCE: 64
```

```
Xaa Arg Ala His Gln His Ser Leu Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 65
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: (Dpr(palm))
<220> FEATURE:
<221> NAME/KEY: MOD_RES
<222> LOCATION: (8)..(8)
<223> OTHER INFORMATION: Nle
<220> FEATURE:
<221> NAME/KEY: misc_feature
<222> LOCATION: (31)..(31)
<223> OTHER INFORMATION: /note="C-term NH2"

<400> SEQUENCE: 65

Xaa Arg Ala His Gln His Ser Leu Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 66
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: (Dpr)
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (31)..(31)
<223> OTHER INFORMATION: 1-Nal
<220> FEATURE:
<221> NAME/KEY: misc_feature
<222> LOCATION: (31)..(31)
<223> OTHER INFORMATION: /note="C-term NH2"

<400> SEQUENCE: 66

Xaa Arg Ala His Gln His Ser Leu Glu Thr Arg Thr Pro Asp Ile Asn
1               5                   10                  15

Pro Ala Trp Tyr Thr Gly Arg Gly Ile Arg Pro Val Gly Arg Ala
            20                  25                  30

<210> SEQ ID NO 67
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
```

```
   Synthetic polypeptide"
<220> FEATURE:
<221> NAME/KEY: MOD_RES
<222> LOCATION: (1)..(1)
<223> OTHER INFORMATION: (Dpr(oct))
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (31)..(31)
<223> OTHER INFORMATION: 1-Nal
<220> FEATURE:
<221> NAME/KEY: misc_feature
<222> LOCATION: (31)..(31)
<223> OTHER INFORMATION: /note="C-term NH2"

<400> SEQUENCE: 67

Xaa Arg Ala His Gln His Ser Leu Glu Thr Arg Thr Pro Asp Ile Asn
1               5                   10                  15

Pro Ala Trp Tyr Thr Gly Arg Gly Ile Arg Pro Val Gly Arg Ala
            20                  25                  30

<210> SEQ ID NO 68
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: (Dpr(myr))
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (31)..(31)
<223> OTHER INFORMATION: 1-Nal
<220> FEATURE:
<221> NAME/KEY: misc_feature
<222> LOCATION: (31)..(31)
<223> OTHER INFORMATION: /note="C-term NH2"

<400> SEQUENCE: 68

Xaa Arg Ala His Gln His Ser Leu Glu Thr Arg Thr Pro Asp Ile Asn
1               5                   10                  15

Pro Ala Trp Tyr Thr Gly Arg Gly Ile Arg Pro Val Gly Arg Ala
            20                  25                  30

<210> SEQ ID NO 69
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term (myr)"
<220> FEATURE:
<221> NAME/KEY: misc_feature
<222> LOCATION: (20)..(20)
<223> OTHER INFORMATION: /note="C-term NH2"

<400> SEQUENCE: 69
```

```
Thr Pro Asp Ile Asn Pro Ala Trp Tyr Thr Gly Arg Gly Ile Arg Pro
1               5                   10                  15

Val Gly Arg Phe
            20
```

<210> SEQ ID NO 70
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: MOD_RES
<222> LOCATION: (1)..(1)
<223> OTHER INFORMATION: (Dpr)
<220> FEATURE:
<221> NAME/KEY: MOD_RES
<222> LOCATION: (8)..(8)
<223> OTHER INFORMATION: Nle
<220> FEATURE:
<221> NAME/KEY: misc_feature
<222> LOCATION: (31)..(31)
<223> OTHER INFORMATION: /note="C-term NH2"

<400> SEQUENCE: 70

```
Xaa Arg Thr His Arg His Ser Leu Glu Ile Arg Thr Pro Asp Ile Asn
1               5                   10                  15

Pro Ala Trp Tyr Ala Ser Arg Gly Ile Arg Pro Val Gly Arg Phe
            20                  25                  30
```

<210> SEQ ID NO 71
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: MOD_RES
<222> LOCATION: (1)..(1)
<223> OTHER INFORMATION: (Dpr(myr))
<220> FEATURE:
<221> NAME/KEY: MOD_RES
<222> LOCATION: (8)..(8)
<223> OTHER INFORMATION: Nle
<220> FEATURE:
<221> NAME/KEY: misc_feature
<222> LOCATION: (31)..(31)
<223> OTHER INFORMATION: /note="C-term NH2"

<400> SEQUENCE: 71

```
Xaa Arg Thr His Arg His Ser Leu Glu Ile Arg Thr Pro Asp Ile Asn
1               5                   10                  15

Pro Ala Trp Tyr Ala Ser Arg Gly Ile Arg Pro Val Gly Arg Phe
            20                  25                  30
```

<210> SEQ ID NO 72
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: misc_feature
<222> LOCATION: (1)..(1)

```
<223> OTHER INFORMATION: /note="N-term (myr)"
<220> FEATURE:
<221> NAME/KEY: misc_feature
<222> LOCATION: (20)..(20)
<223> OTHER INFORMATION: /note="C-term NH2"

<400> SEQUENCE: 72

Thr Pro Asp Ile Asn Pro Ala Trp Tyr Ala Ser Arg Gly Ile Arg Pro
1               5                   10                  15

Val Gly Arg Phe
            20

<210> SEQ ID NO 73
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term (N-oct)"
<220> FEATURE:
<221> NAME/KEY: MOD_RES
<222> LOCATION: (8)..(8)
<223> OTHER INFORMATION: Nle
<220> FEATURE:
<221> NAME/KEY: misc_feature
<222> LOCATION: (31)..(31)
<223> OTHER INFORMATION: /note="C-term NH2"

<400> SEQUENCE: 73

Ser Arg Ala His Gln His Ser Leu Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 74
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term (N-dec)"
<220> FEATURE:
<221> NAME/KEY: MOD_RES
<222> LOCATION: (8)..(8)
<223> OTHER INFORMATION: Nle
<220> FEATURE:
<221> NAME/KEY: misc_feature
<222> LOCATION: (31)..(31)
<223> OTHER INFORMATION: /note="C-term NH2"

<400> SEQUENCE: 74

Ser Arg Ala His Gln His Ser Leu Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 75
<211> LENGTH: 31
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term (N-dodec)"
<220> FEATURE:
<221> NAME/KEY: MOD_RES
<222> LOCATION: (8)..(8)
<223> OTHER INFORMATION: Nle
<220> FEATURE:
<221> NAME/KEY: misc_feature
<222> LOCATION: (31)..(31)
<223> OTHER INFORMATION: /note="C-term NH2"

<400> SEQUENCE: 75

Ser Arg Ala His Gln His Ser Leu Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 76
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term (N-myr)"
<220> FEATURE:
<221> NAME/KEY: MOD_RES
<222> LOCATION: (8)..(8)
<223> OTHER INFORMATION: Nle
<220> FEATURE:
<221> NAME/KEY: misc_feature
<222> LOCATION: (31)..(31)
<223> OTHER INFORMATION: /note="C-term NH2"

<400> SEQUENCE: 76

Ser Arg Ala His Gln His Ser Leu Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 77
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term (N-palm)"
<220> FEATURE:
<221> NAME/KEY: MOD_RES
<222> LOCATION: (8)..(8)
<223> OTHER INFORMATION: Nle
<220> FEATURE:
<221> NAME/KEY: misc_feature
<222> LOCATION: (31)..(31)
<223> OTHER INFORMATION: /note="C-term NH2"

<400> SEQUENCE: 77
```

Ser Arg Ala His Gln His Ser Leu Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 78
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term (N-stear)"
<220> FEATURE:
<221> NAME/KEY: MOD_RES
<222> LOCATION: (8)..(8)
<223> OTHER INFORMATION: Nle
<220> FEATURE:
<221> NAME/KEY: misc_feature
<222> LOCATION: (31)..(31)
<223> OTHER INFORMATION: /note="C-term NH2"

<400> SEQUENCE: 78

Ser Arg Ala His Gln His Ser Leu Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 79
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term (N-myr)"
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (31)..(31)
<223> OTHER INFORMATION: 1-Nal
<220> FEATURE:
<221> NAME/KEY: misc_feature
<222> LOCATION: (31)..(31)
<223> OTHER INFORMATION: /note="C-term NH2"

<400> SEQUENCE: 79

Ser Arg Ala His Gln His Ser Leu Glu Thr Arg Thr Pro Asp Ile Asn
1               5                   10                  15

Pro Ala Trp Tyr Thr Gly Arg Gly Ile Arg Pro Val Gly Arg Ala
            20                  25                  30

<210> SEQ ID NO 80
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<220> FEATURE:
<221> NAME/KEY: misc_feature
<222> LOCATION: (1)..(1)
<223> OTHER INFORMATION: /note="N-term (N-palm)"
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (31)..(31)
<223> OTHER INFORMATION: 1-Nal
<220> FEATURE:
<221> NAME/KEY: misc_feature
<222> LOCATION: (31)..(31)
<223> OTHER INFORMATION: /note="C-term NH2"

<400> SEQUENCE: 80

Ser Arg Ala His Gln His Ser Leu Glu Thr Arg Thr Pro Asp Ile Asn
1               5                   10                  15

Pro Ala Trp Tyr Thr Gly Arg Gly Ile Arg Pro Val Gly Arg Ala
            20                  25                  30

<210> SEQ ID NO 81
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term (N-myr)"
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (31)..(31)
<223> OTHER INFORMATION: PheCl2
<220> FEATURE:
<221> NAME/KEY: misc_feature
<222> LOCATION: (31)..(31)
<223> OTHER INFORMATION: /note="C-term NH2"

<400> SEQUENCE: 81

Ser Arg Ala His Gln His Ser Leu Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 82
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term (N-palm)"
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (31)..(31)

```
<223> OTHER INFORMATION: PheCl2
<220> FEATURE:
<221> NAME/KEY: misc_feature
<222> LOCATION: (31)..(31)
<223> OTHER INFORMATION: /note="C-term NH2"

<400> SEQUENCE: 82

Ser Arg Ala His Gln His Ser Leu Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 83
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term (N-myr)"
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (31)..(31)
<223> OTHER INFORMATION: PheNO2
<220> FEATURE:
<221> NAME/KEY: misc_feature
<222> LOCATION: (31)..(31)
<223> OTHER INFORMATION: /note="C-term NH2"

<400> SEQUENCE: 83

Ser Arg Ala His Gln His Ser Leu Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 84
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term (N-palm)"
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (31)..(31)
<223> OTHER INFORMATION: PheNO2
<220> FEATURE:
<221> NAME/KEY: misc_feature
<222> LOCATION: (31)..(31)
<223> OTHER INFORMATION: /note="C-term NH2"

<400> SEQUENCE: 84

Ser Arg Ala His Gln His Ser Leu Glu Thr Arg Thr Pro Asp Ile Asn
1               5                   10                  15
```

```
Pro Ala Trp Tyr Thr Gly Arg Gly Ile Arg Pro Val Gly Arg Phe
            20                  25                  30

<210> SEQ ID NO 85
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term (N-palm)"
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (31)..(31)
<223> OTHER INFORMATION: PheF5
<220> FEATURE:
<221> NAME/KEY: misc_feature
<222> LOCATION: (31)..(31)
<223> OTHER INFORMATION: /note="C-term NH2"

<400> SEQUENCE: 85

Ser Arg Ala His Gln His Ser Leu Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 86
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term (N-palm)"
<220> FEATURE:
<221> NAME/KEY: MOD_RES
<222> LOCATION: (8)..(8)
<223> OTHER INFORMATION: Nle
<220> FEATURE:
<221> NAME/KEY: misc_feature
<222> LOCATION: (31)..(31)
<223> OTHER INFORMATION: /note="C-term NH2"

<400> SEQUENCE: 86

Ser Arg Ala His Gln His Ser Leu Glu Thr Arg Thr Pro Asp Ile Asn
1               5                   10                  15

Pro Ala Trp Tyr Thr Gly Arg Gly Ile Arg Pro Val Gly Arg Tyr
            20                  25                  30

<210> SEQ ID NO 87
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
```

```
<223> OTHER INFORMATION: /note="N-term (N-myr)"
<220> FEATURE:
<221> NAME/KEY: MOD_RES
<222> LOCATION: (13)..(13)
<223> OTHER INFORMATION: Sar
<220> FEATURE:
<221> NAME/KEY: misc_feature
<222> LOCATION: (20)..(20)
<223> OTHER INFORMATION: /note="C-term NH2"

<400> SEQUENCE: 87

Thr Pro Asp Ile Asn Pro Ala Trp Tyr Thr Gly Arg Xaa Ile Arg Pro
1               5                   10                  15

Val Gly Arg Phe
            20

<210> SEQ ID NO 88
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term (N-myr)"
<220> FEATURE:
<221> NAME/KEY: MOD_RES
<222> LOCATION: (10)..(10)
<223> OTHER INFORMATION: NMeAla
<220> FEATURE:
<221> NAME/KEY: misc_feature
<222> LOCATION: (20)..(20)
<223> OTHER INFORMATION: /note="C-term NH2"

<400> SEQUENCE: 88

Thr Pro Asp Ile Asn Pro Ala Trp Tyr Ala Ser Arg Gly Ile Arg Pro
1               5                   10                  15

Val Gly Arg Phe
            20

<210> SEQ ID NO 89
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term (N-myr)"
<220> FEATURE:
<221> NAME/KEY: misc_feature
<222> LOCATION: (20)..(20)
<223> OTHER INFORMATION: /note="C-term NH2"

<400> SEQUENCE: 89

Thr Pro Asp Ile Asn Pro Ala Trp Tyr Thr Gly Arg Gly Ala Arg Pro
1               5                   10                  15

Phe Gly Arg Phe
            20

<210> SEQ ID NO 90
<211> LENGTH: 20
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term (N-myr)"
<220> FEATURE:
<221> NAME/KEY: misc_feature
<222> LOCATION: (20)..(20)
<223> OTHER INFORMATION: /note="C-term NH2"

<400> SEQUENCE: 90

Thr Pro Asp Ile Asn Pro Ala Trp Tyr Ala Ser Arg Pro Phe Arg Pro
1               5                   10                  15

Val Gly Arg Phe
            20

<210> SEQ ID NO 91
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term (N-myr)"
<220> FEATURE:
<221> NAME/KEY: MOD_RES
<222> LOCATION: (1)..(1)
<223> OTHER INFORMATION: Nle
<220> FEATURE:
<221> NAME/KEY: misc_feature
<222> LOCATION: (24)..(24)
<223> OTHER INFORMATION: /note="C-term NH2"

<400> SEQUENCE: 91

Leu Glu Thr Arg Thr Pro Asp Ile Asn Pro Ala Trp Tyr Thr Gly Arg
1               5                   10                  15

Gly Ile Arg Pro Val Gly Arg Phe
            20

<210> SEQ ID NO 92
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term (N-myr)"
<220> FEATURE:
<221> NAME/KEY: misc_feature
<222> LOCATION: (27)..(27)
<223> OTHER INFORMATION: /note="C-term NH2"

<400> SEQUENCE: 92

Gln His Ser Met Glu Thr Arg Thr Pro Asp Ile Asn Pro Ala Trp Tyr
1               5                   10                  15

Thr Gly Arg Gly Ile Arg Pro Val Gly Arg Phe
            20                  25

<210> SEQ ID NO 93
```

```
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term (N-oct)"
<220> FEATURE:
<221> NAME/KEY: misc_feature
<222> LOCATION: (20)..(20)
<223> OTHER INFORMATION: /note="C-term NH2"

<400> SEQUENCE: 93

Thr Pro Asp Ile Asn Pro Ala Trp Tyr Ala Ser Arg Gly Ile Arg Pro
1               5                   10                  15

Val Gly Arg Phe
            20

<210> SEQ ID NO 94
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term (N-dec)"
<220> FEATURE:
<221> NAME/KEY: misc_feature
<222> LOCATION: (20)..(20)
<223> OTHER INFORMATION: /note="C-term NH2"

<400> SEQUENCE: 94

Thr Pro Asp Ile Asn Pro Ala Trp Tyr Ala Ser Arg Gly Ile Arg Pro
1               5                   10                  15

Val Gly Arg Phe
            20

<210> SEQ ID NO 95
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term (N-dodec)"
<220> FEATURE:
<221> NAME/KEY: misc_feature
<222> LOCATION: (20)..(20)
<223> OTHER INFORMATION: /note="C-term NH2"

<400> SEQUENCE: 95

Thr Pro Asp Ile Asn Pro Ala Trp Tyr Ala Ser Arg Gly Ile Arg Pro
1               5                   10                  15

Val Gly Arg Phe
            20

<210> SEQ ID NO 96
<211> LENGTH: 20
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term (N-myr)"
<220> FEATURE:
<221> NAME/KEY: misc_feature
<222> LOCATION: (20)..(20)
<223> OTHER INFORMATION: /note="C-term NH2"

<400> SEQUENCE: 96

Thr Pro Asp Ile Asn Pro Ala Trp Tyr Ala Ser Arg Gly Ile Arg Pro
1               5                   10                  15

Val Gly Arg Phe
            20

<210> SEQ ID NO 97
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term (N-myr)"
<220> FEATURE:
<221> NAME/KEY: misc_feature
<222> LOCATION: (31)..(31)
<223> OTHER INFORMATION: /note="C-term NH2"

<400> SEQUENCE: 97

Ser Arg Thr His Arg His Ser Met Glu Ile Arg Thr Pro Asp Ile Asn
1               5                   10                  15

Pro Ala Trp Tyr Ala Ser Arg Gly Ile Arg Pro Val Gly Arg Phe
                20                  25                  30

<210> SEQ ID NO 98
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term (N-palm)"
<220> FEATURE:
<221> NAME/KEY: misc_feature
<222> LOCATION: (31)..(31)
<223> OTHER INFORMATION: /note="C-term NH2"

<400> SEQUENCE: 98

Ser Arg Thr His Arg His Ser Met Glu Ile Arg Thr Pro Asp Ile Asn
1               5                   10                  15

Pro Ala Trp Tyr Ala Ser Arg Gly Ile Arg Pro Val Gly Arg Phe
                20                  25                  30

<210> SEQ ID NO 99
<211> LENGTH: 31
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term (N-palm)"
<220> FEATURE:
<221> NAME/KEY: misc_feature
<222> LOCATION: (31)..(31)
<223> OTHER INFORMATION: /note="C-term NHMe"

<400> SEQUENCE: 99

Ser Arg Thr His Arg His Ser Met Glu Ile Arg Thr Pro Asp Ile Asn
1               5                   10                  15

Pro Ala Trp Tyr Ala Ser Arg Gly Ile Arg Pro Val Gly Arg Phe
            20                  25                  30

<210> SEQ ID NO 100
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term (N-palm)"
<220> FEATURE:
<221> NAME/KEY: misc_feature
<222> LOCATION: (31)..(31)
<223> OTHER INFORMATION: /note="C-term NOMe"

<400> SEQUENCE: 100

Ser Arg Thr His Arg His Ser Met Glu Ile Arg Thr Pro Asp Ile Asn
1               5                   10                  15

Pro Ala Trp Tyr Ala Ser Arg Gly Ile Arg Pro Val Gly Arg Phe
            20                  25                  30

<210> SEQ ID NO 101
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term (N-myr)"
<220> FEATURE:
<221> NAME/KEY: misc_feature
<222> LOCATION: (31)..(31)
<223> OTHER INFORMATION: /note="C-term NH2"

<400> SEQUENCE: 101

Ser Arg Ala His Gln His Ser Met Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 102
<211> LENGTH: 31
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term (N-palm)"
<220> FEATURE:
<221> NAME/KEY: misc_feature
<222> LOCATION: (31)..(31)
<223> OTHER INFORMATION: /note="C-term NH2"

<400> SEQUENCE: 102

Ser Arg Ala His Gln His Ser Met Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 103
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term (myr)"
<220> FEATURE:
<221> NAME/KEY: MOD_RES
<222> LOCATION: (8)..(8)
<223> OTHER INFORMATION: Nle
<220> FEATURE:
<221> NAME/KEY: misc_feature
<222> LOCATION: (31)..(31)
<223> OTHER INFORMATION: /note="C-term NH2"

<400> SEQUENCE: 103

Ser Arg Ala His Gln His Ser Leu Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 104
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term (palm)"
<220> FEATURE:
<221> NAME/KEY: MOD_RES
<222> LOCATION: (8)..(8)
<223> OTHER INFORMATION: Nle
<220> FEATURE:
<221> NAME/KEY: misc_feature
<222> LOCATION: (31)..(31)
<223> OTHER INFORMATION: /note="C-term NH2"

<400> SEQUENCE: 104

Ser Arg Ala His Gln His Ser Leu Glu Thr Arg Thr Pro Asp Ile Asn
1               5                   10                  15

Pro Ala Trp Tyr Thr Gly Arg Gly Ile Arg Pro Val Gly Arg Phe
```

```
<210> SEQ ID NO 105
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term (stear)"
<220> FEATURE:
<221> NAME/KEY: MOD_RES
<222> LOCATION: (8)..(8)
<223> OTHER INFORMATION: Nle
<220> FEATURE:
<221> NAME/KEY: misc_feature
<222> LOCATION: (31)..(31)
<223> OTHER INFORMATION: /note="C-term NH2"

<400> SEQUENCE: 105

Ser Arg Ala His Gln His Ser Leu Glu Thr Arg Thr Pro Asp Ile Asn
1               5                   10                  15
Pro Ala Trp Tyr Thr Gly Arg Gly Ile Arg Pro Val Gly Arg Phe
            20                  25                  30

<210> SEQ ID NO 106
<211> LENGTH: 31
<212> TYPE: PRT
<213> ORGANISM: Rattus sp.
<220> FEATURE:
<221> NAME/KEY: misc_feature
<222> LOCATION: (31)..(31)
<223> OTHER INFORMATION: /note="C-term NH2"

<400> SEQUENCE: 106

Ser Arg Ala His Gln His Ser Met Glu Thr Arg Thr Pro Asp Ile Asn
1               5                   10                  15
Pro Ala Trp Tyr Thr Gly Arg Gly Ile Arg Pro Val Gly Arg Phe
            20                  25                  30

<210> SEQ ID NO 107
<211> LENGTH: 20
<212> TYPE: PRT
<213> ORGANISM: Rattus sp.
<220> FEATURE:
<221> NAME/KEY: misc_feature
<222> LOCATION: (20)..(20)
<223> OTHER INFORMATION: /note="C-term NH2"

<400> SEQUENCE: 107

Thr Pro Asp Ile Asn Pro Ala Trp Tyr Thr Gly Arg Gly Ile Arg Pro
1               5                   10                  15
Val Gly Arg Phe
            20

<210> SEQ ID NO 108
<211> LENGTH: 31
<212> TYPE: PRT
<213> ORGANISM: Homo sapiens
<220> FEATURE:
<221> NAME/KEY: misc_feature
<222> LOCATION: (31)..(31)
<223> OTHER INFORMATION: /note="C-term NH2"

<400> SEQUENCE: 108
```

Ser Arg Thr His Arg His Ser Met Glu Ile Arg Thr Pro Asp Ile Asn
1               5                   10                  15

Pro Ala Trp Tyr Ala Ser Arg Gly Ile Arg Pro Val Gly Arg Phe
            20                  25                  30

<210> SEQ ID NO 109
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (8)..(8)
<223> OTHER INFORMATION: Nle
<220> FEATURE:
<221> NAME/KEY: misc_feature
<222> LOCATION: (31)..(31)
<223> OTHER INFORMATION: /note="C-term NH2"

<400> SEQUENCE: 109

Ser Arg Ala His Gln His Ser Leu Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 110
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (31)..(31)
<223> OTHER INFORMATION: 1-Nal
<220> FEATURE:
<221> NAME/KEY: misc_feature
<222> LOCATION: (31)..(31)
<223> OTHER INFORMATION: /note="C-term NH2"

<400> SEQUENCE: 110

Ser Arg Ala His Gln His Ser Leu Glu Thr Arg Thr Pro Asp Ile Asn
1               5                   10                  15

Pro Ala Trp Tyr Thr Gly Arg Gly Ile Arg Pro Val Gly Arg Ala
            20                  25                  30

<210> SEQ ID NO 111
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (31)..(31)

```
<223> OTHER INFORMATION: PheCl2
<220> FEATURE:
<221> NAME/KEY: misc_feature
<222> LOCATION: (31)..(31)
<223> OTHER INFORMATION: /note="C-term NH2"

<400> SEQUENCE: 111

Ser Arg Ala His Gln His Ser Leu Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 112
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (31)..(31)
<223> OTHER INFORMATION: PheNO2
<220> FEATURE:
<221> NAME/KEY: misc_feature
<222> LOCATION: (31)..(31)
<223> OTHER INFORMATION: /note="C-term NH2"

<400> SEQUENCE: 112

Ser Arg Ala His Gln His Ser Leu Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 113
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (15)..(15)
<223> OTHER INFORMATION: Nle

<400> SEQUENCE: 113

Ser His Gln Arg Pro Ala Asp Thr His Trp Tyr Pro Arg Gly Leu Phe
1               5                   10                  15

Pro Thr Ile Gly Arg Ile Thr Ala Arg Asn Gly Glu Val Ser Arg
            20                  25                  30

<210> SEQ ID NO 114
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (1)..(1)
<223> OTHER INFORMATION: /note="N-term (N-myr)"
```

```
<220> FEATURE:
<221> NAME/KEY: MOD_RES
<222> LOCATION: (15)..(15)
<223> OTHER INFORMATION: Nle

<400> SEQUENCE: 114

Ser His Gln Arg Pro Ala Asp Thr His Trp Tyr Pro Arg Gly Leu Phe
1               5                   10                  15

Pro Thr Ile Gly Arg Ile Thr Ala Arg Asn Gly Glu Val Ser Arg
            20                  25                  30

<210> SEQ ID NO 115
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (8)..(8)
<223> OTHER INFORMATION: Nle
<220> FEATURE:
<221> NAME/KEY: MOD_RES
<222> LOCATION: (31)..(31)
<223> OTHER INFORMATION: PheF5
<220> FEATURE:
<221> NAME/KEY: misc_feature
<222> LOCATION: (31)..(31)
<223> OTHER INFORMATION: /note="C-term NH2"

<400> SEQUENCE: 115

Ser Arg Ala His Gln His Ser Leu Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 116
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (8)..(8)
<223> OTHER INFORMATION: Nle
<220> FEATURE:
<221> NAME/KEY: misc_feature
<222> LOCATION: (31)..(31)
<223> OTHER INFORMATION: /note="C-term NH2"

<400> SEQUENCE: 116

Ser Arg Ala His Gln His Ser Leu Glu Thr Arg Thr Pro Asp Ile Asn
1               5                   10                  15

Pro Ala Trp Tyr Thr Gly Arg Gly Ile Arg Pro Val Gly Arg Tyr
            20                  25                  30

<210> SEQ ID NO 117
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
```

```
<221> NAME/KEY: misc_feature
<222> LOCATION: (20)..(20)
<223> OTHER INFORMATION: /note="C-term NH2"
<220> FEATURE:
<221> NAME/KEY: misc_feature
<222> LOCATION: (1)..(20)
<223> OTHER INFORMATION: /note="Variant residues given in the sequence
      have no preference with respect to those in the annotations for
      variant positions"

<400> SEQUENCE: 117

Phe Arg Gly Val Pro Arg Ile Gly Arg Gly Thr Tyr Trp Ala Pro Asn
1               5                   10                  15

Ile Asp Pro Thr
            20

<210> SEQ ID NO 118
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (1)..(1)
<223> OTHER INFORMATION: /note="N-term (N-myr)"
<220> FEATURE:
<221> NAME/KEY: misc_feature
<222> LOCATION: (20)..(20)
<223> OTHER INFORMATION: /note="C-term NH2"
<220> FEATURE:
<221> NAME/KEY: misc_feature
<222> LOCATION: (1)..(20)
<223> OTHER INFORMATION: /note="Variant residues given in the sequence
      have no preference with respect to those in the annotations for
      variant positions"

<400> SEQUENCE: 118

Phe Arg Gly Val Pro Arg Ile Gly Arg Gly Thr Tyr Trp Ala Pro Asn
1               5                   10                  15

Ile Asp Pro Thr
            20

<210> SEQ ID NO 119
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (13)..(13)
<223> OTHER INFORMATION: Sar
<220> FEATURE:
<221> NAME/KEY: misc_feature
<222> LOCATION: (20)..(20)
<223> OTHER INFORMATION: /note="C-term NH2"

<400> SEQUENCE: 119

Thr Pro Asp Ile Asn Pro Ala Trp Tyr Thr Gly Arg Xaa Ile Arg Pro
1               5                   10                  15

Val Gly Arg Phe
            20

<210> SEQ ID NO 120
<211> LENGTH: 20
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (10)..(10)
<223> OTHER INFORMATION: NmeAla
<220> FEATURE:
<221> NAME/KEY: misc_feature
<222> LOCATION: (20)..(20)
<223> OTHER INFORMATION: /note="C-term NH2"

<400> SEQUENCE: 120

Thr Pro Asp Ile Asn Pro Ala Trp Tyr Ala Ser Arg Gly Ile Arg Pro
1               5                   10                  15

Val Gly Arg Phe
            20

<210> SEQ ID NO 121
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (20)..(20)
<223> OTHER INFORMATION: /note="C-term NH2"

<400> SEQUENCE: 121

Thr Pro Asp Ile Asn Pro Ala Trp Tyr Thr Gly Arg Gly Ala Arg Pro
1               5                   10                  15

Phe Gly Arg Phe
            20

<210> SEQ ID NO 122
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (20)..(20)
<223> OTHER INFORMATION: /note="C-term NH2"

<400> SEQUENCE: 122

Thr Pro Asp Ile Asn Pro Ala Trp Tyr Ala Ser Arg Pro Phe Arg Pro
1               5                   10                  15

Val Gly Arg Phe
            20

<210> SEQ ID NO 123
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
```

```
<223> OTHER INFORMATION: Nle
<220> FEATURE:
<221> NAME/KEY: misc_feature
<222> LOCATION: (24)..(24)
<223> OTHER INFORMATION: /note="C-term NH2"

<400> SEQUENCE: 123

Leu Glu Thr Arg Thr Pro Asp Ile Asn Pro Ala Trp Tyr Thr Gly Arg
1               5                   10                  15

Gly Ile Arg Pro Val Gly Arg Phe
            20

<210> SEQ ID NO 124
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (27)..(27)
<223> OTHER INFORMATION: /note="C-term NH2"

<400> SEQUENCE: 124

Gln His Ser Met Glu Thr Arg Thr Pro Asp Ile Asn Pro Ala Trp Tyr
1               5                   10                  15

Thr Gly Arg Gly Ile Arg Pro Val Gly Arg Phe
            20                  25

<210> SEQ ID NO 125
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: misc_feature
<222> LOCATION: (31)..(31)
<223> OTHER INFORMATION: /note="C-term NH2"

<400> SEQUENCE: 125

Ser Arg Thr His Arg His Ser Met Glu Ile Arg Thr Pro Asp Ile Asn
1               5                   10                  15

Pro Ala Trp Tyr Ala Ser Arg Gly Ile Arg Pro Val Gly Arg Phe
            20                  25                  30

<210> SEQ ID NO 126
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: misc_feature
<222> LOCATION: (20)..(20)
<223> OTHER INFORMATION: /note="C-term NH2"

<400> SEQUENCE: 126
```

```
Thr Pro Asp Ile Asn Pro Ala Trp Tyr Ala Ser Arg Gly Ile Arg Pro
1               5                   10                  15
Val Gly Arg Phe
            20
```